(12) United States Patent
Murakami et al.

(10) Patent No.: US 11,028,443 B2
(45) Date of Patent: Jun. 8, 2021

(54) MOLECULAR METHODS FOR ASSESSING UROTHELIAL DISEASE

(71) Applicants: Hitachi Chemical Co., Ltd., Tokyo (JP); Hitachi Chemical Co. America, Ltd., San Jose, CA (US); City of Sapporo, Sapporo (JP)

(72) Inventors: Taku Murakami, Irvine, CA (US); Cindy M. Yamamoto, Irvine, CA (US); Masato Mitsuhashi, Irvine, CA (US); Hiroshi Harada, Sapporo (JP)

(73) Assignees: Showa Denko Materials Co., Ltd., Tokyo (JP); Showa Denko Materials (America), Inc., San Jose, CA (US); City of Sapporo, Sapporo (JP)

( * ) Notice: Subject to any disclaimer, the term of this patent is extended or adjusted under 35 U.S.C. 154(b) by 0 days.

(21) Appl. No.: 15/756,497

(22) PCT Filed: Aug. 30, 2016

(86) PCT No.: PCT/US2016/049483
§ 371 (c)(1),
(2) Date: Feb. 28, 2018

(87) PCT Pub. No.: WO2017/040520
PCT Pub. Date: Mar. 9, 2017

(65) Prior Publication Data
US 2018/0327852 A1    Nov. 15, 2018

Related U.S. Application Data

(60) Provisional application No. 62/212,501, filed on Aug. 31, 2015, provisional application No. 62/252,257, filed on Nov. 6, 2015, provisional application No. 62/331,241, filed on May 3, 2016.

(51) Int. Cl.
*C12Q 1/6886* (2018.01)

(52) U.S. Cl.
CPC ..... *C12Q 1/6886* (2013.01); *C12Q 2600/158* (2013.01)

(58) Field of Classification Search
None
See application file for complete search history.

(56) References Cited

U.S. PATENT DOCUMENTS

| | | |
|---|---|---|
| 3,583,627 A | 6/1971 | Wilson |
| 4,293,078 A | 10/1981 | Percarpio et al. |
| 4,602,426 A | 7/1986 | Kampe et al. |
| 4,880,548 A | 11/1989 | Pall et al. |
| 4,895,706 A | 1/1990 | Root et al. |
| 4,925,572 A | 5/1990 | Pall |
| 5,139,685 A | 8/1992 | de Castro et al. |
| 5,210,015 A | 5/1993 | Gelfand et al. |
| 5,372,945 A | 12/1994 | Alchas et al. |
| 5,427,916 A | 6/1995 | Gewirtz et al. |
| 5,474,909 A | 12/1995 | Connors et al. |
| 5,491,063 A | 2/1996 | Fisher et al. |
| 5,589,568 A | 12/1996 | Higashijima et al. |
| 5,647,990 A | 7/1997 | Vassarotti |
| 5,683,698 A | 11/1997 | Chavali et al. |
| 5,733,449 A | 3/1998 | Bowers et al. |
| 5,747,256 A | 5/1998 | Yan et al. |
| 6,001,558 A | 12/1999 | Backus et al. |
| 6,007,498 A | 12/1999 | Buck et al. |
| 6,054,230 A | 4/2000 | Kato |
| 6,329,179 B1 | 12/2001 | Kopreski |
| 6,344,345 B1 | 2/2002 | Hayashizaki |
| 6,375,855 B1 | 4/2002 | Vassarotti |
| 6,391,544 B1 | 5/2002 | Salituro et al. |
| 6,475,639 B2 | 11/2002 | Shahinpoor et al. |
| 6,589,734 B1 | 7/2003 | Kacian et al. |
| 6,641,862 B1 | 11/2003 | Grot |
| 6,692,916 B2 | 2/2004 | Bevilacqua et al. |
| 6,916,634 B2 | 7/2005 | Kopreski |
| 6,964,850 B2 | 11/2005 | Bevilacqua et al. |
| 7,026,121 B1 | 4/2006 | Wohlgemuth et al. |
| 7,026,929 B1 | 4/2006 | Wallace |
| 7,332,631 B2 | 2/2008 | Hogarth et al. |
| 7,608,402 B2 | 10/2009 | Li et al. |
| 7,741,023 B2 | 6/2010 | Mitsuhashi |
| 7,745,180 B2 | 6/2010 | Mitsuhashi |
| 7,838,239 B2 | 11/2010 | Mitsuhashi et al. |
| 8,268,566 B2 | 9/2012 | Mitsuhashi et al. |
| 8,268,982 B2 | 9/2012 | Mitsuhashi |
| 8,567,609 B2 | 10/2013 | Landrigan et al. |
| 8,574,716 B2 | 11/2013 | Wu et al. |
| 8,591,391 B2 | 11/2013 | Chavarria et al. |
| 8,916,351 B2 | 12/2014 | Murakami |
| 9,012,615 B2 | 4/2015 | Mitsuhashi et al. |
| 9,150,920 B2 | 10/2015 | Mitsuhashi et al. |
| 9,458,496 B2 | 10/2016 | Mitsuhashi et al. |
| 9,662,649 B2 | 3/2017 | Mitsuhashi et al. |
| 9,719,129 B2 | 8/2017 | Mitsuhashi et al. |
| 9,790,542 B2 | 10/2017 | Mitsuhashi et al. |
| 10,266,895 B2 | 4/2019 | Mitsuhashi et al. |
| 10,370,719 B2 | 8/2019 | RamachandraRao et al. |

(Continued)

FOREIGN PATENT DOCUMENTS

| | | |
|---|---|---|
| EP | 0 588 564 | 3/1994 |
| EP | 1 243 274 | 9/2002 |
| EP | 1 344 837 | 9/2003 |
| EP | 1 672 062 | 6/2006 |
| JP | 1983-159420 | 9/1983 |

(Continued)

OTHER PUBLICATIONS

Enard et al. (Science 2002 vol. 296 p. 340) (Year: 2002).*

(Continued)

*Primary Examiner* — Katherine D Salmon
(74) *Attorney, Agent, or Firm* — Knobbe Martens Olson & Bear LLP

(57) ABSTRACT

The present disclosure relates to methods of collecting exosomes and microvesicles (EMV) from urine, isolating corresponding mRNA, and analyzing expression patterns in order to diagnose and treat various urothelial cancers. In particular, various expression patterns are analyzed through a unique diagnostic formula.

19 Claims, 42 Drawing Sheets

Specification includes a Sequence Listing.

(56) References Cited

U.S. PATENT DOCUMENTS

| | | |
|---|---|---|
| 2001/0006789 A1 | 7/2001 | Maino et al. |
| 2001/0051344 A1 | 12/2001 | Shalon et al. |
| 2002/0006613 A1 | 1/2002 | Shyjan et al. |
| 2002/0011450 A1 | 1/2002 | Kelly et al. |
| 2002/0048566 A1 | 4/2002 | El-Deiry et al. |
| 2002/0106684 A1 | 8/2002 | Kopreski |
| 2002/0107140 A1 | 8/2002 | Hampden-Smith et al. |
| 2002/0146696 A1 | 10/2002 | Burgoyne et al. |
| 2003/0036077 A1 | 2/2003 | Chenchik |
| 2003/0139781 A1 | 7/2003 | Whitehead |
| 2003/0148280 A1 | 8/2003 | Harris et al. |
| 2003/0148345 A1 | 8/2003 | Kopreski |
| 2003/0203453 A1 | 10/2003 | Leonard |
| 2003/0228512 A1 | 12/2003 | Vyas et al. |
| 2004/0005474 A1 | 1/2004 | Charnock et al. |
| 2004/0029124 A1 | 2/2004 | Zohlnhofer et al. |
| 2004/0072193 A1 | 4/2004 | Mitsuhashi |
| 2004/0072268 A1 | 4/2004 | Shiekhatter |
| 2004/0101730 A1 | 5/2004 | Hirano et al. |
| 2004/0149965 A1 | 8/2004 | Otsuki et al. |
| 2004/0152204 A1 | 8/2004 | Gauthier |
| 2004/0170961 A1 | 9/2004 | Meritet et al. |
| 2004/0203037 A1 | 10/2004 | Lo et al. |
| 2004/0245163 A1 | 12/2004 | Lim et al. |
| 2004/0258570 A1 | 12/2004 | Beebe et al. |
| 2004/0265864 A1 | 12/2004 | Mitsuhashi |
| 2005/0064472 A1 | 3/2005 | Shekar et al. |
| 2005/0095592 A1 | 5/2005 | Jazaeri et al. |
| 2006/0008804 A1 | 1/2006 | Chibout et al. |
| 2006/0008807 A1 | 1/2006 | O'Hara et al. |
| 2006/0057129 A1 | 3/2006 | Lebkowski et al. |
| 2006/0144790 A1 | 7/2006 | Kelly et al. |
| 2006/0159982 A1 | 7/2006 | Yoshitake et al. |
| 2006/0106684 A1 | 8/2006 | Kopreski |
| 2006/0198787 A1 | 9/2006 | Blatt |
| 2006/0204950 A1 | 9/2006 | Ilercil et al. |
| 2006/0251965 A1 | 11/2006 | Nagayama et al. |
| 2006/0281091 A1 | 12/2006 | Lavedan |
| 2007/0122877 A1 | 5/2007 | Abulafia-Lapid et al. |
| 2007/0196835 A1 | 8/2007 | Bankaitis-Davis et al. |
| 2007/0196871 A1 | 8/2007 | Reich |
| 2007/0243161 A1 | 10/2007 | Olek |
| 2007/0254351 A1 | 11/2007 | Abrignani et al. |
| 2007/0264272 A1 | 11/2007 | Perreault et al. |
| 2007/0292448 A1 | 12/2007 | Lebkowski et al. |
| 2008/0009009 A1 | 1/2008 | Mitsuhashi |
| 2008/0015162 A1 | 1/2008 | Bhanot et al. |
| 2008/0025967 A1 | 1/2008 | Doi et al. |
| 2008/0299558 A1 | 4/2008 | Kondo et al. |
| 2008/0118576 A1 | 5/2008 | Theodorescu et al. |
| 2008/0135564 A1 | 6/2008 | Romero |
| 2008/0188816 A1 | 8/2008 | Shimazaki et al. |
| 2008/0206761 A1 | 8/2008 | Mitsuhashi |
| 2008/0233573 A1 | 9/2008 | Storm et al. |
| 2008/0261207 A1 | 10/2008 | Mitsuhashi |
| 2008/0268429 A1 | 10/2008 | Pietrzkowski |
| 2009/0011410 A1 | 1/2009 | Mitsuhashi |
| 2009/0023149 A1 | 1/2009 | Knudsen |
| 2009/0032394 A1 | 2/2009 | Wu et al. |
| 2009/0136447 A1 | 5/2009 | Cannon et al. |
| 2009/0139261 A1 | 6/2009 | Nakano et al. |
| 2009/0149333 A1 | 6/2009 | Knudsen et al. |
| 2009/0155838 A1 | 6/2009 | Hale |
| 2009/0173632 A1 | 7/2009 | Nagayama et al. |
| 2009/0203064 A1 | 8/2009 | Ericson |
| 2009/0204190 A1 | 8/2009 | Sestito |
| 2009/0215064 A1 | 8/2009 | Mitsuhashi et al. |
| 2009/0258379 A1 | 10/2009 | Klein et al. |
| 2009/0298071 A1 | 12/2009 | Mitsuhashi et al. |
| 2009/0301875 A1 | 12/2009 | Wu et al. |
| 2009/0311684 A1 | 12/2009 | Mitsuhashi et al. |
| 2010/0021424 A1 | 1/2010 | Brichard et al. |
| 2010/0027315 A1 | 2/2010 | Kim |
| 2010/0047730 A1 | 2/2010 | Fergueson et al. |
| 2010/0113290 A1 | 5/2010 | Klass et al. |
| 2010/0137149 A1* | 6/2010 | Shin ............ C12Q 1/6813 506/8 |
| 2010/0141085 A1 | 6/2010 | Wu et al. |
| 2010/0184046 A1 | 7/2010 | Klass et al. |
| 2010/0196426 A1 | 8/2010 | Skog |
| 2010/0203529 A1 | 8/2010 | Kuslich et al. |
| 2010/0216131 A1 | 8/2010 | Luthra et al. |
| 2010/0143898 A1 | 10/2010 | Kutyavin |
| 2011/0123986 A1 | 5/2011 | Narain et al. |
| 2011/0143348 A1 | 6/2011 | Tomigahara et al. |
| 2011/0171647 A1 | 7/2011 | Tomigahara et al. |
| 2011/0189674 A1 | 8/2011 | Tomigahara et al. |
| 2011/0195426 A1 | 8/2011 | Russo |
| 2011/0223583 A1 | 9/2011 | Gordon et al. |
| 2011/0236340 A1 | 9/2011 | Mansky et al. |
| 2011/0262468 A1 | 10/2011 | Fanti et al. |
| 2011/0262921 A1* | 10/2011 | Sabichi ............ C12Q 1/6886 435/6.12 |
| 2011/0287964 A1 | 11/2011 | Bonventre et al. |
| 2012/0211566 A1 | 8/2012 | Hensel et al. |
| 2012/0220484 A1 | 8/2012 | Halloran |
| 2012/0258076 A1 | 10/2012 | Mitsuhashi |
| 2012/0264628 A1 | 10/2012 | Okamoto et al. |
| 2012/0309645 A1 | 12/2012 | Keller et al. |
| 2013/0084577 A1 | 4/2013 | Mitsuhashi |
| 2013/0123124 A1 | 5/2013 | Kunkel |
| 2013/0226032 A1 | 5/2013 | Mitsuhashi |
| 2013/0165338 A1 | 6/2013 | Schmidt-Ott et al. |
| 2013/0172208 A1 | 7/2013 | Mitsuhashi |
| 2013/0197514 A1 | 8/2013 | Jiang |
| 2013/0244256 A1 | 9/2013 | Clarke et al. |
| 2013/0323751 A1 | 12/2013 | Singbartl et al. |
| 2013/0337462 A1 | 12/2013 | Mergemeier |
| 2014/0141986 A1 | 5/2014 | Spetzler et al. |
| 2014/0147470 A1 | 5/2014 | Mitsuhashi |
| 2014/0148348 A1 | 5/2014 | Kuslich |
| 2014/0148350 A1 | 5/2014 | Spetzler |
| 2014/0194613 A1 | 7/2014 | Skog et al. |
| 2015/0018227 A1 | 1/2015 | Taylor et al. |
| 2015/0100242 A1 | 4/2015 | Zeng et al. |
| 2015/0218638 A1 | 8/2015 | Mitsuhashi |
| 2015/0275301 A1 | 10/2015 | Mitsuhashi et al. |
| 2015/0301055 A1 | 10/2015 | Spetzler |
| 2015/0322530 A1 | 11/2015 | Orsulic et al. |
| 2016/0060705 A1 | 3/2016 | O'Donnell et al. |
| 2016/0153053 A1 | 6/2016 | Skog et al. |
| 2016/0222456 A1 | 8/2016 | Yamamoto |
| 2016/0237496 A1 | 8/2016 | Mitsuhashi |
| 2017/0184575 A1 | 6/2017 | Murakami |
| 2017/0247744 A1 | 8/2017 | Mitsuhashi |
| 2017/0283789 A1 | 10/2017 | Yamamoto |
| 2018/0265914 A1 | 9/2018 | Murakami |
| 2019/0264283 A1 | 8/2019 | Mitsuhashi |

FOREIGN PATENT DOCUMENTS

| | | |
|---|---|---|
| JP | 1984-225195 | 12/1984 |
| JP | 1996-285839 | 1/1996 |
| JP | 1997-067336 | 3/1997 |
| JP | 2003-61678 | 3/2003 |
| JP | 2007-181440 | 7/2007 |
| JP | 2008-005840 | 1/2008 |
| JP | 2008-151517 | 7/2008 |
| JP | 2009-178057 | 8/2009 |
| JP | 2012-185173 | 9/2012 |
| JP | 2014-035186 | 2/2014 |
| WO | WO 1991/08308 | 6/1991 |
| WO | WO 1992/01813 | 1/1992 |
| WO | WO 1993/19831 | 10/1993 |
| WO | WO 1998/22825 | 5/1998 |
| WO | WO 1998/47004 | 10/1998 |
| WO | WO 2000/04193 | 1/2000 |
| WO | WO 2000/016796 | 3/2000 |
| WO | WO 2000/35473 | 6/2000 |
| WO | WO 2000/52209 | 9/2000 |
| WO | WO 2000/76492 | 12/2000 |
| WO | WO 2001/04361 | 1/2001 |
| WO | WO 2001/051170 | 7/2001 |
| WO | WO 2001/079486 | 10/2001 |

(56) References Cited

FOREIGN PATENT DOCUMENTS

| | | |
|---|---|---|
| WO | WO 2002/057414 | 7/2002 |
| WO | WO 2003/020878 | 3/2003 |
| WO | WO 2003/030719 | 4/2003 |
| WO | WO 2003/031969 | 4/2003 |
| WO | WO 2003/040404 | 5/2003 |
| WO | WO 2003/059333 | 7/2003 |
| WO | WO 2003/076660 | 9/2003 |
| WO | WO 2003/090694 | 11/2003 |
| WO | WO 2003/099312 | 12/2003 |
| WO | WO 2004/075321 | 9/2004 |
| WO | WO 2005/044792 | 5/2005 |
| WO | WO 2006/010464 | 2/2006 |
| WO | WO 2006/076492 | 7/2006 |
| WO | WO 2006/091934 | 8/2006 |
| WO | WO 2006/093257 | 9/2006 |
| WO | WO 2006/110091 | 10/2006 |
| WO | WO 2006/116721 | 11/2006 |
| WO | WO 2006/133399 | 12/2006 |
| WO | WO 2007/038501 | 4/2007 |
| WO | WO 2007/084796 | 6/2007 |
| WO | WO 2007/106939 | 9/2007 |
| WO | WO 2007/004915 | 12/2007 |
| WO | WO 2008/092993 | 8/2008 |
| WO | WO 2008/095907 | 8/2008 |
| WO | WO 2008/106451 | 9/2008 |
| WO | WO 2008/113119 | 9/2008 |
| WO | WO 2008/116867 | 10/2008 |
| WO | WO 2009/000744 | 12/2008 |
| WO | WO 2009/015357 | 1/2009 |
| WO | WO 2009/057695 | 5/2009 |
| WO | WO 2009/073152 | 6/2009 |
| WO | WO 2009/083653 | 7/2009 |
| WO | WO 2009/100029 | 8/2009 |
| WO | WO 2009/120561 | 10/2009 |
| WO | WO 2010/056337 | 5/2010 |
| WO | WO 2010/086163 | 8/2010 |
| WO | WO 2011/031892 | 3/2011 |
| WO | WO 2011/054893 | 5/2011 |
| WO | WO 2011/100458 | 8/2011 |
| WO | WO 2011/112961 | 9/2011 |
| WO | WO 2011/127219 A1 | 10/2011 |
| WO | WO 2012/057498 | 5/2012 |
| WO | WO 2012/102963 | 8/2012 |
| WO | WO 2012/125470 | 9/2012 |
| WO | WO 2013/028788 A1 | 2/2013 |
| WO | WO 2013/041913 | 3/2013 |
| WO | WO 2013/043922 | 3/2013 |
| WO | WO 2013/134786 | 9/2013 |
| WO | WO 2013/188846 | 12/2013 |
| WO | WO 2013/192616 | 12/2013 |
| WO | WO 2014/021125 | 2/2014 |
| WO | WO 2014/130825 | 8/2014 |
| WO | WO 2014/182330 A1 | 11/2014 |
| WO | WO 2015/021158 | 2/2015 |
| WO | WO 2015/050891 | 4/2015 |
| WO | WO 2015/082372 A1 | 6/2015 |
| WO | WO 2015/179773 | 11/2015 |

OTHER PUBLICATIONS

Reis et al. (Onocology Letters vol. 2 2011 p. 1149) (Year: 2011).*
Common Cancer Types [Internet]. Natl. Cancer Inst. Available from: http://www.cancer.gov/types/common-cancers [cited Aug. 6, 2015].
The Cancer Genome Atlas Research Network: Comprehensive molecular characterization of urothelial bladder carcinoma. *Nature* [Internet] advance online publication: 2014 Available from: http://www.nature.com/nature/journal/vaop/ncurrent/full/nature12965.html [cited Feb. 21, 2014].
Anders S, et al., Count-based differential expression analysis of RNA sequencing data using R and Bioconductor. *Nat. Protoc.* 8: 1765-1786, 2013.
Baldi P, et al., A Bayesian framework for the analysis of microarray expression data: regularized t-test and statistical inferences of gene changes. *Bioinformatics* 17: 509-519, 200.
Botteman Mf, et al., The health economics of bladder cancer: a comprehensive review of the published literature. *PharmacoEconomics* 21: 1315-1330, 2003.
MeléM, et al., The human transcriptome across tissues and individuals. *Science* 348: 660-665, 2015.
Mi H, et al., Large-scale gene function analysis with the PANTHER classification system. *Nat. Protoc.* 8: 1551-1566, 2013.
Mitsuhashi M, et al., Quantification of mRNA in Whole Blood by Assessing Recovery of RNA and Efficiency of cDNA Synthesis. *Clin. Chem.* 52: 634-642, 2006.
Murakami et al. "Development of Glomerulus-, Tubuel-, and Collecting Duct-Specific mRNA Assay in Human Urinary Exosomes and Microvesicles," PLOS One vol. 9, Oct. 2014, pp. 1-10.
Perez A, et al., A Pilot Study on the Potential of RNA-Associated to Urinary Vesicles as a Suitable Non-Invasive Source for Diagnostic Purposes in Bladder Cancer. *Cancers* 6: 179-192, 2014.
Sing T, et al., ROCR: visualizing classifier performance in R. *Bioinformatics* 21: 3940-3941, 2005.
Smith Zl, et al., Urinary markers for bladder cancer. *F1000Prime Rep.* [Internet] 5: 2013 Available from: http://www.ncbi.nlm.nih.gov/pmc/articles/PMC3702217/ [cited Aug. 17, 2015].
Théry C, et al., Membrane vesicles as conveyors of immune responses. Nat. Rev. Immunol. 9: 581-593, 2009.
Théry C, et al., Exosomes: composition, biogenesis and function. Nat. Rev. Immunol. 2: 569-579, 2002.
Jan. 17, 2017 International Search Report and Written Opinion for PCT/US2016/049483 filed Aug. 30, 2016.
Alvarez Ml, et al., Comparison of protein, microRNA, and mRNA yields using different methods of urinary exosome isolation for the discovery of kidney disease biomarkers. Kidney Int. 82: 1024-1032, 2012.
Bishay et al., Carcinogenesis (2001) vol. 22:1179.
Conde-Vancells et al., Candidate biomarkers in exosome-like vesicles purified from rat and mouse urine samples, Proteomics Clin Appl 4(4):416-25 (2010).
Fuchs et al., "An Exploratory Evaluation of the Utility of Transcriptional and Urnary Kidney Injury Biomarkers for the Prediction of Aristolochic Acid-Induced Renal Injury in Male Rates," Veterinary Pathology, 2014, vol. 51 (3) 680-694.
Golub, et al.: "Molecular Classification of Cancer: Class Discovery and Class Prediction by Gene Expression Monitoring," Science, vol. 286, pp. 531-537, Oct. 1999.
Gonzales et al., Chapter 6: Isolation and Purification of Exosomes in Urine in Alex J. Rai (ed.), The Urinary Proteome: Methods and Protocols, Methods in Molecular Biology, vol. 641, pp. 89-99, 2010.
Gonzales et al., Large-scale proteomics and phosphoproteomics of urinary exosomes, J Am Soc Nephrol, 20(2):363-79 (2009).
Hewitt et al., Discovery of Protein Biomarkers for Renal Diseases, J Am Soc Nephrol (2004) vol. 15(7):1677-1689.
Hoorn et al., Prospects for urinary proteomics: exosomes as a source of urinary biomarkers, Nephrology, 10:283-290 (2005).
Ka S-M, et al., Urine Annexin A1 as an Index for Glomerular Injury in Patients. Disease Markers, vol. 2014, Article ID 854163, 12 page, published Jan. 20, 2014.
Keller et al., "Body fluid derived exosomes as a novel template for clinical diagnostics," Journal of Translational Medicine, vol. 9, 86, Jun. 2011, printed as pp. 1/9-9/9.
Kim et al.: "Predictive value of progression-related gene classifier in primay non-muscle invasive bladder cancer," Molecular Cancer 2010, 9:3 (2010).
Koga et al., Purification, characterization and biological significance of tumor-derived exosomes, Anticancer Res, 25(6A):3703-7 (2005).
Miranda et al., Nucleic acids within urinary exosomes/microvesicles are potential biomarkers for renal disease, Kidney Intl (2010) vol. 78(2):191-199.
Mitchell et al., Can urinary exosomes act as treatment response markers in prostate cancer? J Transl Med, 12:7:4 (2009).

(56) References Cited

OTHER PUBLICATIONS

Nilsson et al., Prostate cancer-derived urine exosomes: a novel approach to biomarkers for prostate cancer, Br J Cancer 100:1603-1607 (2009).

Pepe, et al, "Phases of Biomarker Development for Early Detection of Cancer," Journal of the National Cancer Institute, vol. 93, No. 14, pp. 1054-1061, Jul. 2001.

Pisitkun et al., Identification and proteomic profiling of exosomes in human urine, Proc Natl Acad Sci USA, 101:13368-73 (2004).

Properzi F, et al., Exosomes: the future of biomarkers in medicine. Biomark. Med. 7: 769-778, 2013.

Pusztai et al.: "Clinical trial design for microarray predictive marker discovery and assessment," Annals of Oncology 15: 1731-1737, 2004.

Smalley et al., Isolation and identification of potential urinary microparticle biomarkers of bladder cancer, J Proteome Res 7:2088-96 (2008).

Strausberg et al., Reading the Molecular Signatures of Cancer, Microarrays & Cancer Res (2002) pp. xi-xvi.

Tockman et al., Considerations in bringing a cancer biomarker to clinical application, Cancer Res 1:52(9Suppl):2711s-2718s (1992).

Van Niel et al., Exosomes: a common pathway for a specialized function, J Biochem 140(1):13-21 (2006).

Van't Veer et al., Enabling personalized cancer medicine through analysis of gene-expression patterns, Nature 452(7187):564-70 (2008).

Wellmann et al., Detection of differentially expressed genes in lymphomas using cDNA arrays: identification of clusterin as a new diagnostic marker for anaplastic large-cell lymphomas, Blood (2000) vol. 96(2):398-404.

Wu, Analysing gene expression data from DNA microarrays to identify candidate genes, J Path (2001) vol. 195:53-65.

Yuan Y, et al., Urinary candidate biomarker discovery in a rat unilateral ureteral obstruction model. Sci. Rep., Mar. 20, 2015.

Zhou et al., Urinary exosomal transcription factors, a new class of biomarkers for renal disease, Kidney Intl (2008) vol. 74(5):613-621.

Mar. 6, 2018 International Preliminary Report on Patentability for PCT/US2016/049483 filed Aug. 30, 2016.

\* cited by examiner

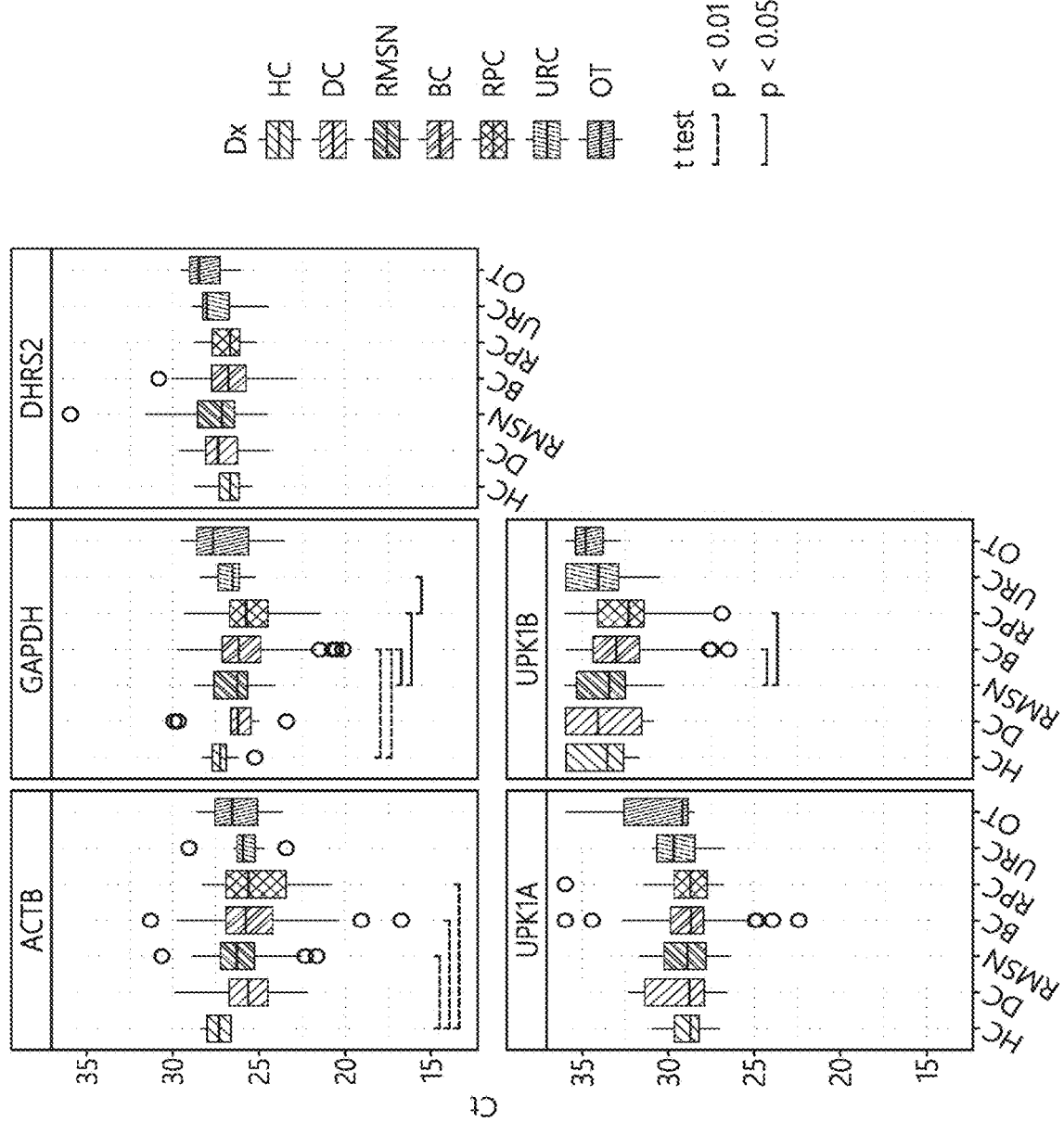
FIG. 2D₁

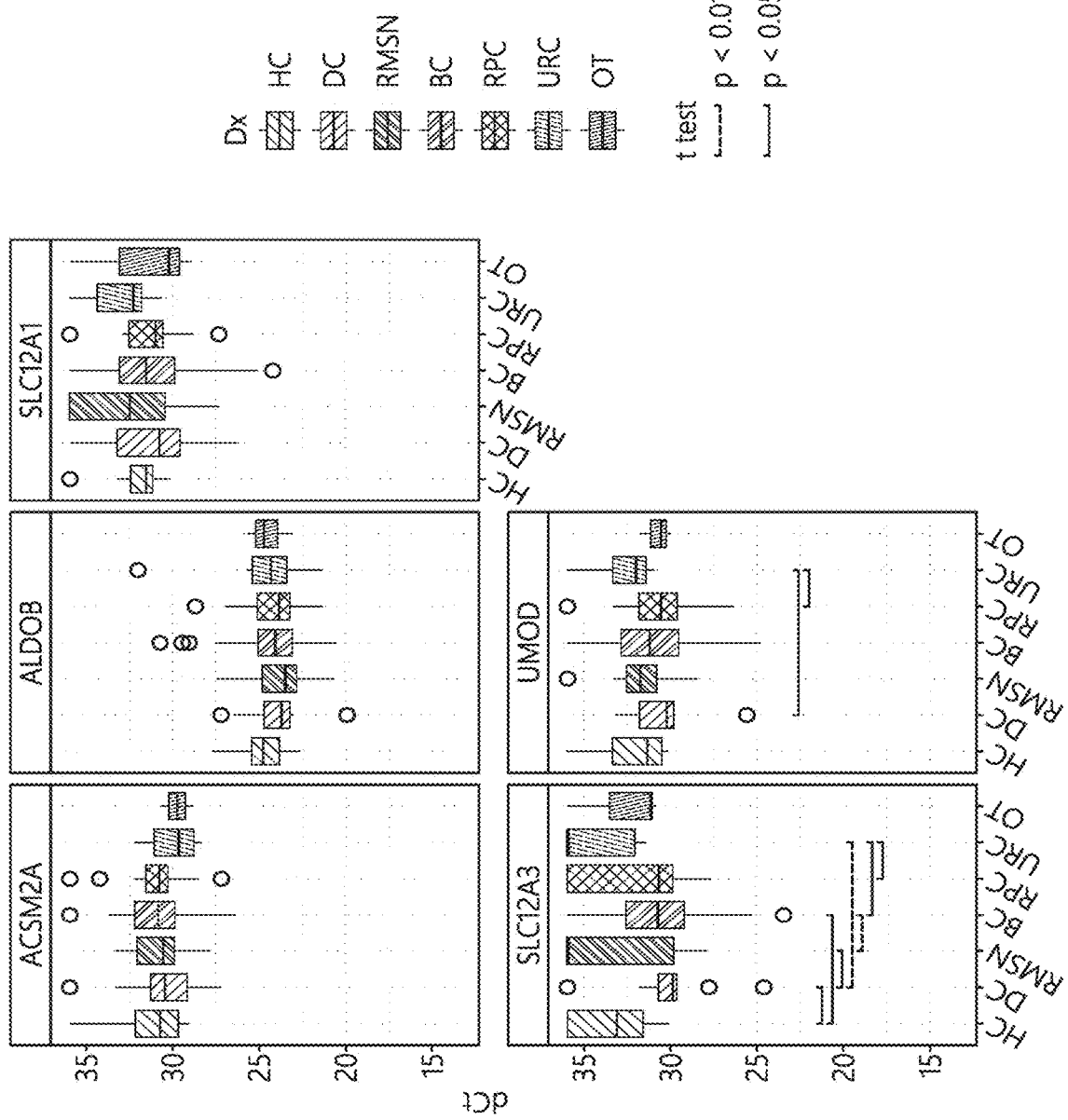
FIG. 2D₂

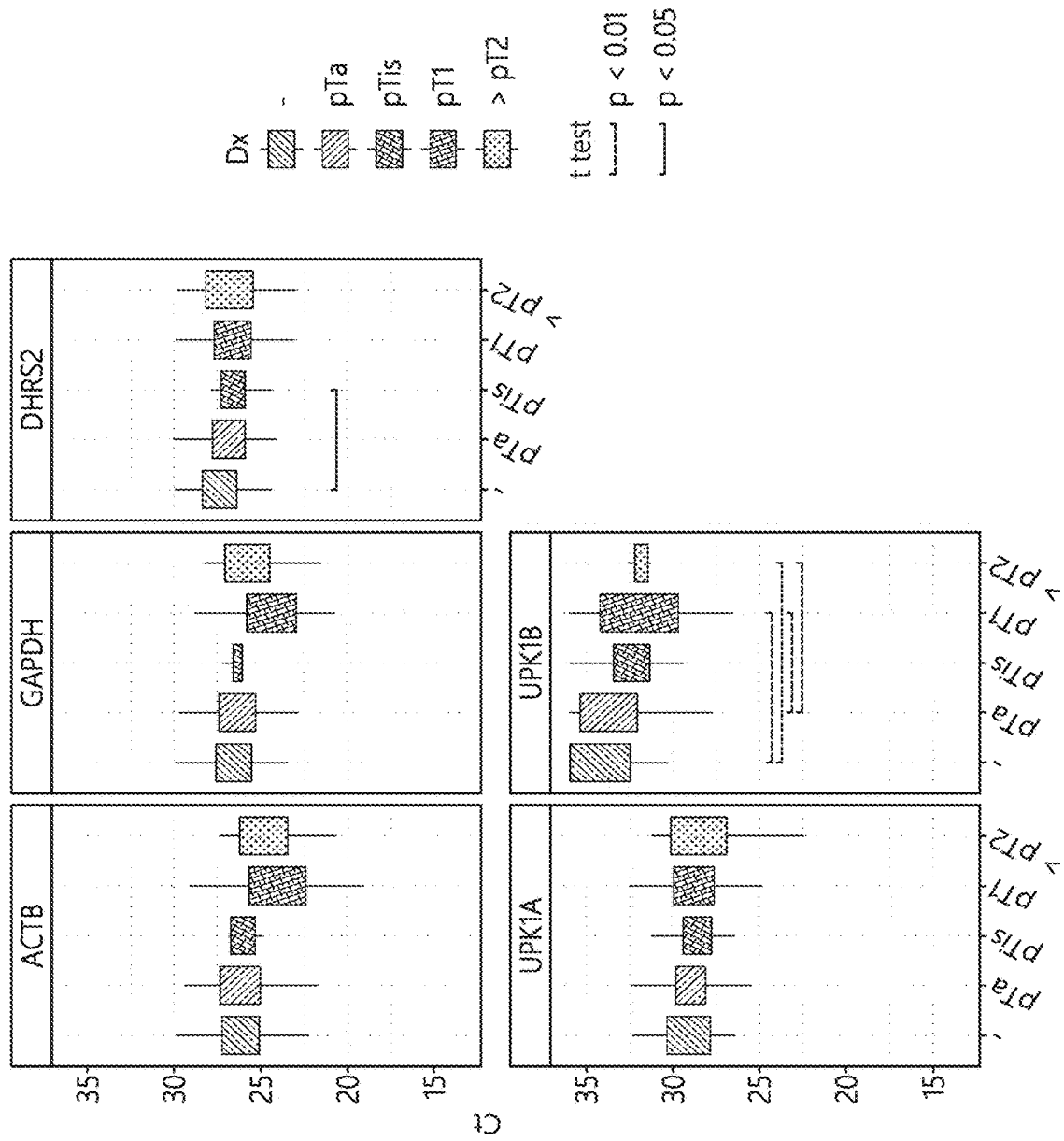
FIG. 2E_1

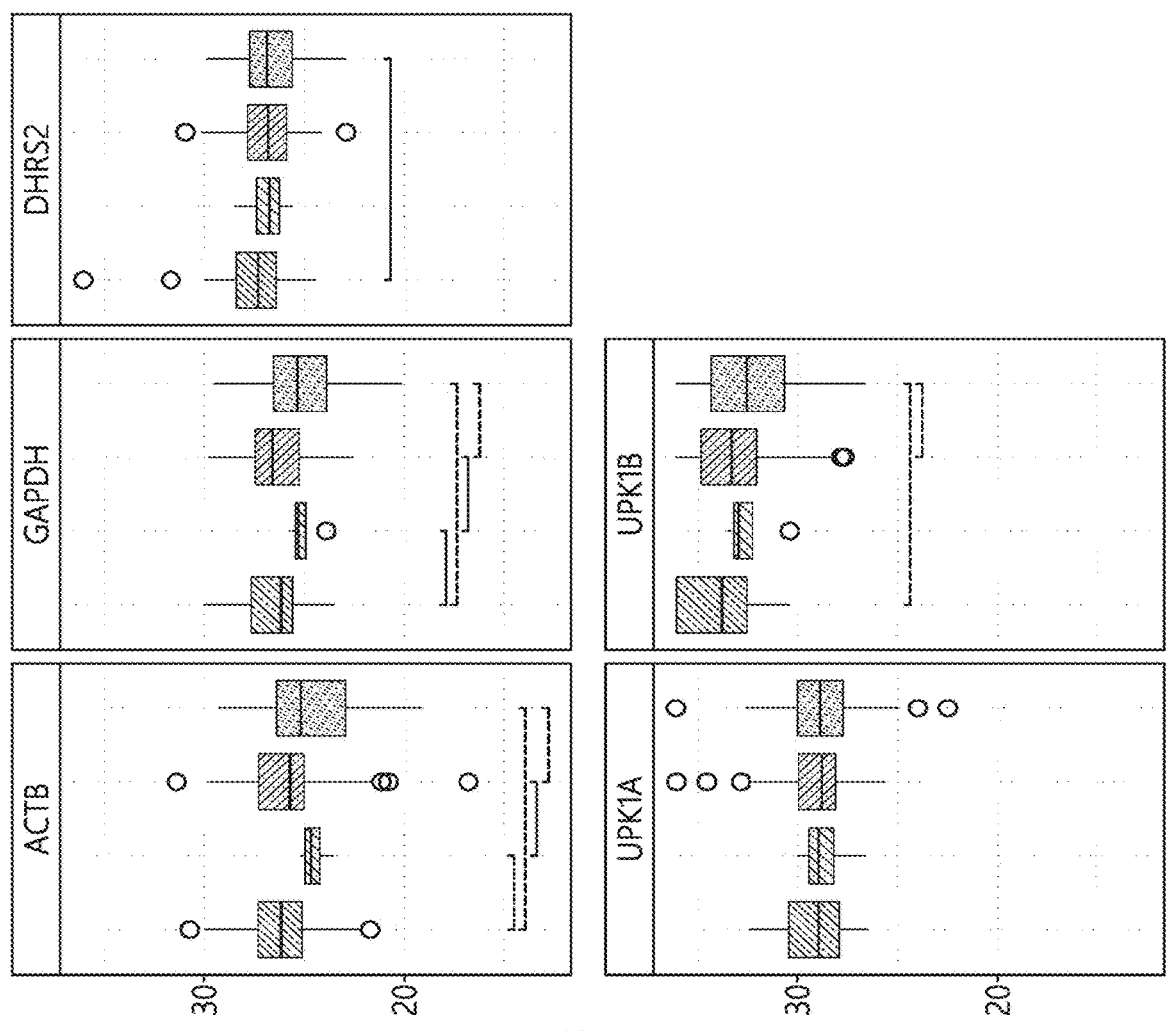
FIG. 2F₁

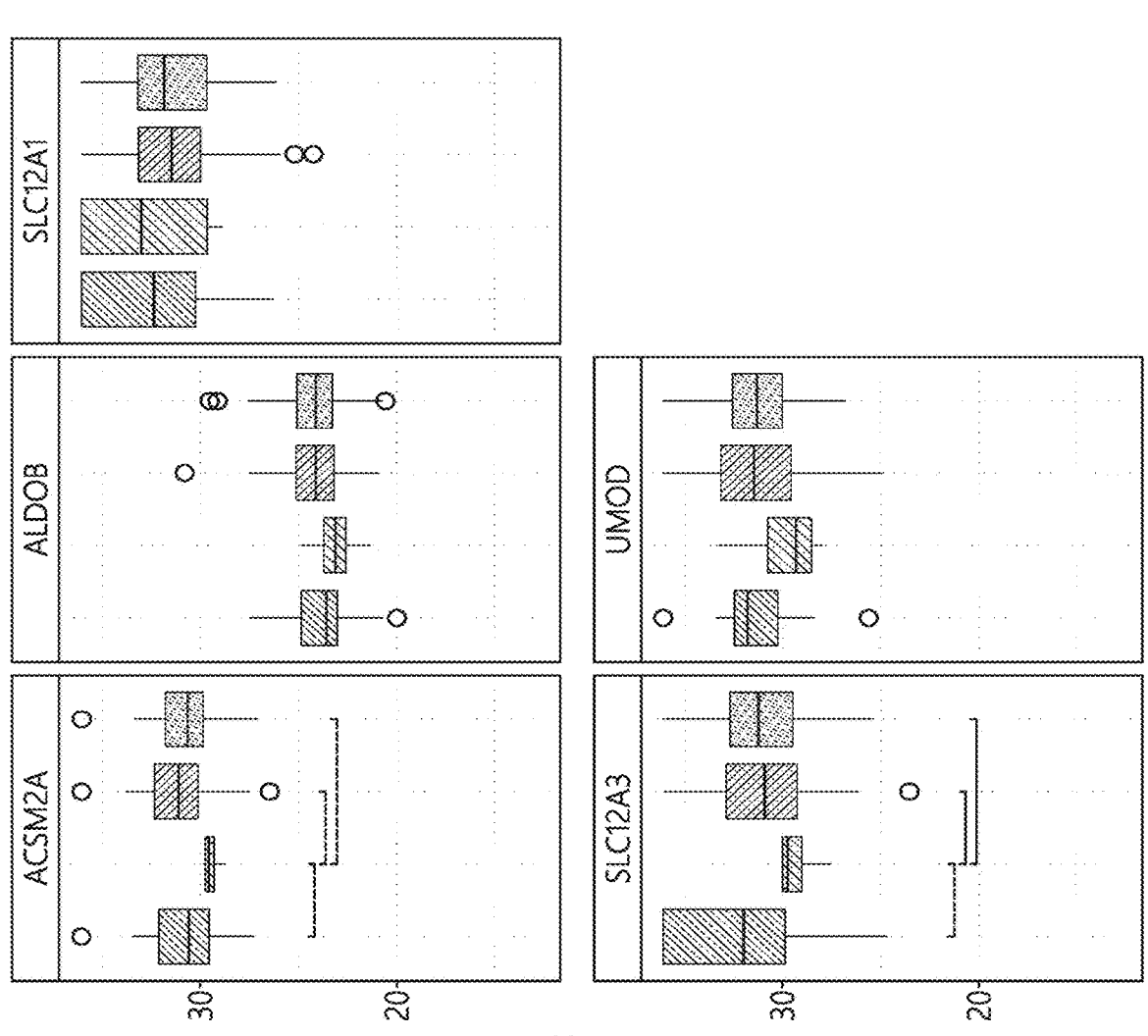
FIG. 2F₂

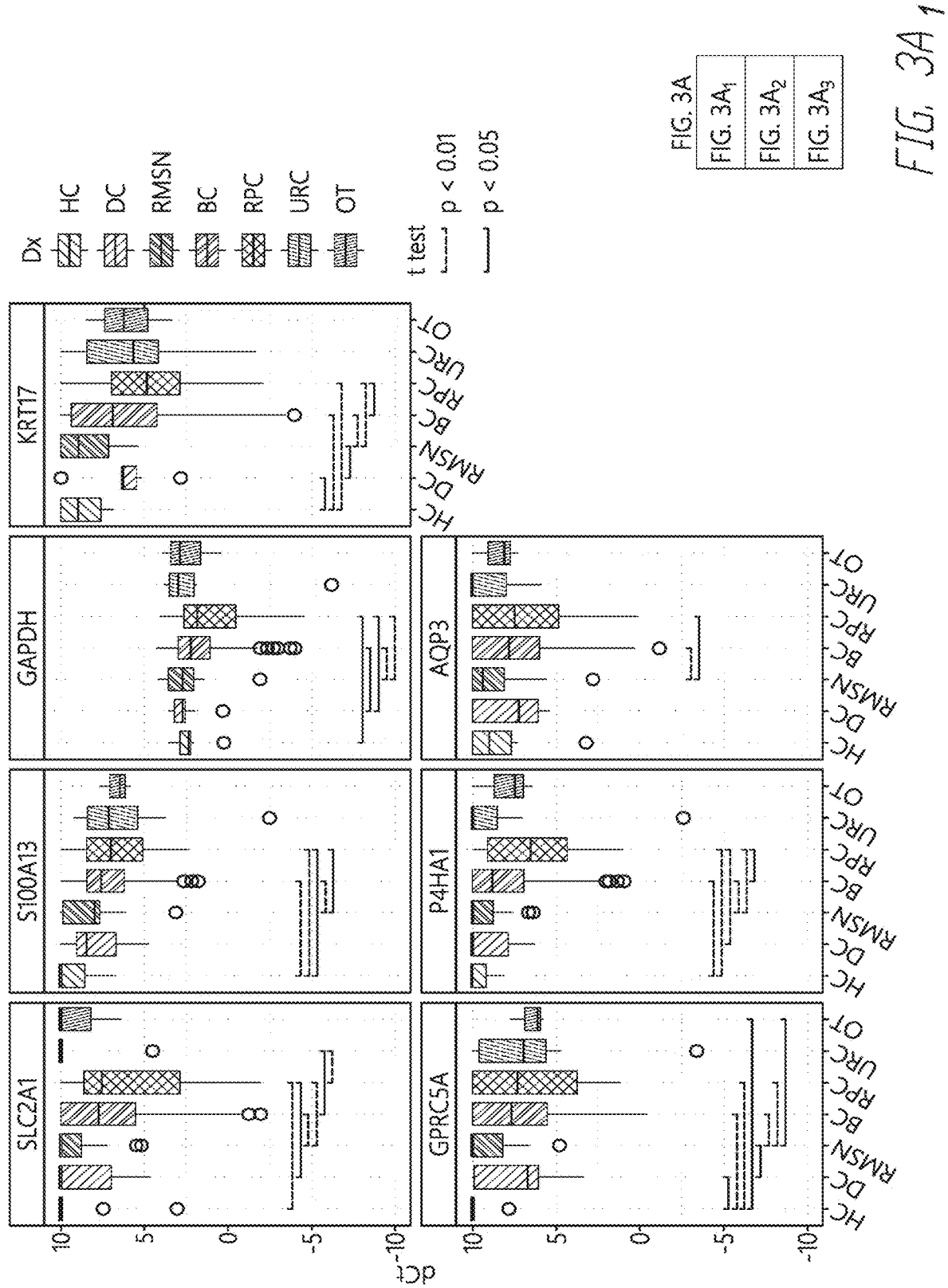
FIG. 3A₁

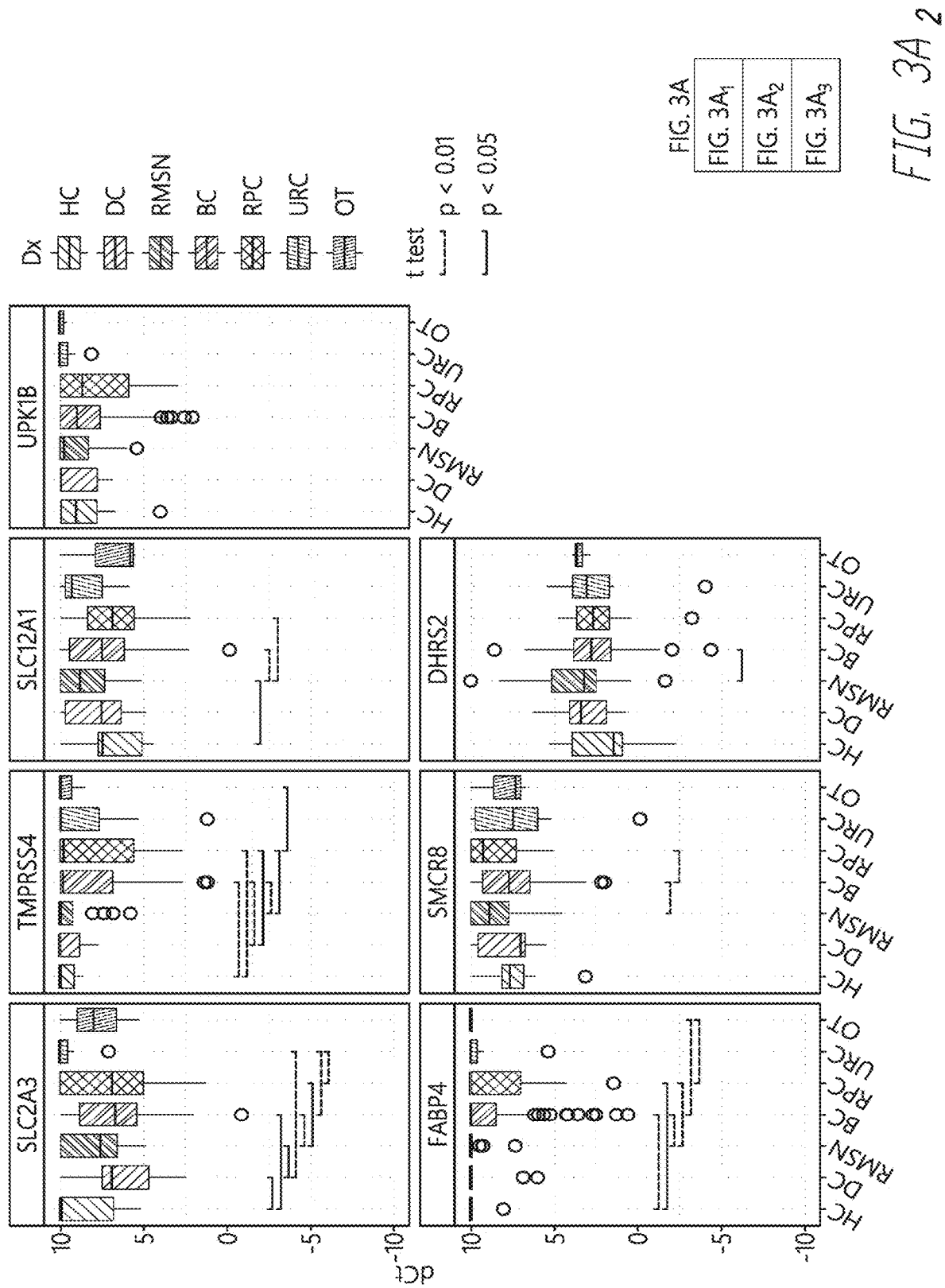
FIG. 3A₂

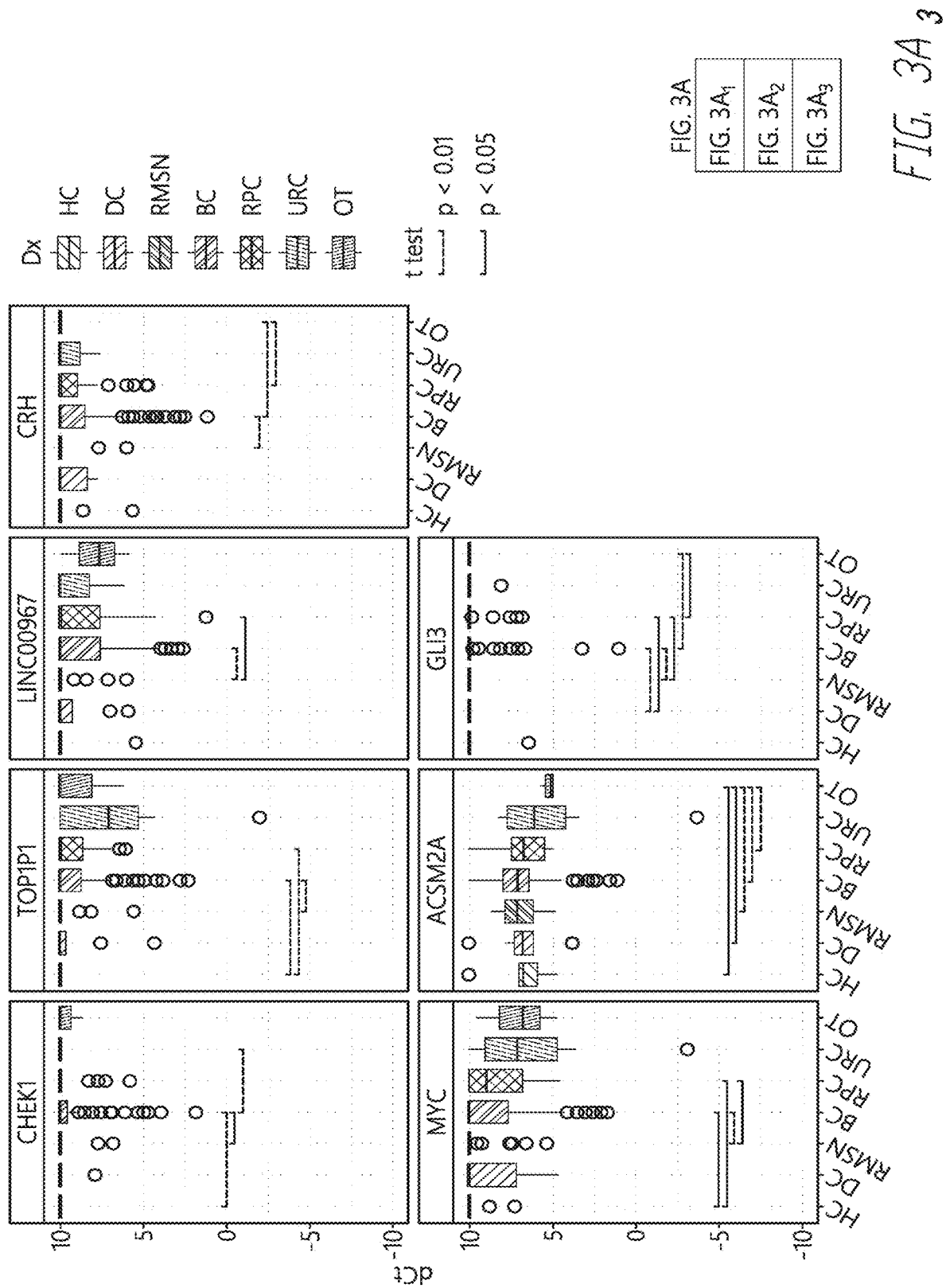
FIG. 3A₃

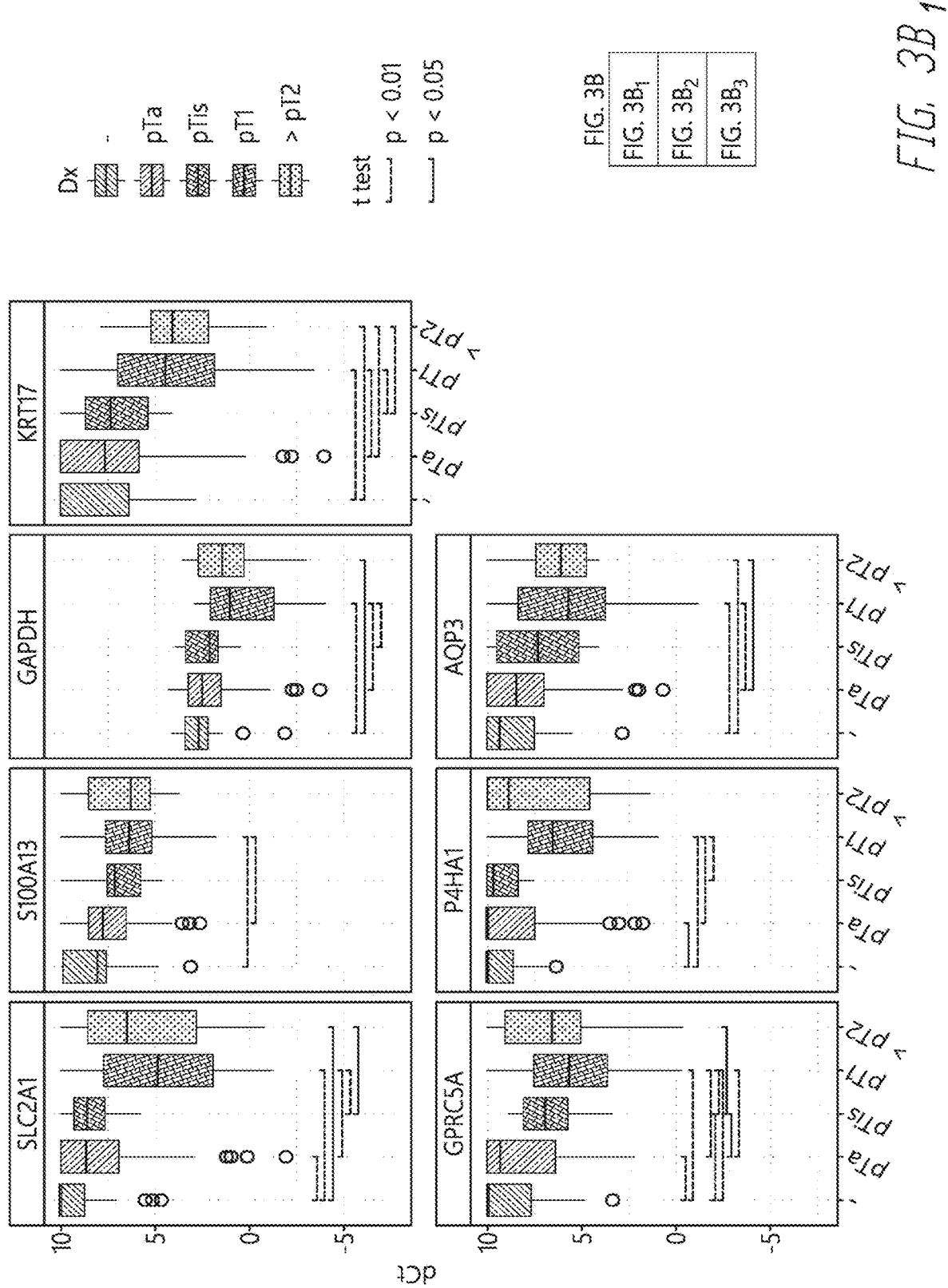
FIG. 3B₁

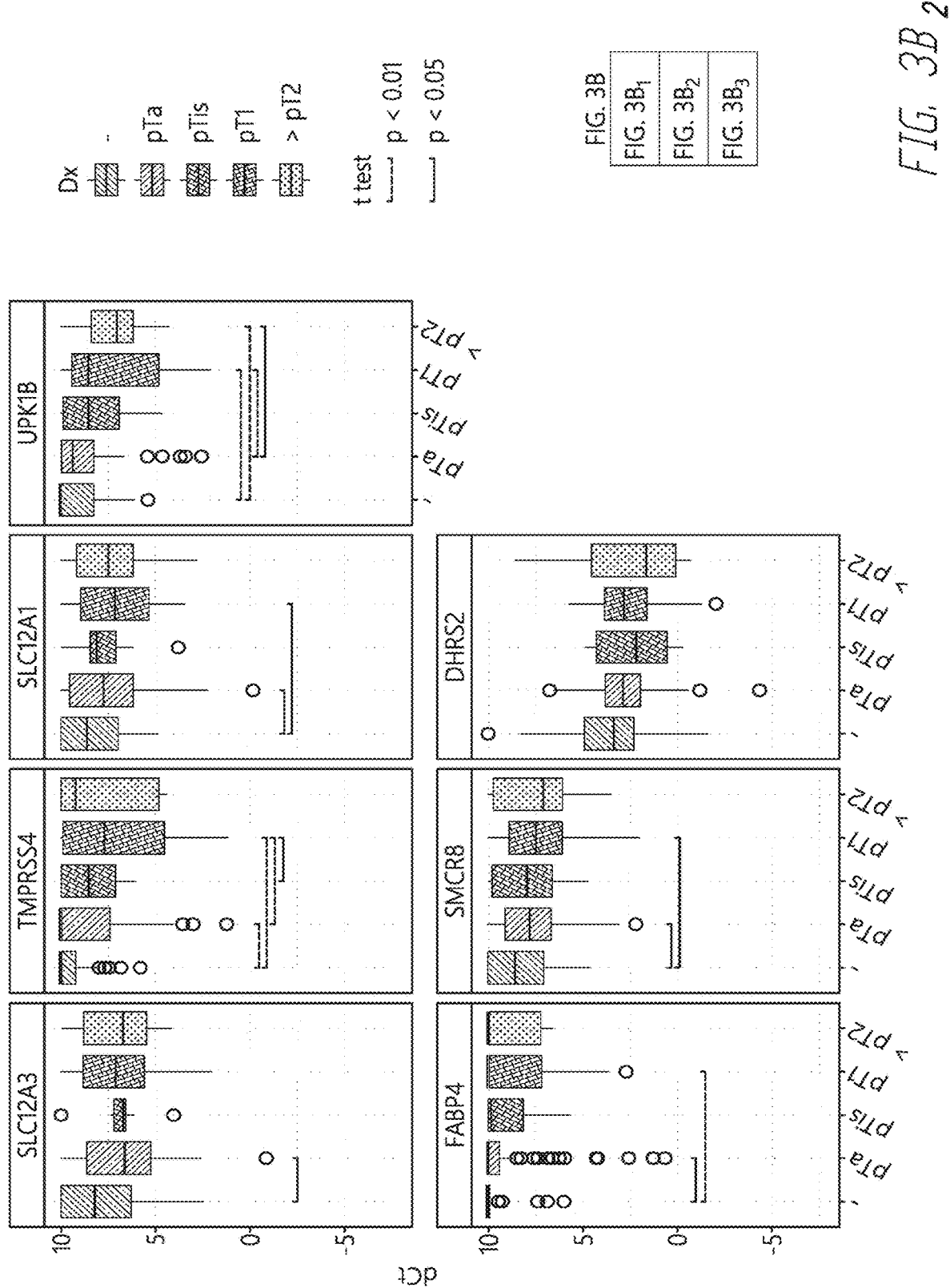
FIG. 3B₂

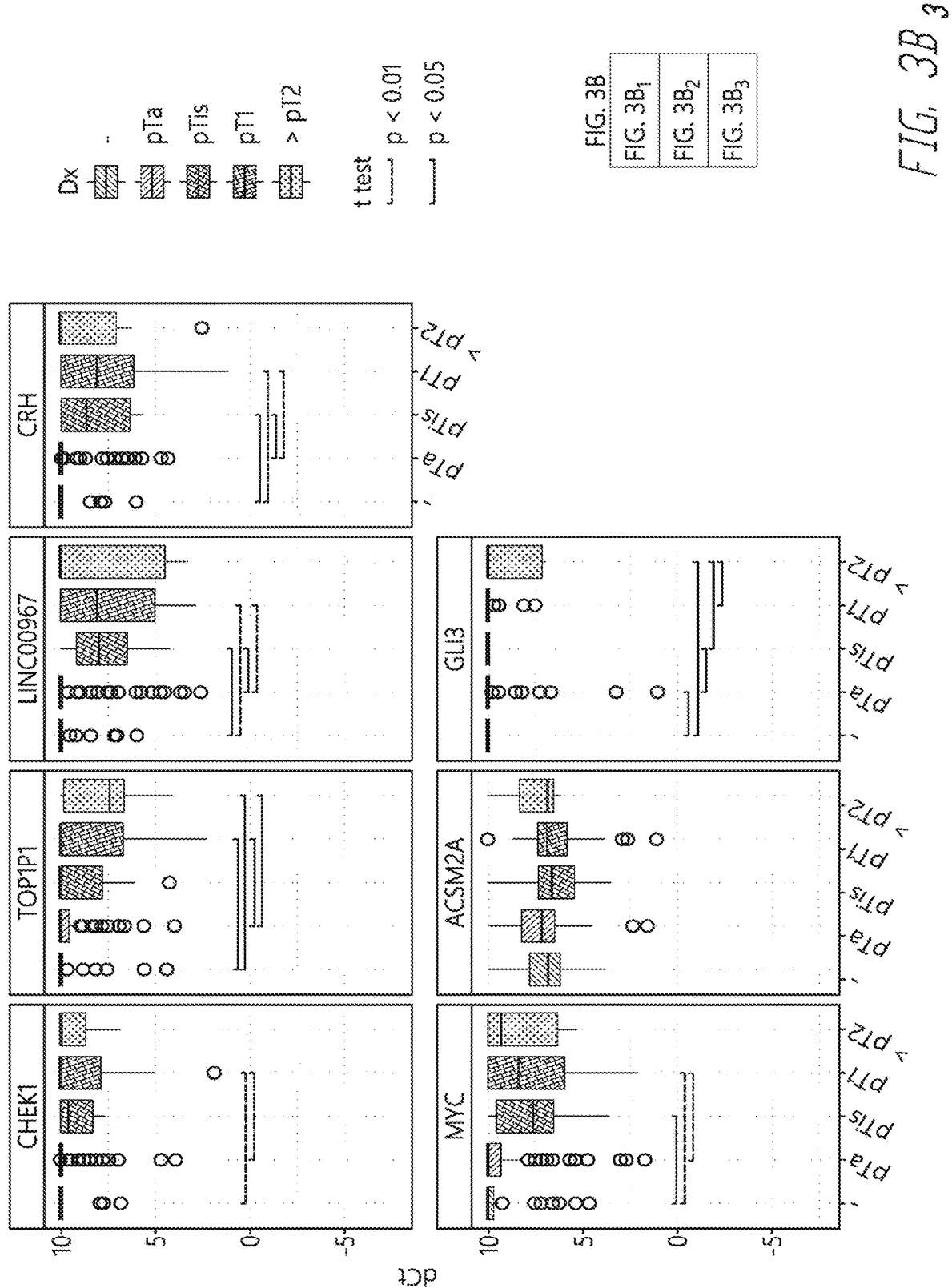
FIG. 3B₃

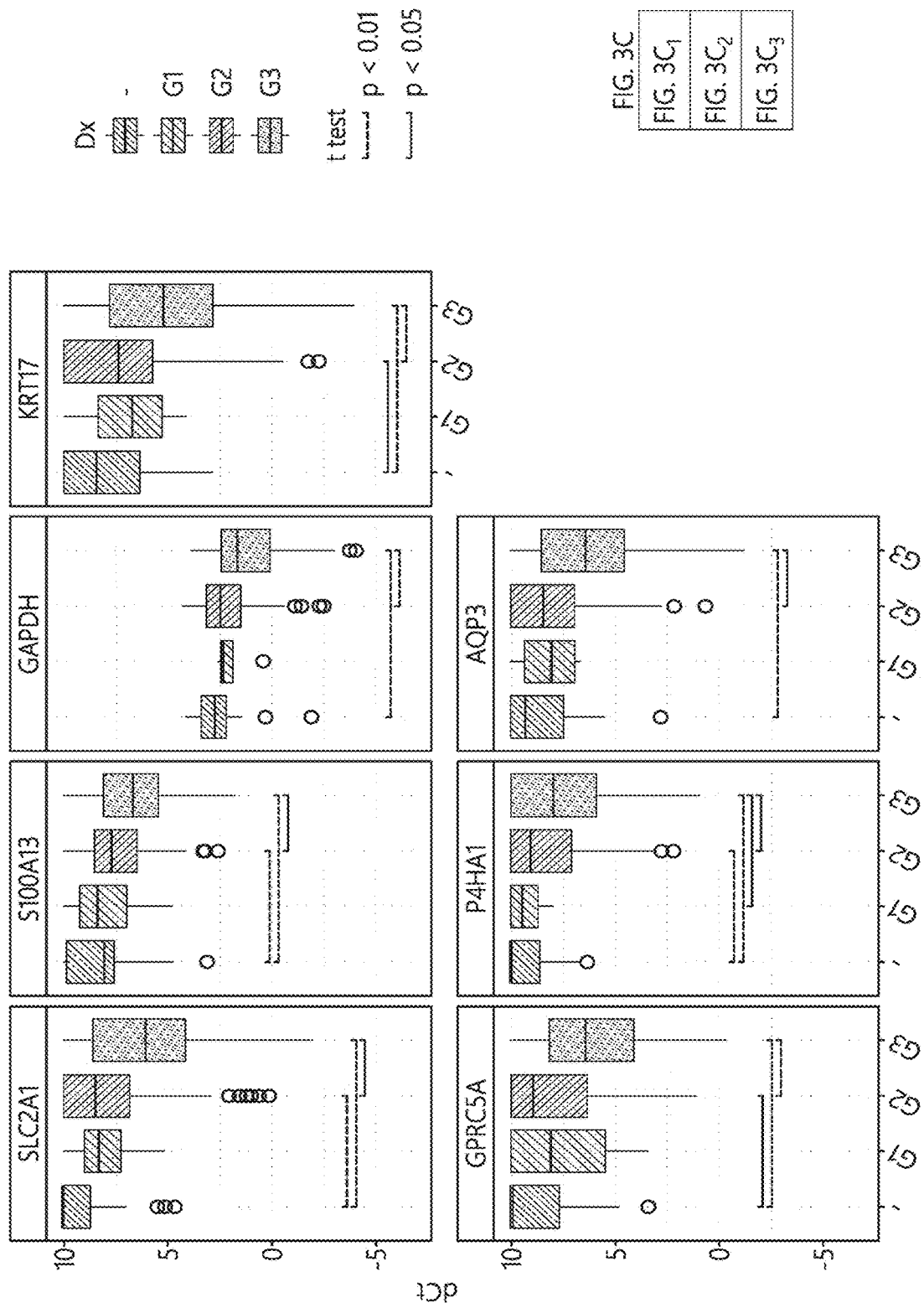

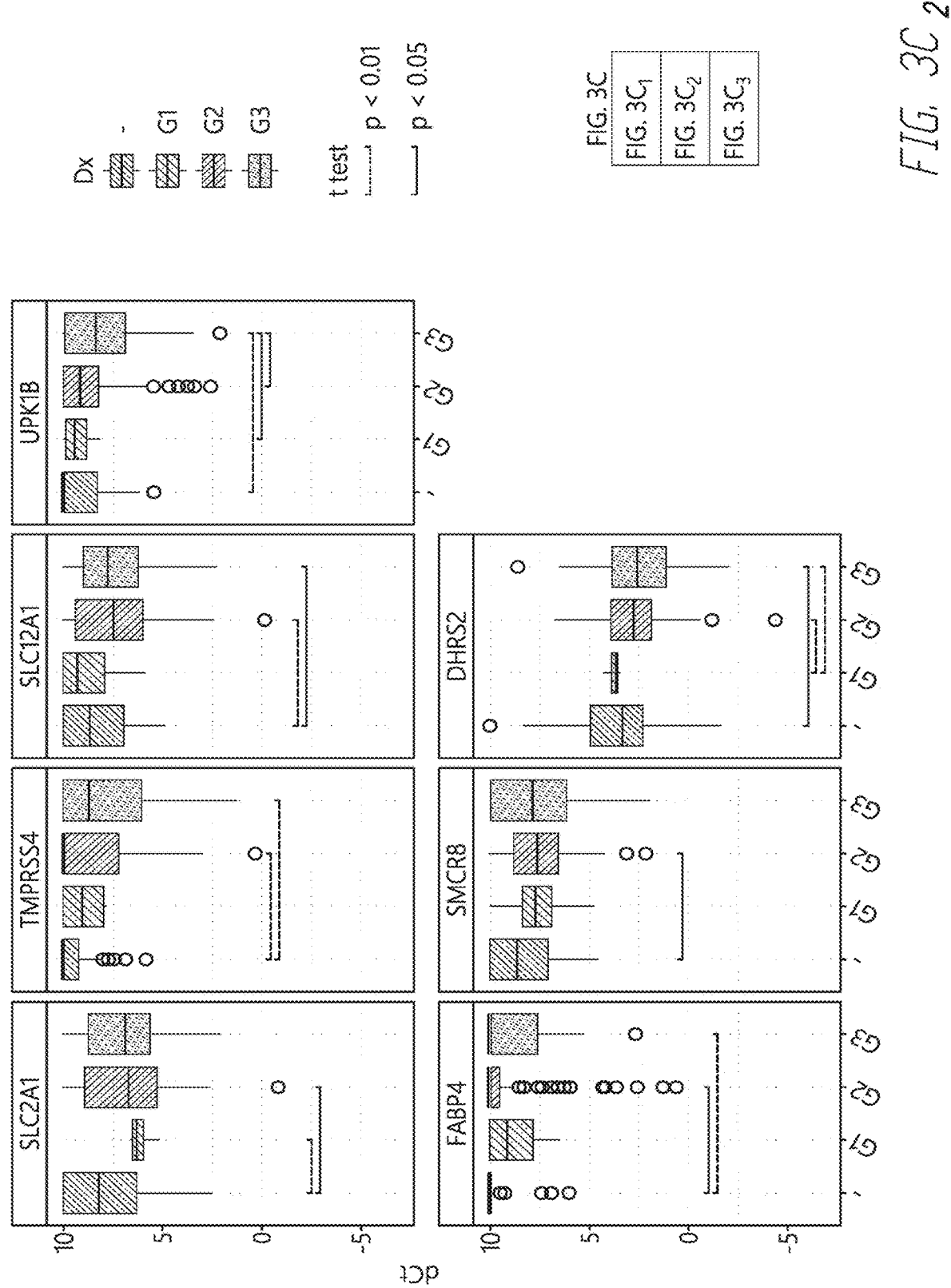
FIG. 3C_2

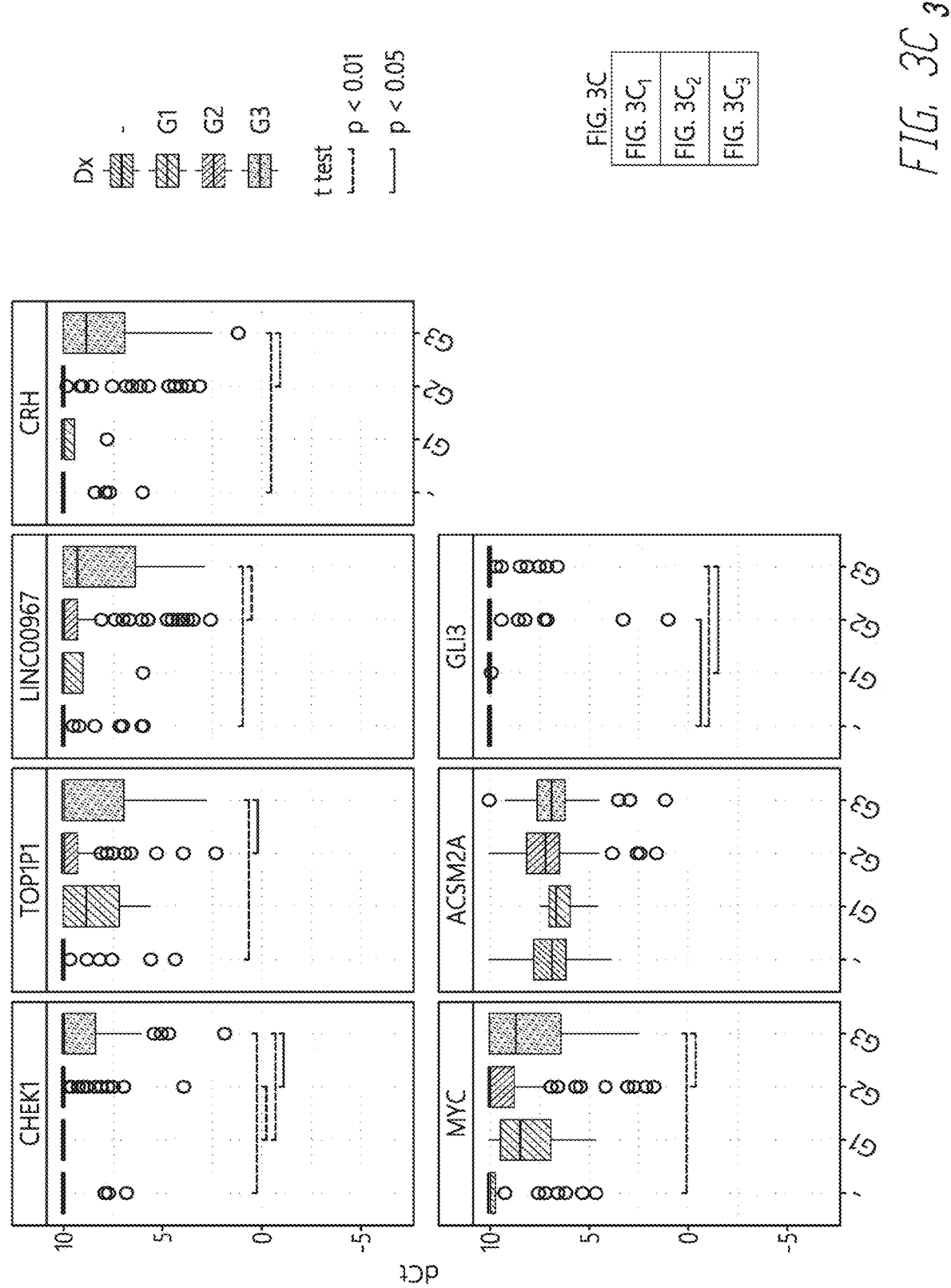
FIG. 3C₃

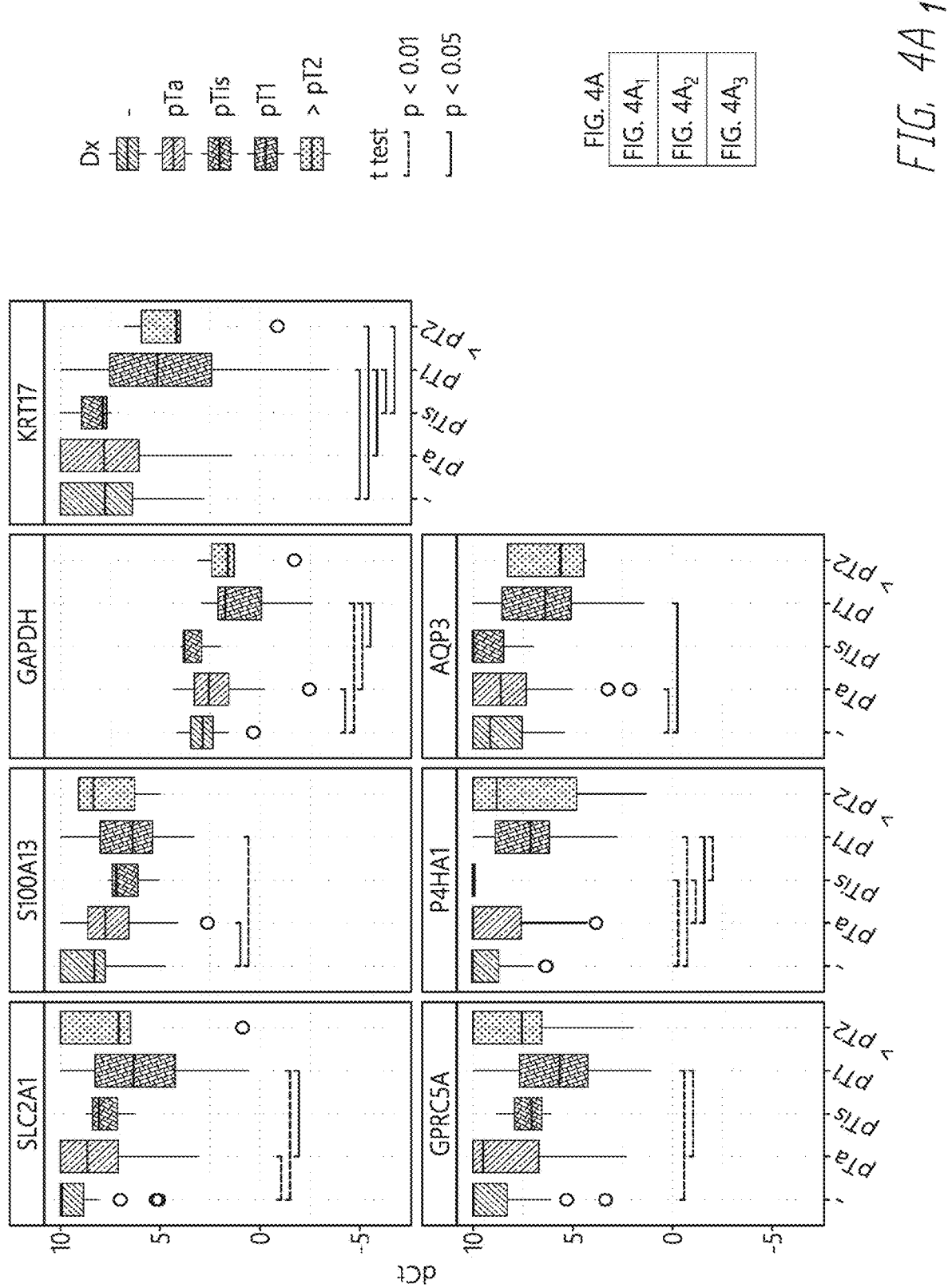
FIG. 4A₁

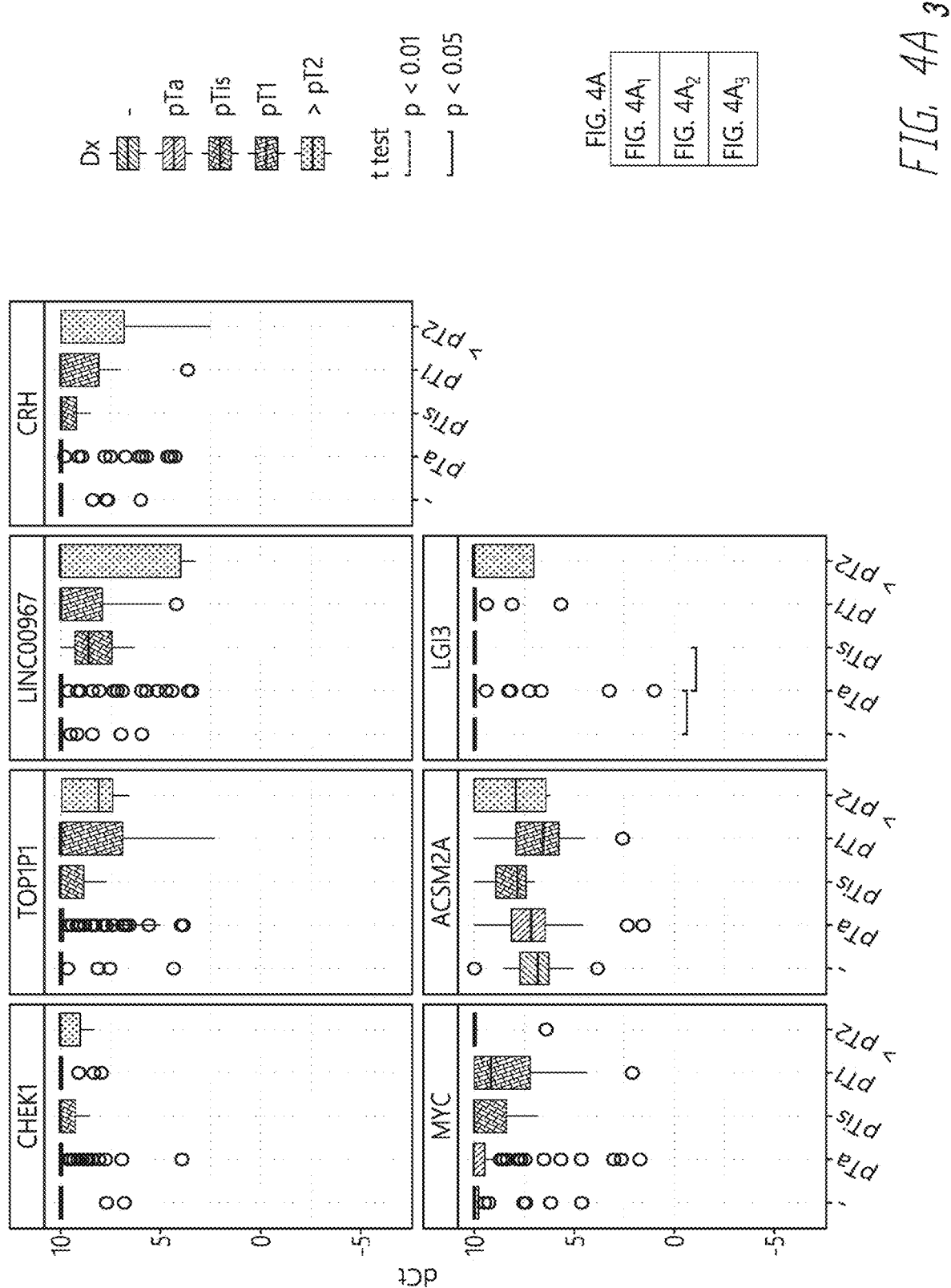
FIG. 4A₃

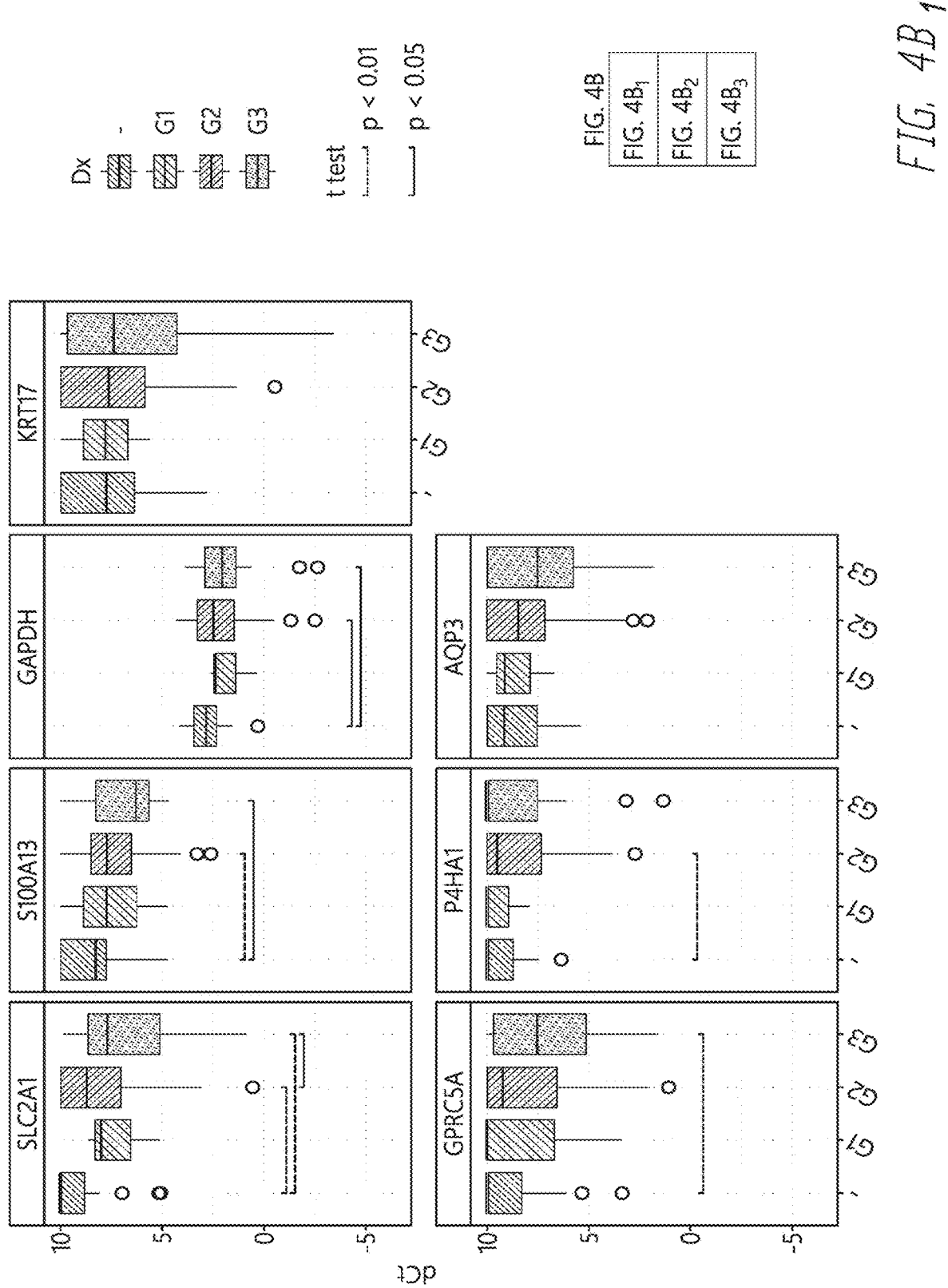
FIG. 4B1

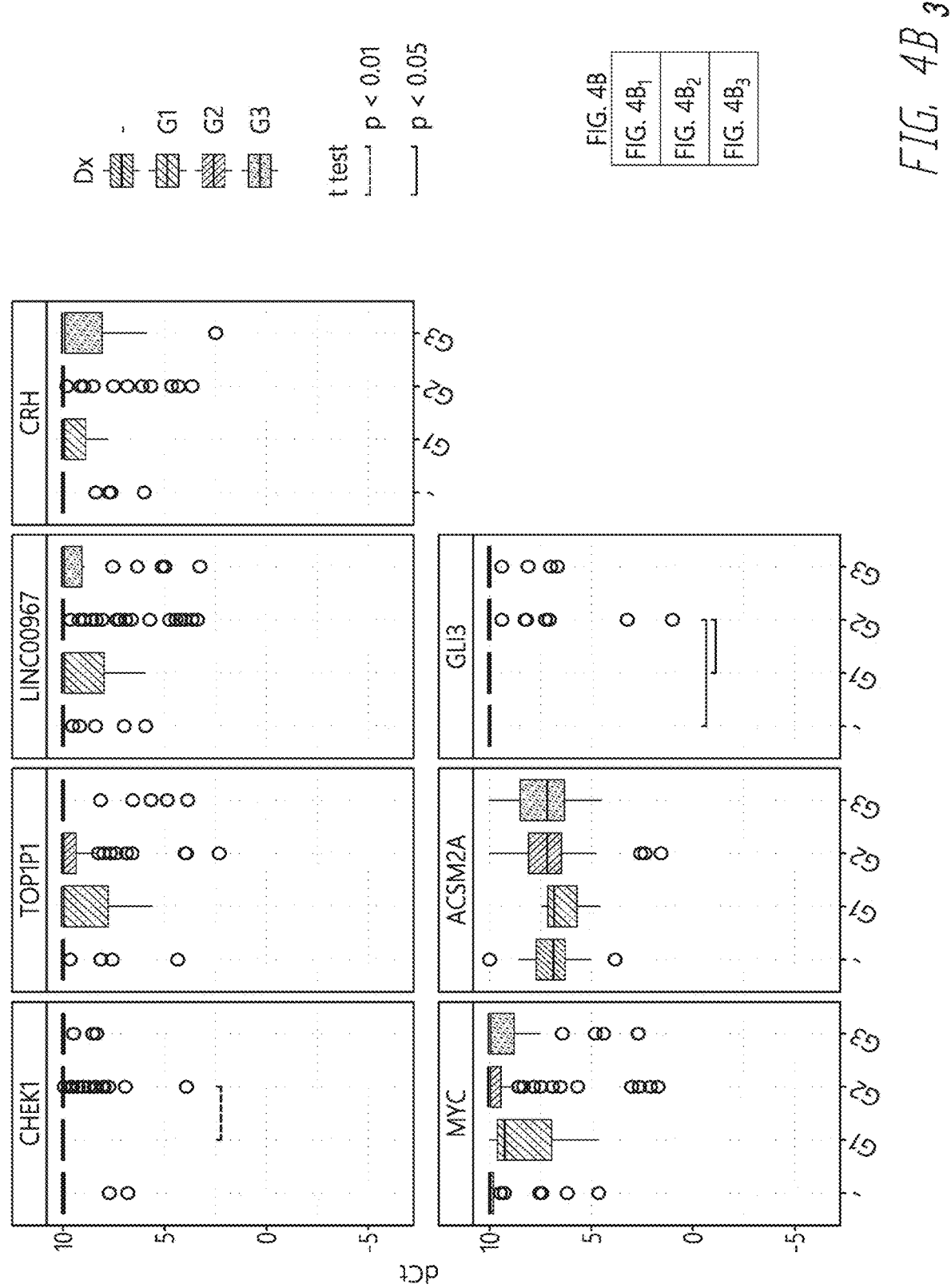
FIG. 4B₃

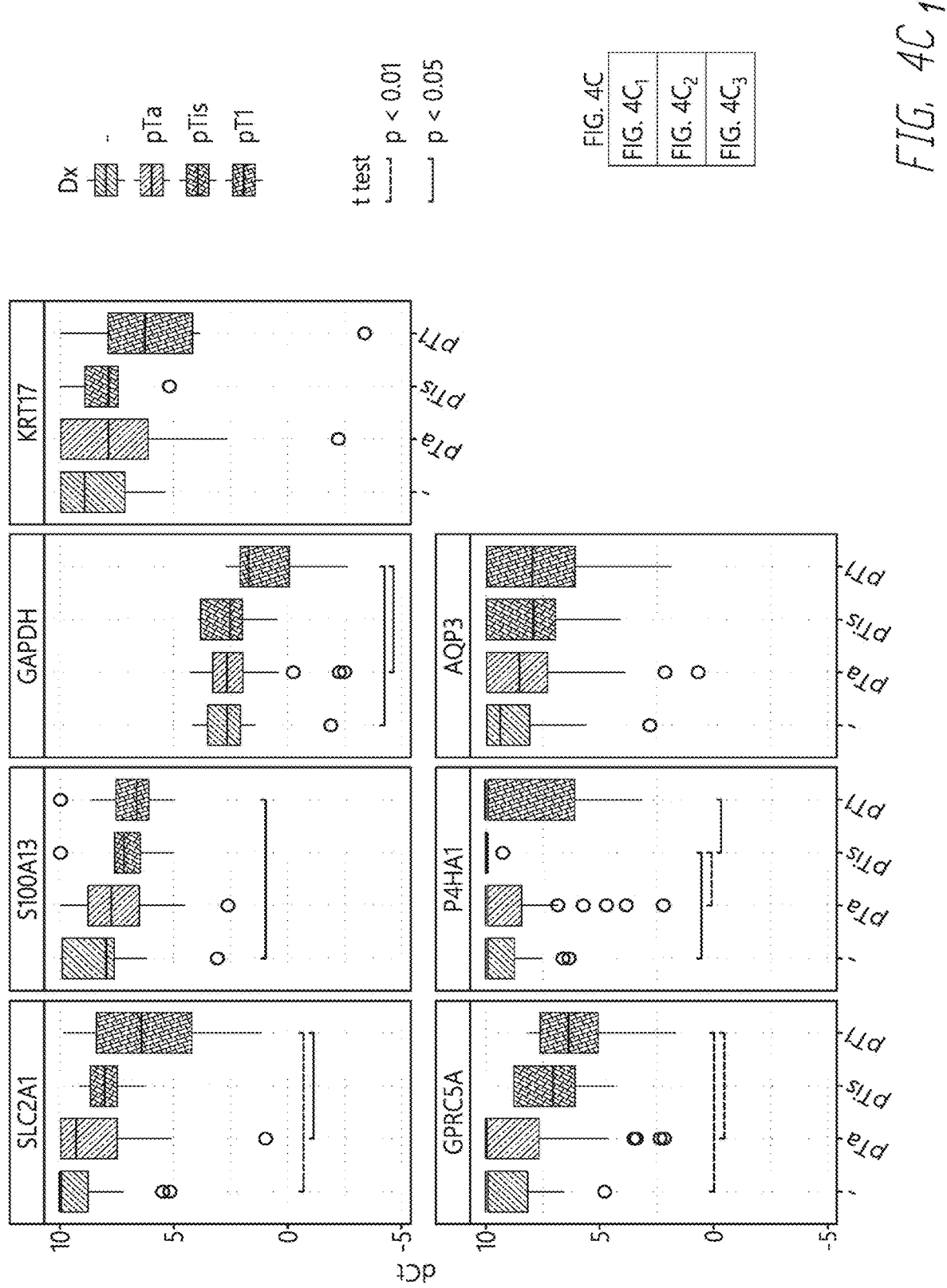
FIG. 4C₁

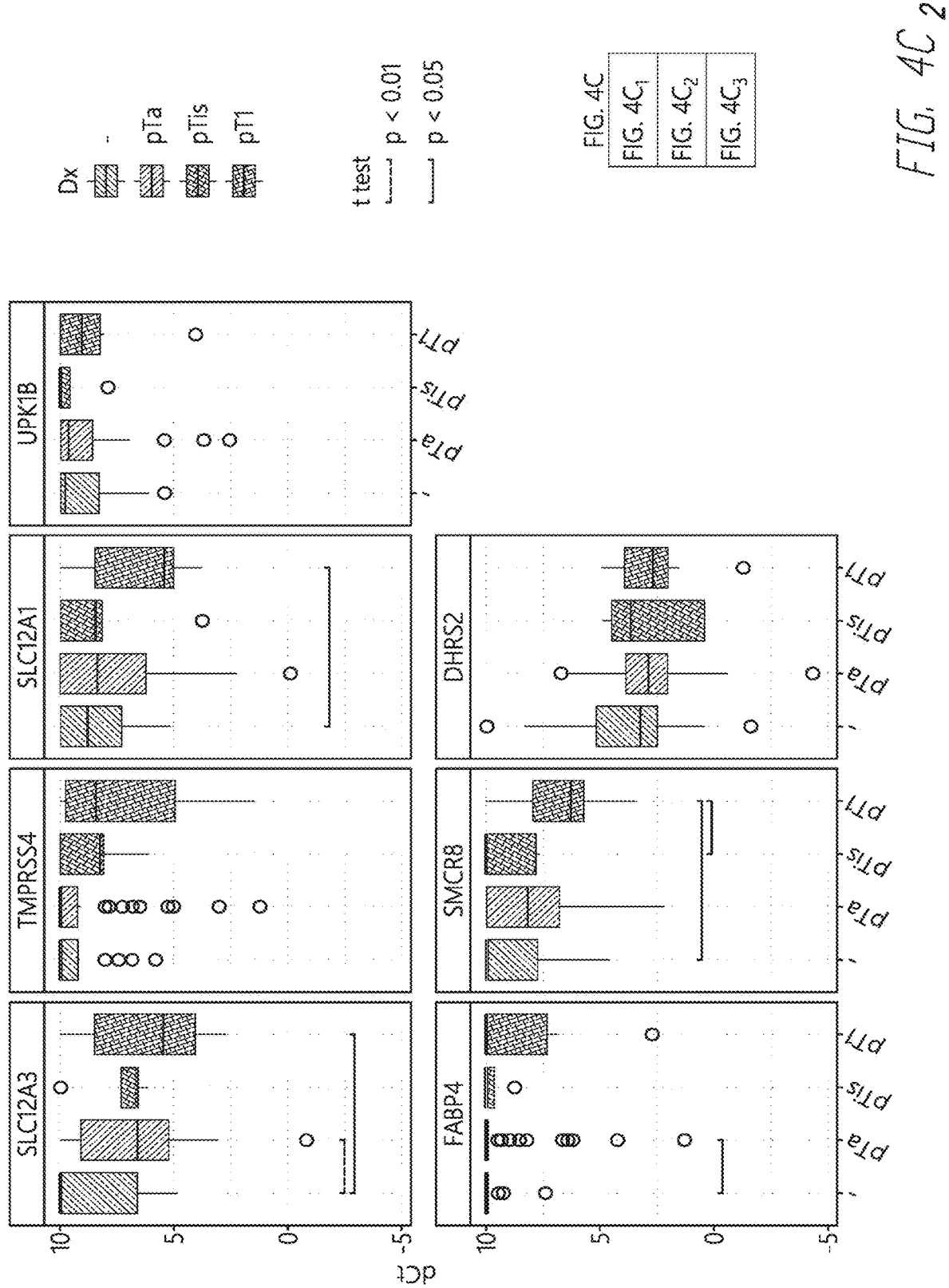
FIG. 4C2

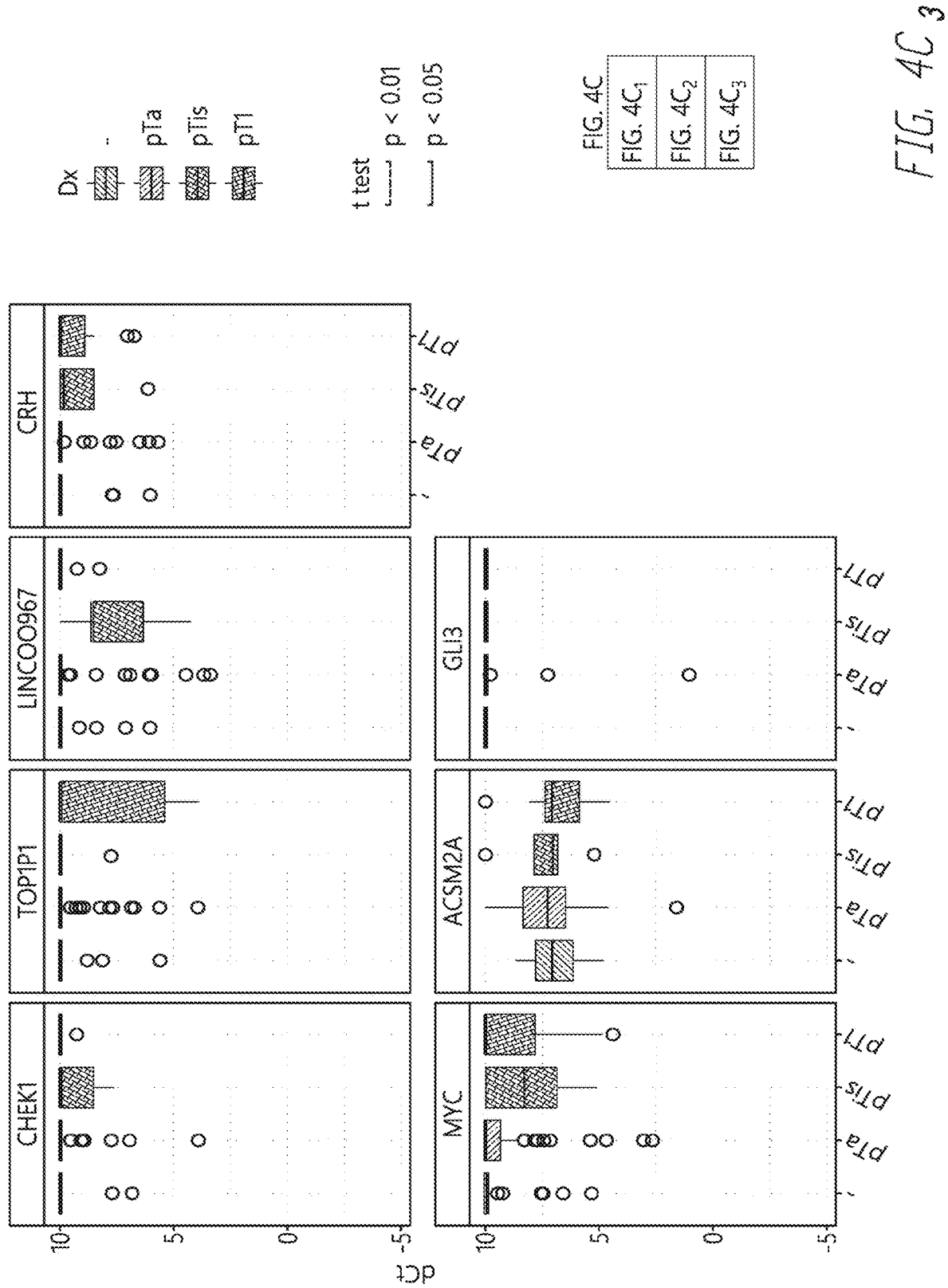
FIG. 4C₃

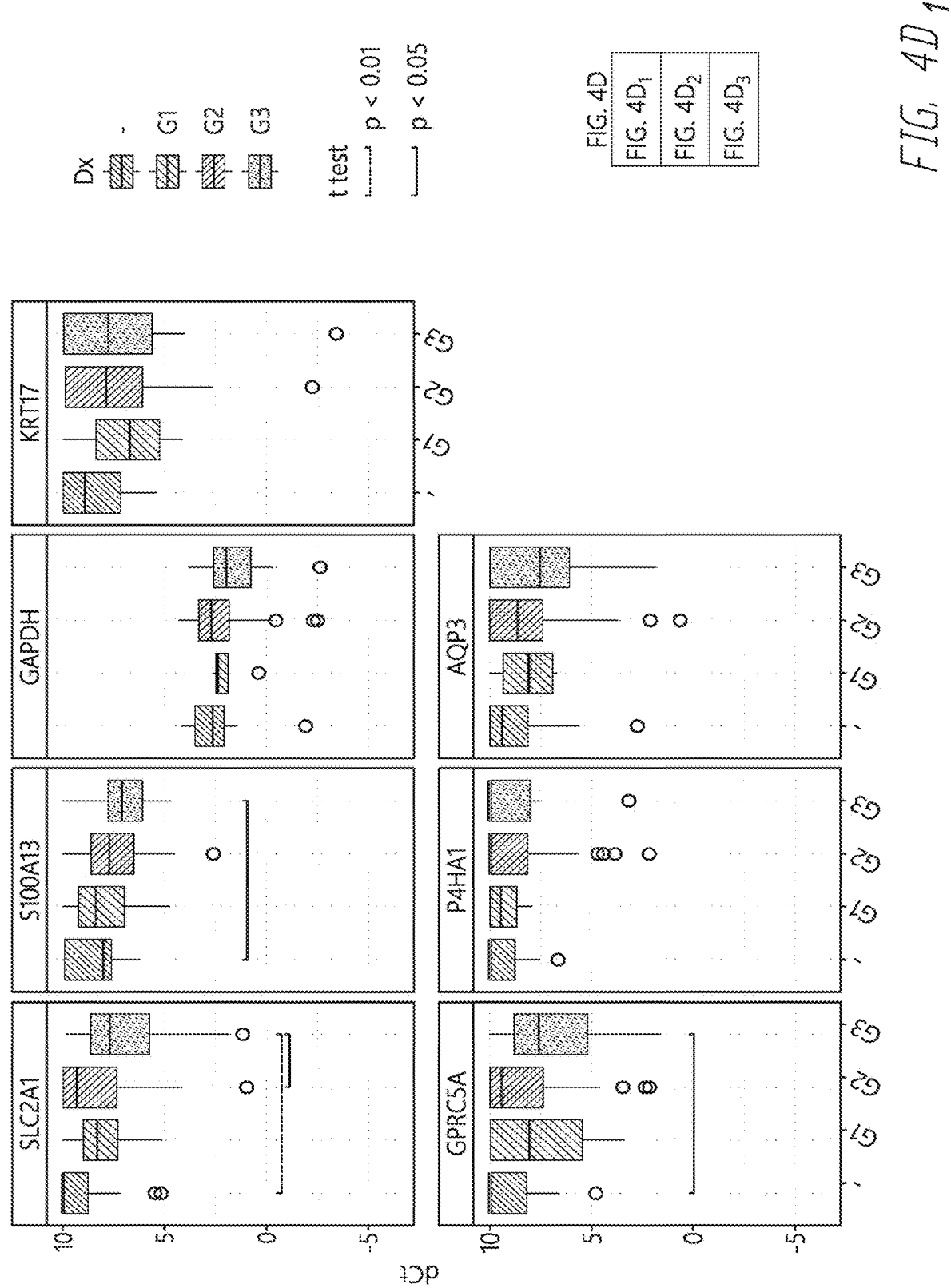
FIG. 4D₁

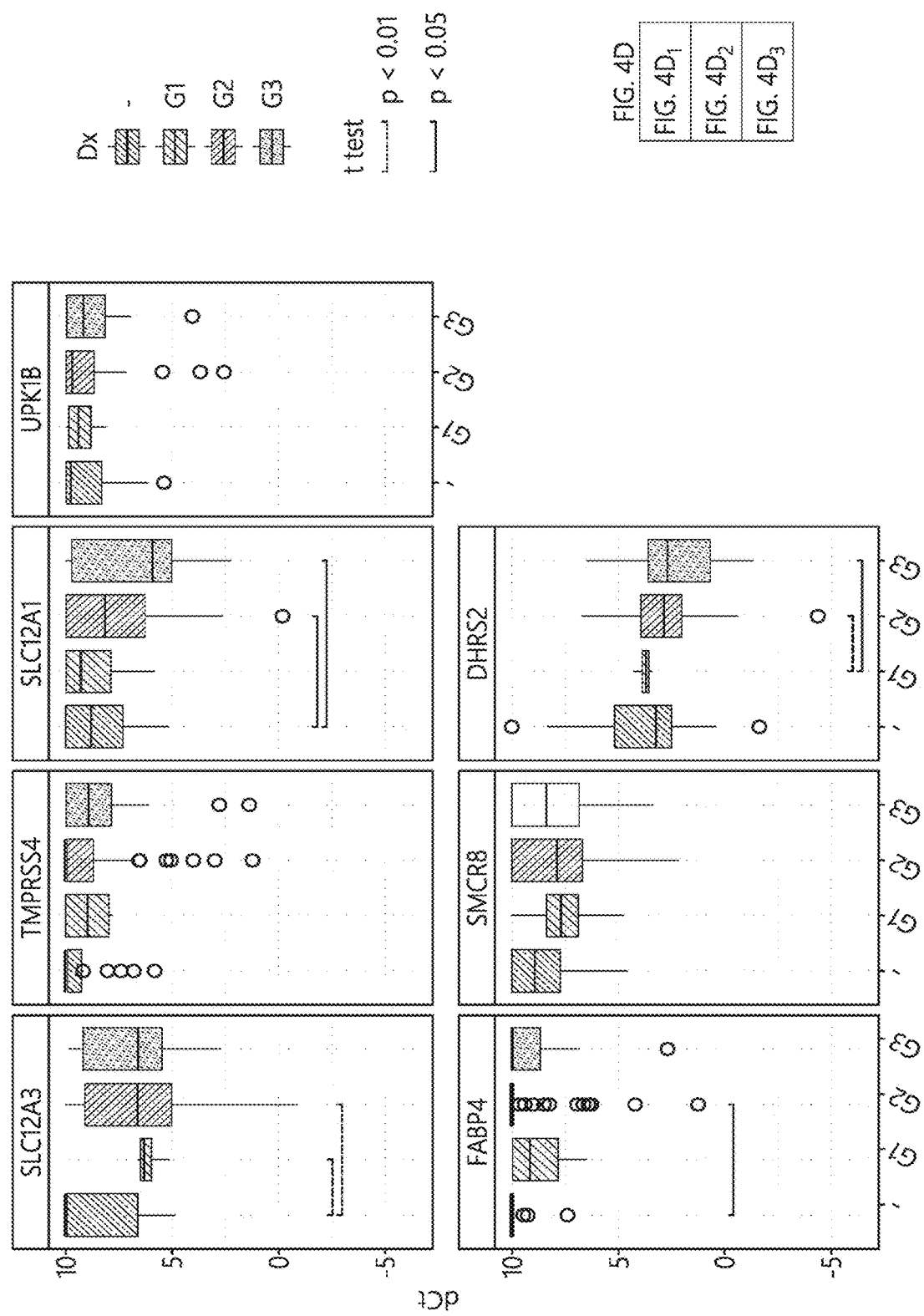
FIG. 4D2

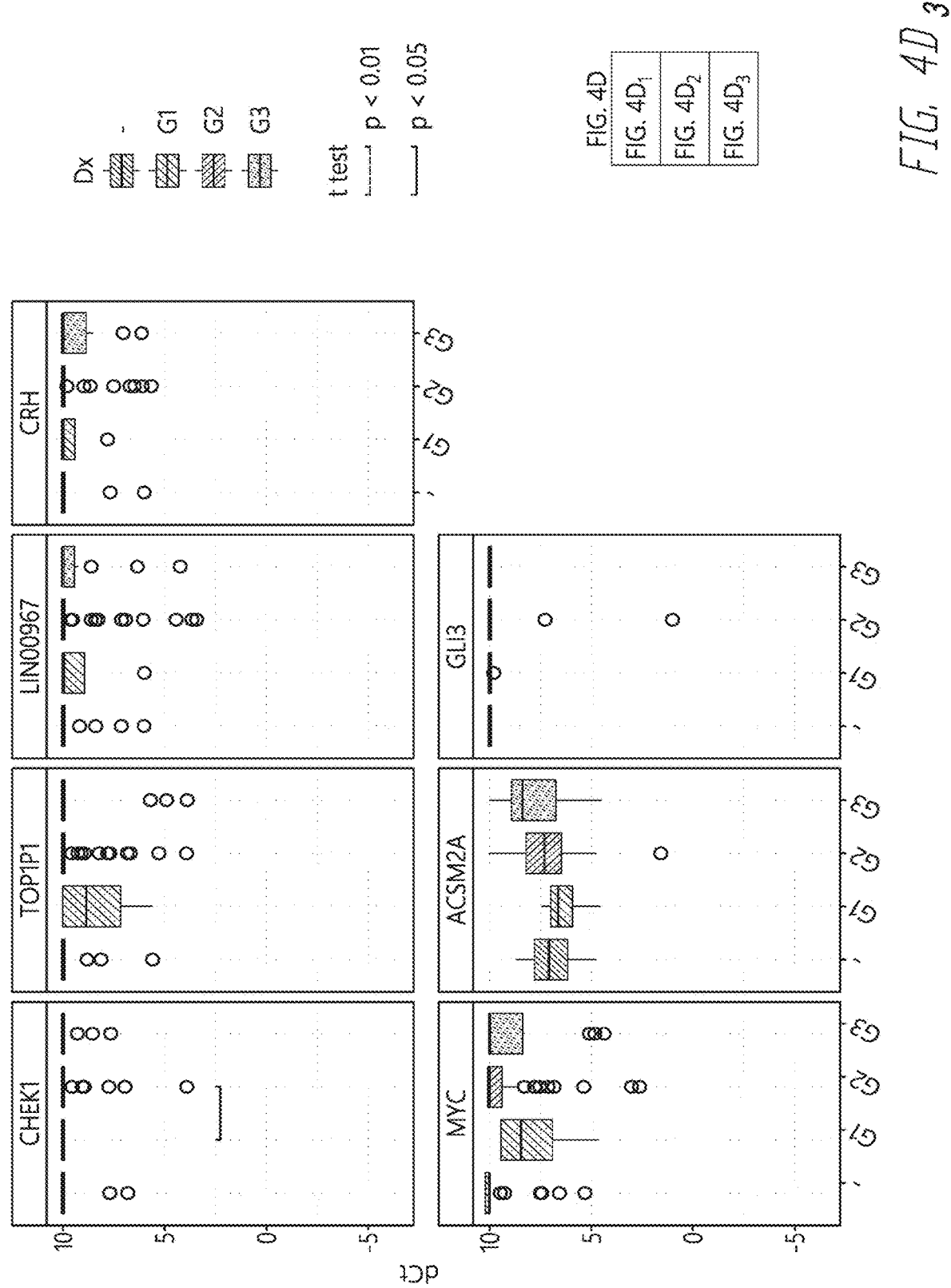
FIG. 4D₃

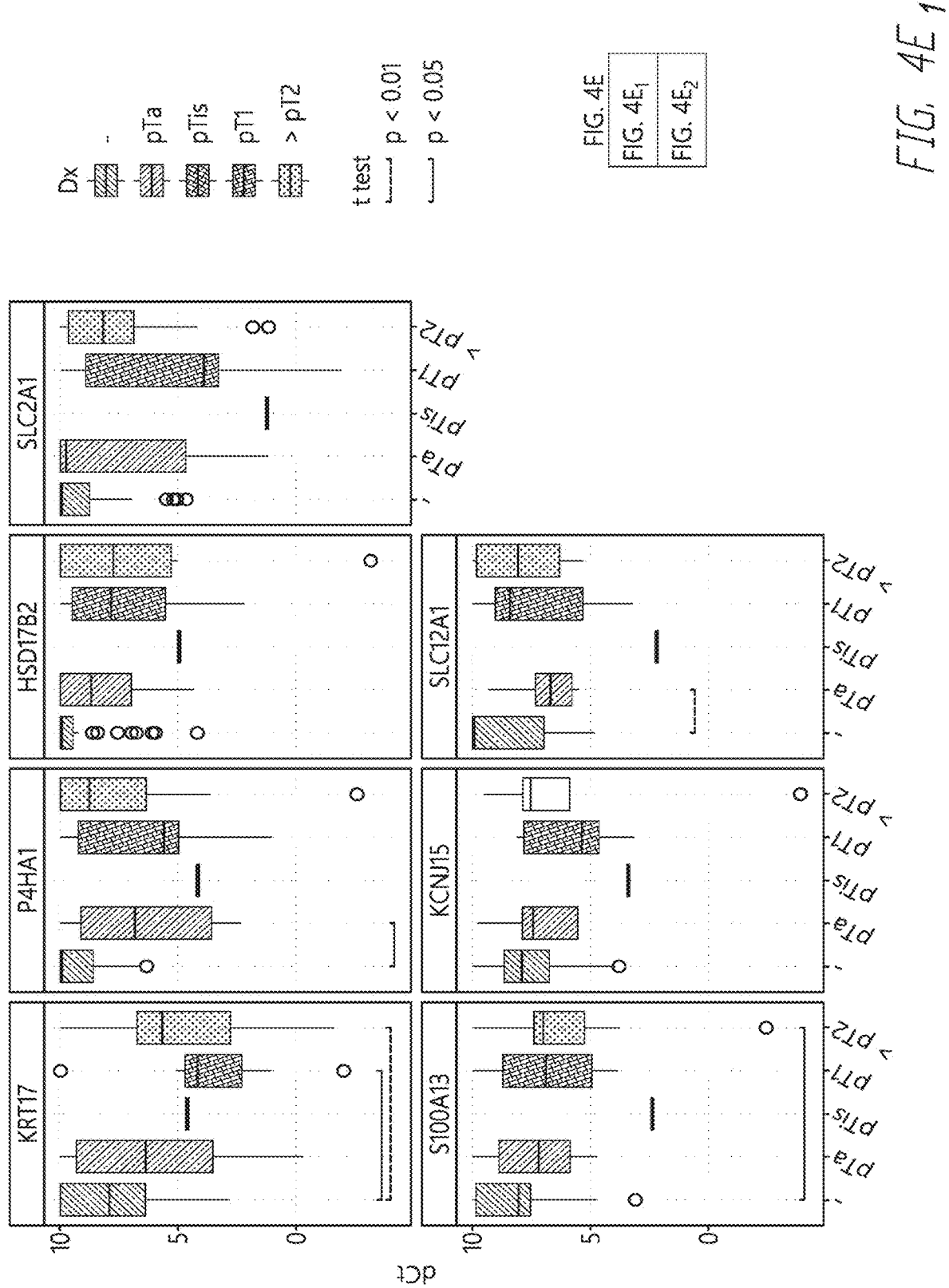
FIG. 4E_1

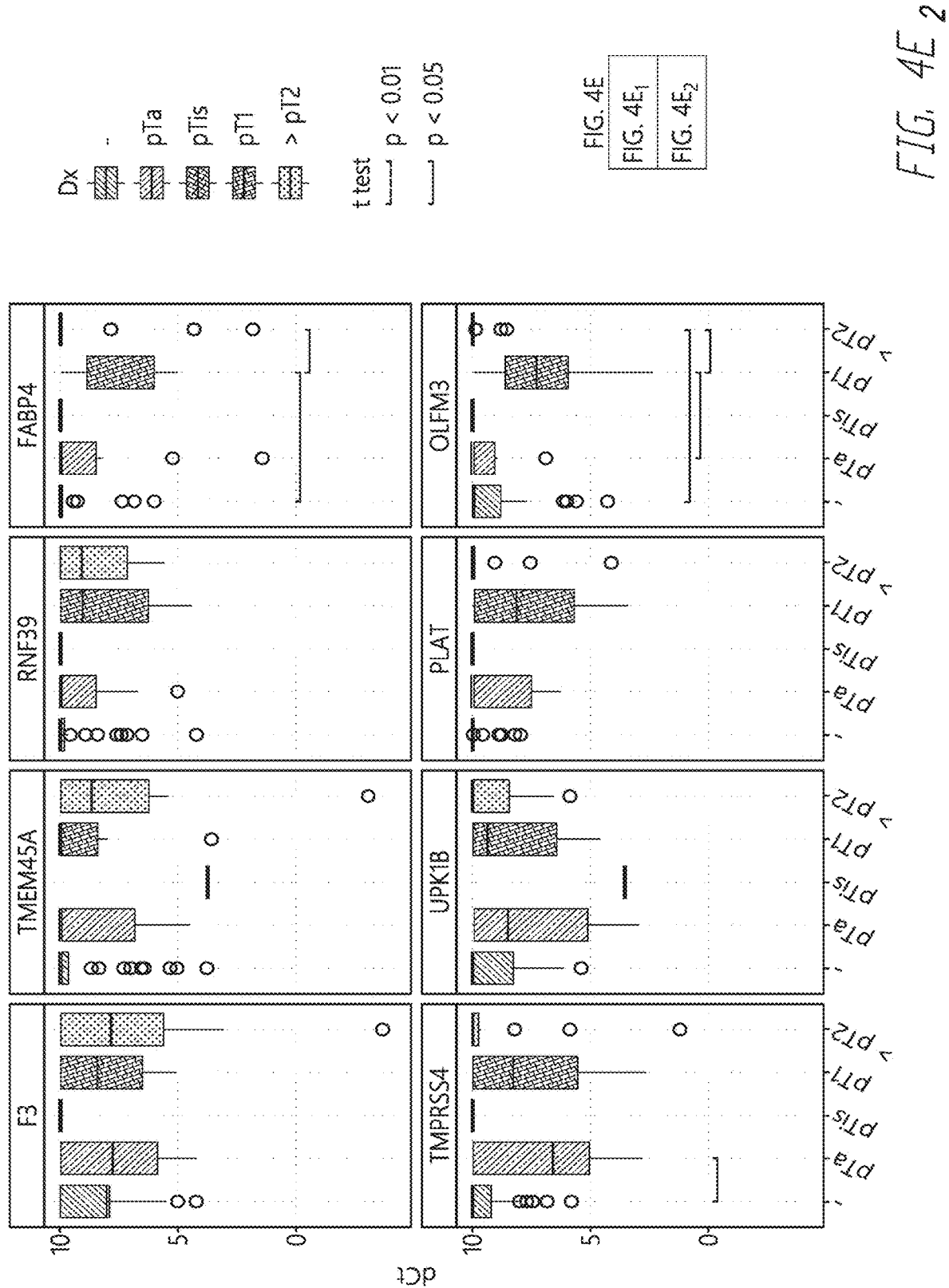
FIG. 4E₂

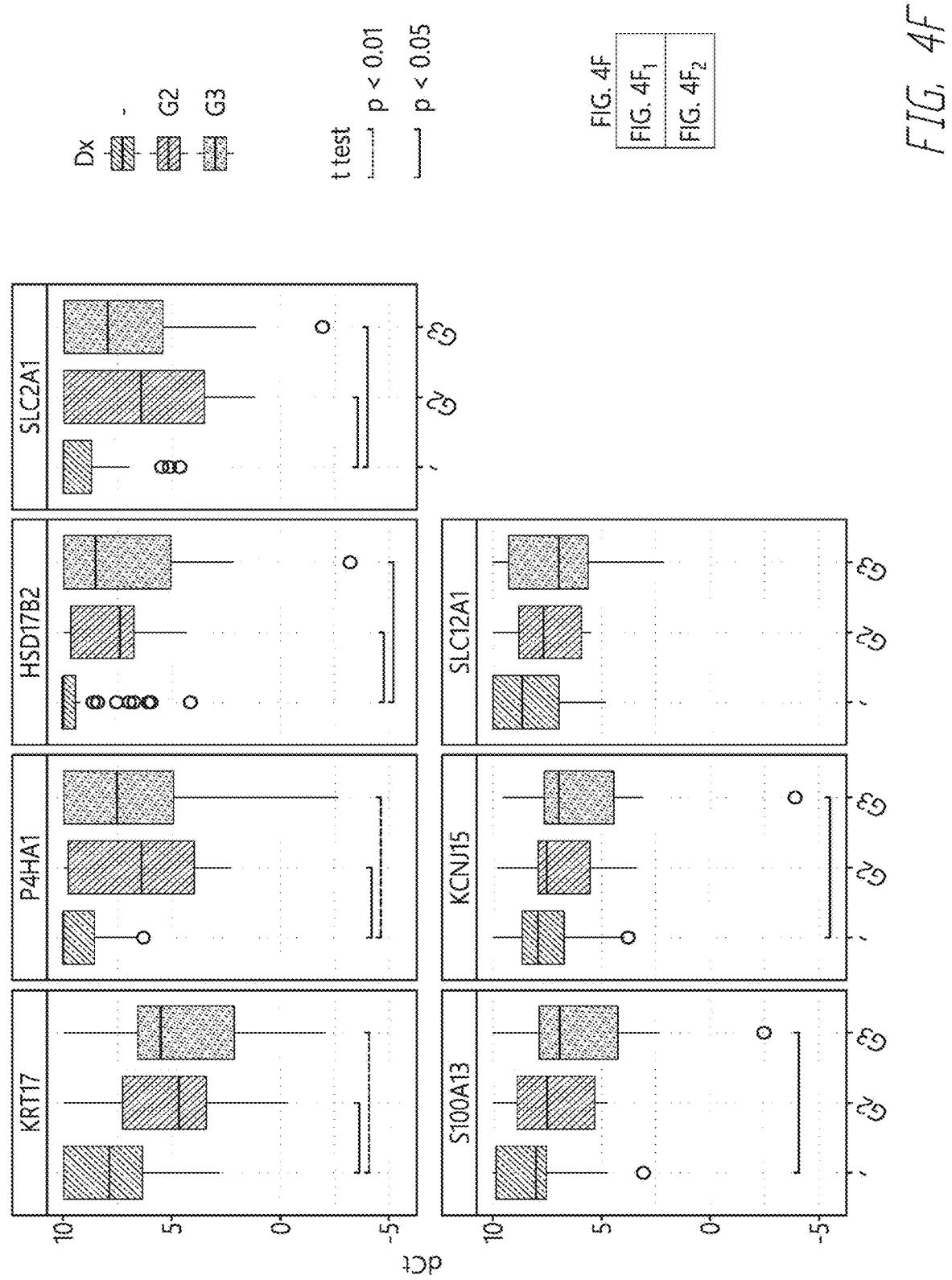
FIG. 4F₁

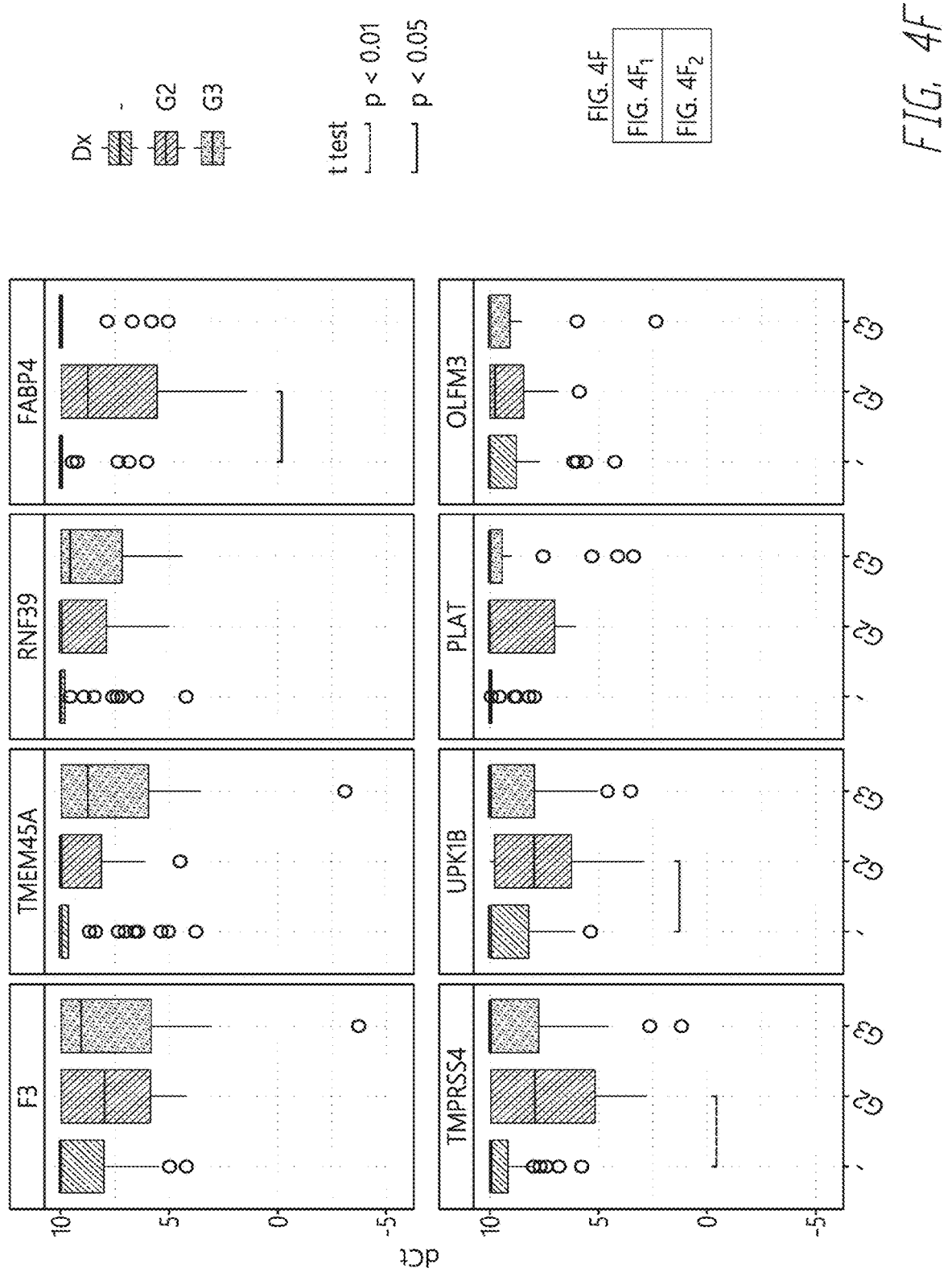
FIG. 4F₂

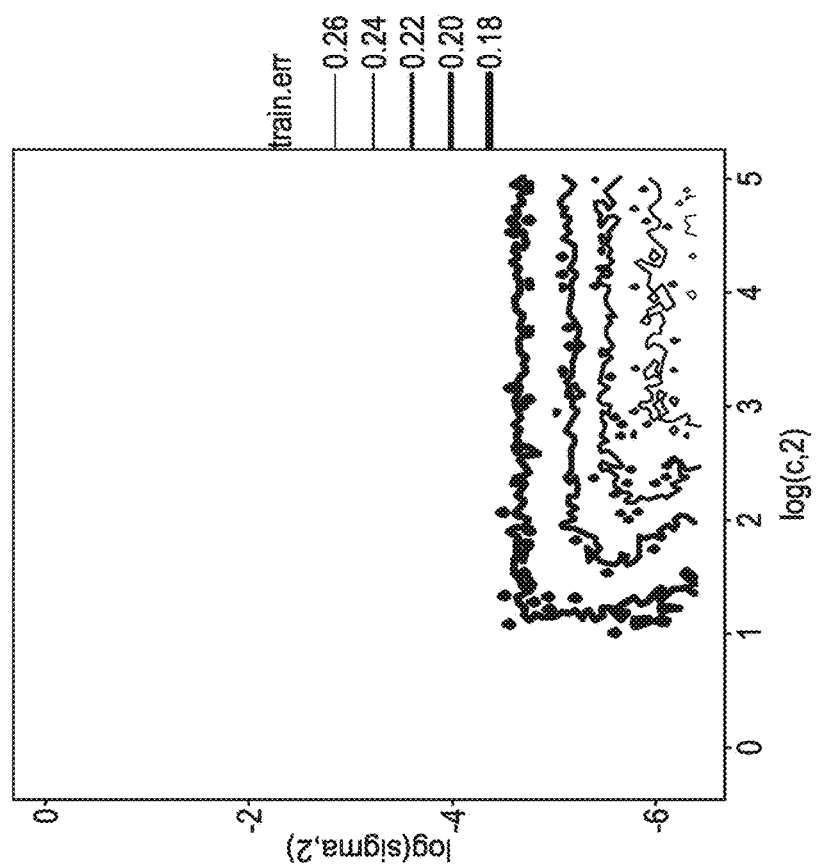
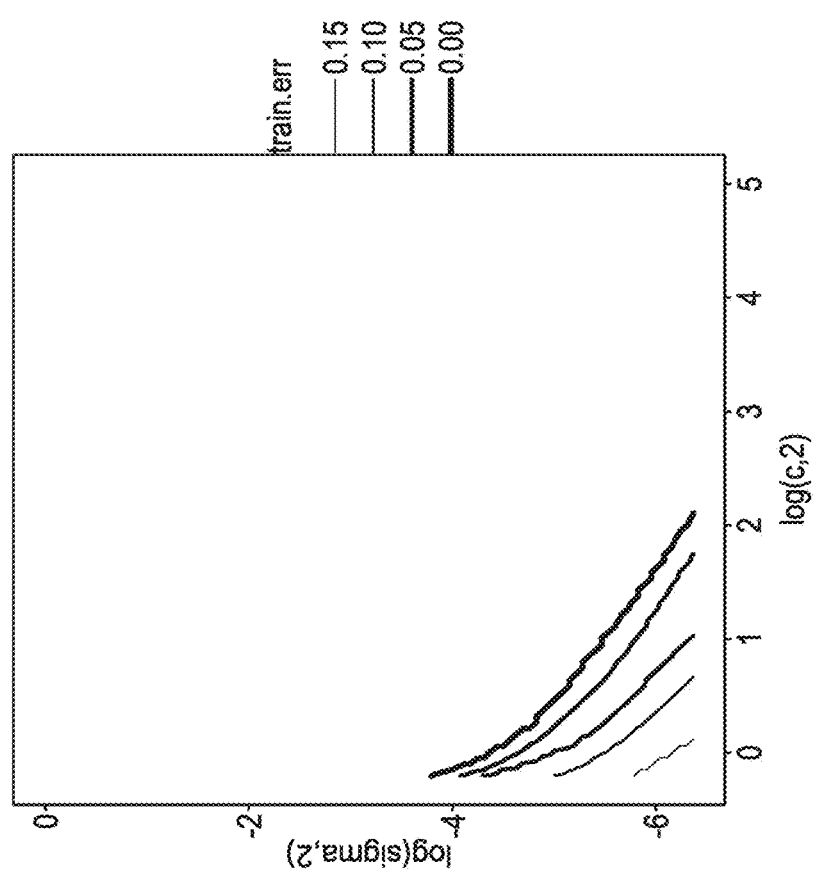
FIG. 6B

… (1)

MOLECULAR METHODS FOR ASSESSING UROTHELIAL DISEASE

INCORPORATION BY REFERENCE TO ANY PRIORITY APPLICATIONS

Any and all applications for which a foreign or domestic priority claim is identified in the Application Data Sheet as filed with the present application are hereby incorporated by reference herein and made part of the present disclosure.

REFERENCE TO SEQUENCE LISTING

A Sequence Listing submitted as an ASCII text file via EFS-Web is hereby incorporated by reference in accordance with 37 C.F.R. § 1.52(e). The name of the ASCII text file for the Sequence Listing is SEQUENCE_LISTING_HITACHI-127WO, the date of creation of the ASCII text file is Nov. 7, 2016, and the size of the ASCII text file is 16.8 KB.

BACKGROUND

Field

Several embodiments of the present disclosure relate to devices and methods structured to isolate biomarkers from body fluids and methods of using the expression profiles of such biomarkers for diagnosis and treatment of diseases. Several embodiments relate to characterizing mRNA profiles of exosomes and microvesicles from urine samples of a patient to assess, diagnose, or otherwise determine that patient's status with regard to urothelial cancer, with several embodiments related to carrying out a treatment.

Description of the Related Art

In 2015, National Cancer Institute estimated that there will be approximately 74,000 new bladder cancer cases and 14,000 deaths in the United States alone. The majority of bladder cancers and other urothelial cancers (e.g., malignancy in ureters and renal pelvises) are initiated from the transitional epithelium of urinary tract. While urothelial cancers other than bladder cancer account for only 5 to 10% of urothelial cancers, these cancers increase the chance of bladder cancer in the future.

Treatment of urothelial cancer (e.g., bladder cancer) depends on the stage and grade of the cancer. Non-muscle-invasive cancers (Ta, Tis and T1) can be treated by transurethral tumor removal or intravesical chemotherapy. On the other hand, muscle-invasive cancers (T2, T3 and T4) require more aggressive treatments such as cystectomy and intravenous chemotherapy. Because the recurrence rate for the non-muscle-invasive cancers is 50 to 70%, and even higher for the muscle-invasive cancers, the patients with bladder cancer history require lifelong monitoring of recurrence, making bladder cancer the most expensive cancer in the U.S. from diagnosis to treatment. Furthermore, about 30% of patients with ureter or renal pelvis cancer will develop a bladder cancer after a few years.

The current gold standard of bladder cancer detection is cystoscopy with urine cytology. While cystoscopy with urine cytology has a specificity of about 96%, the sensitivity is only about 44%. For low-grade tumors, the sensitivity of cystoscopy with urine cytology is even lower (4 to 31%). Cystoscopy is an invasive procedure that involves inserting a thin tube with a camera and light into the urethra and advancing the tube to the bladder.

Several FDA-approved test kits are available to screen for urine-based urothelial cancer markers (e.g., BTA stat/BTA trak (Polymedoco, New York), NMP22 BladderChek (Alere, Florida), ImmunoCyt/uCyt+ (Scimedx, New Jersey), UroVysion (Abbott Molecular, Illinois)). These diagnostic kits show very similar sensitivity and specificity to the current gold standard, cystoscopy and cytology. Therefore, better non-invasive biomarkers are still needed, especially ones with higher sensitivity.

SUMMARY

As discussed, the current gold standard diagnostic method of urothelial cancers including bladder, ureter and renal pelvis cancers is cystoscopy and urine cytology. Considering the invasiveness and diagnostic performance of the method as well as the highly recurrent nature of urothelial cancers (e.g., bladder cancer), there is a need to identify new non-invasive biomarkers having higher sensitivity. There are provided herein, in several embodiments, methods and systems for diagnosing and assessing urothelial cancer with high specificity and sensitivity. In several embodiments, the methods are minimally invasive. In several embodiments, the methods are computer-based, and allow an essentially real-time assessment of the presence and/or status of urothelial cancer. In several embodiments, a specific recommended treatment paradigm is produced (e.g., for a medical professional to act on).

In certain aspects, various RNA can be used in the methods, including, but not limited to detecting the presence of a urothelial cancer in a subject. In some embodiments, the method includes obtaining a urine sample from the subject; preparing a urine supernatant by removing cells and large debris from the urine sample; isolating urinary exosomes and microvesicles from the urine supernatant; isolating an RNA from the urinary exosomes and microvesicles; quantifying an expression level of a marker selected from the group consisting of SLC2A1, S100A13, GAPDH, KRT17, GPRC5A, P4HA1, and HSD17B2; and identifying the subject as having the urothelial cancer if the expression level is higher than an expression level of the mRNA in a urine sample obtained from a non-urothelial cancer subject. In certain variants, the method further includes detecting a reference gene wherein a said reference gene is used to normalize said expression level of said marker wherein the reference gene is selected from the group consisting of ACTB, GAPDH, ALDOB, DHRS2 and UPK1A. In some embodiments, the marker is selected from the list consisting of SLC2A1, S100A13, GAPDH, KRT17 and GPRC5A. In certain embodiments, a value of a diagnostic formula is obtained by machine learning technique such as logistic regression analysis and support vector machine using the expression level of more than one of the said marker. In some embodiments, the urothelial cancer to be detected is selected from the group consisting of bladder cancer, renal pelvis cancer, and ureter cancer. In some aspects, the urothelial cancer to be detected is recurrent bladder cancer. In certain variants, the subject does not show a urine cytology positive result.

In some aspects, a method is disclosed for screening a human subject for an expression of an RNA associated with a urothelial cancer, the method including the steps of comparing an expression of the RNA in a vesicle isolated from a urine sample from the subject with an expression of said RNA in a vesicle isolated from a urine sample of a healthy donor, wherein an increase in said expression of said RNA of said subject compared to said expression of said RNA of said donor indicates said subject has urothelial cancer when said increase is beyond a threshold level, wherein said comparing the expression of the RNA in the vesicle isolated from the urine sample further comprises: capturing the vesicle from the sample from the subject by moving the sample from the subject across a vesicle-capturing filter; loading a lysis buffer onto the vesicle-capturing filter, thereby lysing the vesicle to release a vesicle-associated RNA, and quantifying the expression of the RNA associated with urothelial cancer in the vesicle-associated RNA by PCR. In some variants, comparing further comprises: determining a value of a diagnostic formula from the expression of the RNA isolated from the subject, wherein the diagnostic formula is a linear or non-linear mathematical formula, wherein the RNA is 1 gene to 60 genes, more preferably 2 genes to 10 genes. In some aspects, the RNA is selected from the group consisting of KRT17, SLC2A1, ALDOB, LINC00967, SLC16A9, CRH, PCAT4, AQP3, THAP7, FADS2, SERPINE1, AS1, OLFM3, S100A13, C5orf30, GINM1, GPRC5A and TOP1P1. In at least one embodiment, the RNA is selected from the group consisting of ALDOB, CRH, SERPINE1 and SLC2A1.

The methods summarized above and set forth in further detail below describe certain actions taken by a practitioner; however, it should be understood that they can also include the instruction of those actions by another party. Thus, actions such as "treating a subject for a disease or condition" include "instructing the administration of treatment of a subject for a disease or condition."

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

FIG. 2D shows box-and-whisker plots of raw Ct values in the RT-qPCR assay of different urinary EMV mRNA in different cancer types.

FIG. 2F shows box-and-whisker plots of raw Ct values in the RT-qPCR assay of different urinary EMV mRNA in different bladder cancer grades.

FIG. 3A shows box-and-whisker plots of RT-qPCR assay Ct values normalized by ALDOB using delta Ct method. Normalized Ct values are shown for different urinary EMV mRNA in different cancer types.

FIG. 3B shows box-and-whisker plots of RT-qPCR assay Ct values normalized by ALDOB using delta Ct method. Normalized Ct values are shown for different urinary EMV mRNA in different bladder cancer stages.

FIG. 3C shows box-and-whisker plots of RT-qPCR assay Ct values normalized by ALDOB using delta Ct method. Normalized Ct values are shown for different urinary EMV mRNA in different bladder cancer grades.

FIG. 4C depicts gene expression of urinary EMV mRNA candidates for different stages of recurrent bladder cancer.

FIG. 4D depicts gene expression of urinary EMV mRNA candidates for different grades of recurrent bladder cancer.

FIG. 4E depicts gene expression of urinary EMV mRNA candidates for different stages of non-bladder urothelial cancer.

FIG. 4F depicts gene expression of urinary EMV mRNA candidates for different grades of non-bladder urothelial cancer.

FIG. 6B depicts parameter optimization by a grid search to obtain the best combination of parameters, c and sigma, through 10 repeats of 5-fold cross validation.

DETAILED DESCRIPTION

Figure 1A:
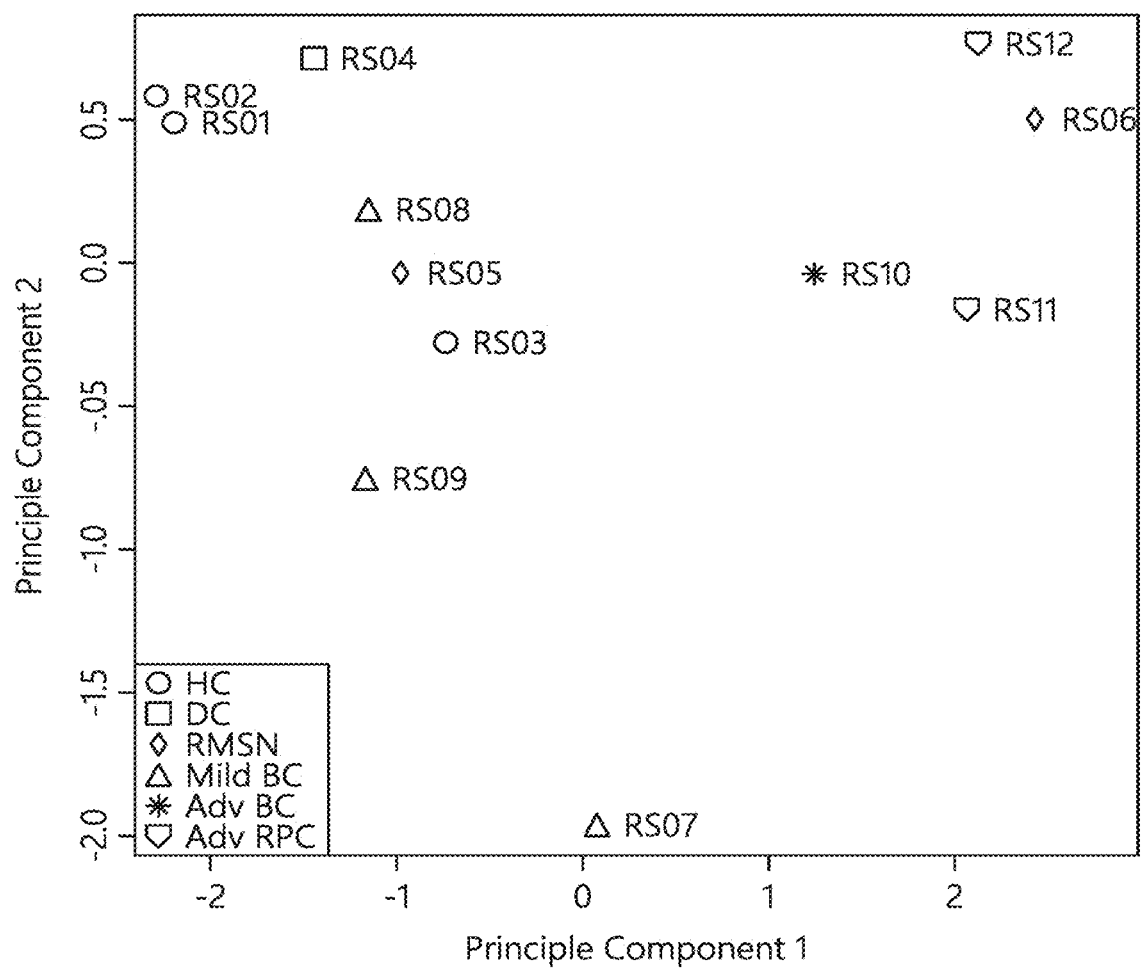
FIG. 1A depicts a clustering analysis of EMV mRNA profiles.

Certain aspects of the present disclosure are generally directed to a minimally-invasive, or non-invasive, method that assesses a patient's condition with regard to urothelial cancer. Each and every feature described herein, and each and every combination of two or more of such features, is included within the scope of the present disclosure provided that the features included in such a combination are not mutually inconsistent.

Exosomes and microvesicles (EMV) are released into the urinary space from all the areas of the nephrons and encapsulate cytoplasmic molecules of the cell of origin. Several studies showed that tumors generate larger EMV at higher concentrations. EMV from muscle-invasive bladder cancer cells have been shown to cause urothelial cells to undergo epithelial-to-mesenchymal transition. Since urothelial cancers are located on the urothelium and directly in contact with urine, EMV from urothelial cancers may be released into urine, suggesting that, according to several embodiments disclosed herein, urinary EMV could be a rich source of urothelial cancer biomarkers. Urinary cells and other markers are released from tumors into urine only after the tumor grows significantly and invades surrounding areas.

However, urinary EMV are released not only from tumors but also from normal and injured cells. Therefore, molecular signatures of urothelial cancer could be obtained in urine much earlier than the conventional biomarkers of urothelial cancer.

The standard method to isolate urinary EMV is a differential centrifugation method using ultracentrifugation. However, use of ultracentrifugation may not be applicable for routine clinical assays at regular clinical laboratories. Several embodiments of the present disclosure employ a urinary EMV mRNA assay for biomarker and clinical studies, which enables similar or even superior performances to the standard method in terms of assay sensitivity, reproducibility and ease of use. Several embodiments employ this urinary EMV mRNA assay to screen urine samples from urothelial cancer patients with various grades and stages of cancer were screened to identify new biomarkers of urothelial cancer.

As described in more detail below, urinary exosomes can be isolated from urine by passing urine samples through a vesicle capture filter, thereby allowing the EMV to be isolated from urine without the use of ultracentrifugation. In some embodiments, the vesicle capture material has a porosity that is orders of magnitude larger than the size of the captured vesicle. Although the vesicle-capture material has a pore size that is much greater than the size of the EMV, the EMV are captured on the vesicle-capture material by adsorption of the EMV to the vesicle-capture material. The pore size and structure of the vesicle-capture material is tailored to balance EMV capture with EMV recovery so that mRNA from the EMV can be recovered from the vesicle-capture material. In some embodiments, the vesicle-capture material is a multi-layered filter that includes at least two layers having different porosities. In some embodiments, the urine sample passes first through a first layer and then through a second layer, both made of glass fiber. In one embodiment, the first layer has a pore-size of 1.6 µm, and the second layer has a pore size of 0.7 µm. In some configurations, the first layer has a particle retention rate of between 0.6 and 2.7 µm, preferably 1.5 and 1.8 µm, and the second layer has a particle retention rate between 0.1 and 1.6 µm, preferably 0.6 and 0.8 µm. In one embodiment, a particle retention rate of the first layer is greater than that of the second layer, thereby higher particulate loading capacity and faster flow rates can be obtained.

Several aspects of the present disclosure employ a urinary EMV mRNA assay in which EMV from urine of a human subject is screened for urothelial cancer biomarkers. Urinary EMV mRNA profiles of a healthy volunteer were analyzed by RNA-seq and found to express not only kidney specific genes but also bladder specific genes, suggesting that urinary EMV may be useful to detect urothelial diseases (e.g., ureter and renal pelvis cancers) as well as bladder cancer. Because urothelial cancers are directly in contact with urine, it is possible molecular signatures of urothelial cancers may be detected earlier in urinary EMV compared to the urinary cell or protein biomarkers that are analyzed under current clinical practice.

Patients and Samples

This study was reviewed and approved by the institutional review board at Sapporo City General Hospital (approval no. H25-047-197). Patients with suspected urothelial cancers were recruited and diagnosed by cystoscopy and urine cytology. Up to 15 mL spot urine was collected prior to cystoscopy with an informed consent (see Tables 1 and 2). Spot urine from healthy donors was collected anonymously. The urine samples were stored at −80° C. within 3 hours after the collection.

Exosome Isolation and Characterization

In some embodiments, EMV were isolated using a differential centrifugation method described previously by Murakami et al. (PLoS ONE 9: e109074 (2014)). Dynamic light scattering analysis of isolated EMV was conducted in PBS by SZ-100 (Horiba Instruments, CA). Z-average value was obtained following the instrument control software and used to investigate the size distribution of EMV. The quantity of EMV was determined using EXOCET exosome quantitation kit (System Biosciences, CA).

In some embodiments, urinary EMV were isolated using the Exosome Isolation Tube (Hitachi Chemical Diagnostics, Inc., CA).

Urine EMV RNA-Seq Analysis

RNA-seq analysis of urine samples from urothelial cancer patients was conducted in comparison with healthy, disease controls and cancer remission in order to screen urothelial cancer biomarkers. Urinary EMV mRNA profiles were analyzed by RNA-seq, as described below, using EMV obtained from urine samples of healthy donors (N=3), disease control and cancer remission patients (N=3), patients having mild bladder cancer (N=3), and patients having advanced urothelial cancer (N=3) (see Table 1).

TABLE 1

Patient samples used for urinary EMV mRNA-seq analysis.

| RNAseq ID | Diagnostic group | Stage | Grade | Comments |
| --- | --- | --- | --- | --- |
| RS01 | Healthy control | | | |
| RS02 | Healthy control | | | |
| RS03 | Healthy control | | | |
| RS04 | Disease control | | | Atypical epithelium, reddened |
| RS05 | Cancer remission | | | No neoplastic change |
| RS06 | Cancer remission | | | Epithelial granuloma |
| RS07 | Mild bladder cancer | pTa | G2 | Recurrence |
| RS08 | Mild bladder cancer | pTa | G2 | Recurrence |
| RS09 | Mild bladder cancer | pTa | G2 | Flat like |
| RS10 | Advanced bladder cancer | pT4a | G3 | Cystectomy |
| RS11 | Advanced renal pelvis cancer | pT2 | G3 | Nephrectomy |
| RS12 | Advanced renal pelvis cancer | pT3 | G3 | Nephrectomy |

Urinary EMV were isolated using the Exosome Isolation Tube (Hitachi Chemical Diagnostics, Inc., CA). The captured EMV were lysed on the filter tip, and the resultant lysates were transferred by centrifugation to a T7 promoter oligo(dT)-immobilized microplate for mRNA hybridization. The hybridized mRNA was amplified by MEGAscript T7 Transcription Kit (Life Technologies, CA) directly on the plate. RNA was purified using RNeasy MinElute Cleanup kit before being used as starting material for TruSeq library preparation (Illumina, CA). A 50-cycle single read run was done on an Illumina HiSeq 2500 instrument. After the obtained raw reads were filtered and deduplicated by FASTX-Toolkit and mapped against hg38 by TopHat, the read counts were obtained by HTSeq and analyzed by edgeR as described by Anders, et al. A FDR (false detection rate)<5% criterion was used to detect differentially expressed genes by edgeR. Additionally, ingenuity pathway analysis (Qiagen, CA) was employed to identify dysregulated pathways in comparison with bladder tumors using the gene expression profiles obtained from the Cancer Genome Atlas.

Figure 1B:
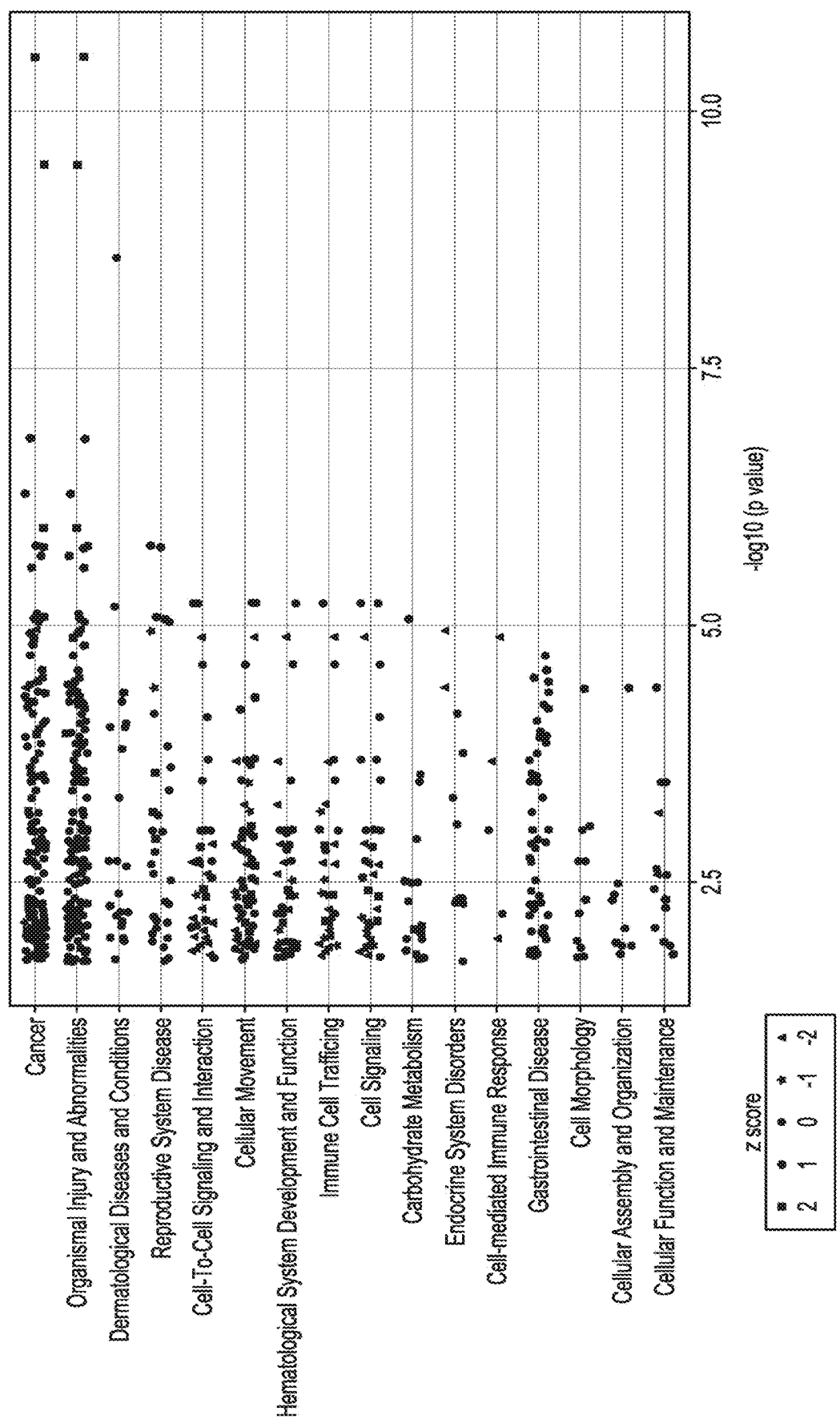
FIG. 1B depicts ingenuity pathway analysis of bladder tumors to identify dysregulated pathways.
Figure 1C:
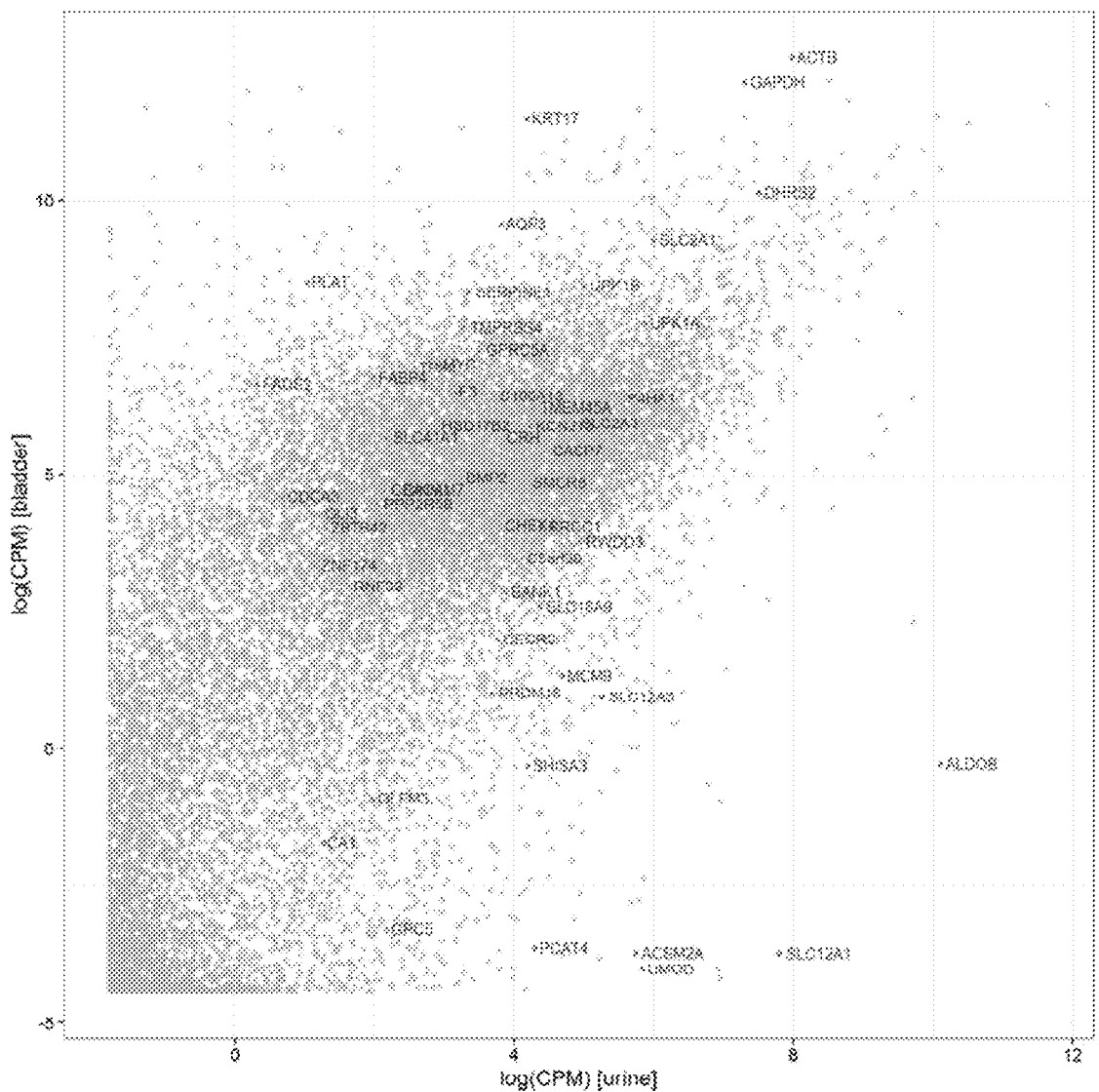
FIG. 1C shows comparison between gene expression in urinary EMV mRNA and in bladder cancer biopsy mRNA.

Principal component analysis of the RNA-seq data detected several possible clusters corresponding to the above sample categories (FIG. 1A): healthy, disease controls and cancer remission (RS01-RS06), mild bladder cancer (RS07-RS09), and advanced urothelial cancer (RS10-RS12). Interestingly, cancer remission samples (RS05, RS06) were located at the boundary between healthy and disease controls and urothelial cancers. These data suggest that urinary EMV mRNA profiles could be used to detect and distinguish urothelial cancers by locations, grades and stages. Pathway analysis was conducted to identify dysregulated networks in urothelial cancer patient urine samples. In both bladder and renal pelvis cancer urines, pathways related with organismal injury and abnormalities and cancer, were dysregulated (FIG. 1B), which is in accordance with the patterns observed in bladder tumors. In bladder cancer urines, additional pathways such as cellular movement, hematological system development and function, cell-to-cell signaling and interaction, immune cell trafficking and cell death and survival, were also dysregulated, suggesting that immune functions of the bladder cancer patients are compromised and can be monitored by analyzing urinary EMV gene expression.

Unsupervised clustering analysis of urinary EMV mRNA profiles clearly showed different clusters indicating healthy control, bladder cancer, renal pelvis cancer, mild and advanced urothelial cancers. By comparing among these aforementioned groups, edgeR analysis of urinary EMV mRNA-seq data identified 94 differentially expressed genes (68 up-regulated and 26 down-regulated genes) as candidate markers to detect and distinguish urothelial cancers by locations, grades and stages (Table 2).

TABLE 2

Differentially-expressed genes in urothelial cancer urine.

| Target group | Control group | No. of differentially expressed genes | |
|---|---|---|---|
| | | Up regulated | Down regulated |
| UC | HC | 2 | 2 |
| UC | DC and RMSN | 0 | 2 |
| UC | HC, DC and RMSN | 3 | 0 |
| BC | HC, DC and RMSN | 36 | 19 |
| BC | DC and RMSN | 27 | 1 |
| RPC | HC, DC and RMSN | 1 | 0 |
| RPC | HC | 0 | 0 |
| Advanced UC | HC | 2 | 0 |
| Advanced UC | HC, DC and RMSN | 1 | 0 |
| Mild UC | HC | 12 | 0 |
| Mild UC | HC, DC and RMSN | 22 | 4 |
| Recurrent | Non recurrent | 0 | 0 |
| | Total | 68 | 26 |

Among the obtained genes, P4HA1, GPRC5A, MYC, F3, KRT17, SHISA3, CBX7 and SPTLC3 are especially promising biomarkers of urothelial cancers as their expression levels in urinary EMV are highly correlated with the stages of urothelial cancers. CRH and TMPRSS4 are also promising as these genes were differentially expressed between mild urothelial cancer and disease control groups. Furthermore, PRSS58, KLRC1, PRPS1L1, TRPM6, CACNA1C, FRG2, LVRN, MFGE8, ZNF704, CDK9, MCF2L and TOMM70A are more specific to renal pelvis cancers than bladder cancers, and useful to detect renal pelvis cancers as well as to distinguish between bladder and renal pelvis cancers. Interestingly, analysis of the Cancer Genome Atlas revealed that a majority of these differentially-expressed genes were also dysregulated in bladder cancer tumors (N=408) compared to matched normal bladder tissues (N=19). The functional classification analysis of these genes by PANTHER revealed many of the molecular functions such as catalytic activity and binding and biological processes such as metabolic and cellular processes are dysregulated in urothelial cancers. Some of these differentially-expressed genes and additional genes of interest were selected for further analysis using RT-qPCR, as described below.

Urinary EMV mRNA Analysis for RT-qPCR

Among the differentially-expressed genes in urinary EMV, 60 genes, including reference genes, were further assayed by RT-qPCR. Urine samples were obtained from healthy donors (N=9) and from patients having urothelial cancer or other cancers (N=245) (see Table 3). Urinary EMV mRNA assay was conducted as previously described by Murakami et al. (PLoS ONE 9: e109074 (2014)), except that 10 µM random hexamer was added at cDNA synthesis step. The primer sequences are listed in Table 4. Threshold cycle (Ct) values were obtained using the ViiA7 software (Life Technologies, CA) with a manual threshold setting of 0.1 and a maximum Ct value of 36 (raw Ct data). Further, data processing and analysis were performed using R ver. 3.2. For normalization of gene expression, delta Ct (dCt) method was employed using the following formula: dCt=Ct [target gene]-Ct [reference gene]. A maximum dCt of 10 was used when ALDOB was used as a reference gene. When target gene was not detected or amplified correctly determined by melting curve analysis, the maximum dCt was assigned. Statistical significance was obtained by Welch's t-test or Mann-Whitney-Wilcoxon test with p value <5%. Diagnostic performance was evaluated by the area under the curve (AUC) in ROC curve analysis using ROCR. Sparse logistic regression was done using glmnet. Support vector machine (SVM) was done using kernlab.

TABLE 3

Sample information for urinary EMV mRNA RT-qPCR analysis.

| Diagnostic group | Urine (Subject) | Stage | Grade | Recurrence | Cytology (+) | BTA*** [ng/mL] |
|---|---|---|---|---|---|---|
| Healthy control (HC) | 9 (9) | — | — | — | — | 3.0 ± 0.0 |
| Disease control (DC)* | 9 (9) | — | — | — | — | 7.9 ± 14.8 |
| Cancer remission (RMSN) | 27 (26) | — | — | — | — | 4.0 ± 2.8 |
| Bladder cancer (BC) | 173 (131) | 0.4 ± 0.8 | 2.3 ± 0.5 | 45% | 27% | 10.5 ± 19.1 |

TABLE 3-continued

Sample information for urinary EMV mRNA RT-qPCR analysis.

| Diagnostic group | Urine (Subject) | Stage | Grade | Recurrence | Cytology (+) | BTA*** [ng/mL] |
|---|---|---|---|---|---|---|
| Renal pelvis cancer (RPC) | 26 (25) | 1.4 ± 1.4 | 2.6 ± 0.5 | 0% | 17% | 15.0 ± 27.6 |
| Ureter cancer (URC) | 7 (7) | 2.2 ± 1.3 | 2.6 ± 0.5 | 0% | 14% | 3.9 ± 2.4 |
| Other cancer (OT)** | 3 (3) | 3.0 | 3.0 | — | 0% | 3.0 ± 0.0 |
| Total | 254 (208) | | | | | |

*DC includes non-cancer patients such as no neoplastic change (N = 4), benign epithelium (N = 1), chronic pyelonephritis (N = 1), inverted papilloma (N = 1), methicillin-resistant *Staphylococcus aureus* (MRSA) infection (N = 1), and inflammatory polyp (N = 1).
**OT includes non-urothelial cancer patients such as adenocarcinoma (N = 1), renal cell carcinoma (N = 1), and prostate cancer (N = 1).
***Bladder Tumor Antigen (BTA) was assayed by a commercially-available BTA ELISA kit (Biotang, MA).

TABLE 4

Primer sequence list.

| Gene Symbol | Sense primer (5' to 3') | Anti sense primer (5' to 3') |
|---|---|---|
| ACSM2A | aagacagcagccaacattcg (SEQ ID NO: 1) | tttgcccgtcccataaactg (SEQ ID NO: 2) |
| ACTB | ttttcctggcacccagcacaat (SEQ ID NO: 3) | tttttgccgatccacacggagtact (SEQ ID NO: 4) |
| ALDOB | aaccaccattcaagggcttg (SEQ ID NO: 5) | ttggcgttttcctggatagc (SEQ ID NO: 6) |
| AQP3 | ttttgtttcgggccccaatg (SEQ ID NO: 7) | ttgtaggggtcaacaatggc (SEQ ID NO: 8) |
| BANK1 | tggcctggaaatgattcagc (SEQ ID NO: 9) | ttgtgggcagtttccttacc (SEQ ID NO: 10) |
| BKPyVgp4 | acagcacagcaagaattccc (SEQ ID NO: 11) | tttgtgaccctgcatgaagg (SEQ ID NO: 12) |
| BMP2 | agcagagcttcaggttttcc (SEQ ID NO: 13) | tttcgagttggctgttgcag (SEQ ID NO: 14) |
| C5orf30 | tttggttggcttcacgactg (SEQ ID NO: 15) | atggcatggcttctgctttg (SEQ ID NO: 16) |
| CA1 | ttgctgaagctgcctcaaag (SEQ ID NO: 17) | tttctgcagctttgggttgg (SEQ ID NO: 18) |
| CASP7 | ttccacggttccaggctattac (SEQ ID NO: 19) | tggcaactctgtcattcacc (SEQ ID NO: 20) |
| CDCA3 | tcttggtattgcacggacac (SEQ ID NO: 21) | tacccagaggcaagtccaattc (SEQ ID NO: 22) |
| CEACAM7 | tcagcgccacaaagaatgac (SEQ ID NO: 23) | aggtcaggtgaacttgcttg (SEQ ID NO: 24) |
| CECR2 | aagcatctccttgtggatcgg (SEQ ID NO: 25) | tggtttcctgcaacgttctg (SEQ ID NO: 26) |
| CHEK1 | aggggtggtttatctgcatgg (SEQ ID NO: 27) | tgttgccaagccaaagtctg (SEQ ID NO: 28) |
| CRH | atctccctggatctcaccttc (SEQ ID NO: 29) | tgtgagcttgctgtgctaac (SEQ ID NO: 30) |
| DHRS2 | tgagcagatctgggacaagatc (SEQ ID NO: 31) | aagctgcaatggaagagacc (SEQ ID NO: 32) |
| F3 | tcggacagccaacaattcag (SEQ ID NO: 33) | agtccttgccaaaaacatccc (SEQ ID NO: 34) |
| FABP4 | cctggtacatgtgcagaaatgg (SEQ ID NO: 35) | acgcctttcatgacgcattc (SEQ ID NO: 36) |
| FADS2 | ccaccttgtccacaaattcgtc (SEQ ID NO: 37) | aacacgtgcagcatgttcac (SEQ ID NO: 38) |

TABLE 4-continued

Primer sequence list.

| Gene Symbol | Sense primer (5' to 3') | Anti sense primer (5' to 3') |
|---|---|---|
| GAPDH | cccactcctccacctttgac (SEQ ID NO: 39) | cataccaggaaatgagcttgacaa (SEQ ID NO: 40) |
| GINM1 | ttctggagcaacgttttccc (SEQ ID NO: 41) | cagctgctcctgtaattccaac (SEQ ID NO: 42) |
| GLI3 | aatgtttccgcgactgaacc (SEQ ID NO: 43) | ttggactgtgtgccatttcc (SEQ ID NO: 44) |
| GPC5 | acgtgctgctgaactttcac (SEQ ID NO: 45) | aaagaacaacggggctttg (SEQ ID NO: 46) |
| GPRC5A | gctcatgcttcctgactttgac (SEQ ID NO: 47) | ttgtgagcagccaaaactcg (SEQ ID NO: 48) |
| HSD17B2 | tttttaacaatgcatggccgtgaac (SEQ ID NO: 49) | tttttatgctgctgacattcaccag (SEQ ID NO: 50) |
| KCNJ15 | aatcgccagacccaaaaagc (SEQ ID NO: 51) | aatcaccaagcacagcttcc (SEQ ID NO: 52) |
| KRT17 | tggacaatgccaacatcctg (SEQ ID NO: 53) | tcaaacttggtgcggaagtc (SEQ ID NO: 54) |
| LINC00967 | tggagatggttggggtcaaatc (SEQ ID NO: 55) | tgcatccacaaagcacactg (SEQ ID NO: 56) |
| LRRCC1 | tgagctagcagccaaggaatc (SEQ ID NO: 57) | ttgttgtgccagctcatgtc (SEQ ID NO: 58) |
| MCM9 | tgtaatgcaacggtggaagc (SEQ ID NO: 59) | tcatccatgatgatccctgagg (SEQ ID NO: 60) |
| MYC | acacatcagcacaactacgc (SEQ ID NO: 61) | ggtgcattttcggttgttgc (SEQ ID NO: 62) |
| NRSN2-AS1 | tgccaacaccaacaaggaac (SEQ ID NO: 63) | ttgcagttgagatgctggtc (SEQ ID NO: 64) |
| OLFM3 | accaaagagtgctgagcttg (SEQ ID NO: 65) | tcatccaagcaccaaatcgg (SEQ ID NO: 66) |
| P4HA1 | agttggagctagtgtttggc (SEQ ID NO: 67) | ttgttgccaactagcactgg (SEQ ID NO: 68) |
| PCAT4 | tttttcacgatgcgatgtcatgtc (SEQ ID NO: 69) | tttttgtcccaaattgtcgtccag (SEQ ID NO: 70) |
| PLAT | tgatcttgggcagaacataccg (SEQ ID NO: 71) | agcagcgcaatgtcattgtc (SEQ ID NO: 72) |
| PPP2R5B | acagtgcaaccacatcttcc (SEQ ID NO: 73) | cgcaaagccattgatgatgc (SEQ ID NO: 74) |
| PRDM16 | ggacaaccacgcacttttagac (SEQ ID NO: 75) | ttcgcgttgatgcttggttc (SEQ ID NO: 76) |
| RNF39 | tcctgcagagactcttctgg (SEQ ID NO: 77) | cttgcgttgcactgattccc (SEQ ID NO: 78) |
| RWDD3 | tggtgttccatttgccagtc (SEQ ID NO: 79) | acaaaaggctctctgcttgc (SEQ ID NO: 80) |
| S100A13 | accaccttcttcacctttgc (SEQ ID NO: 81) | cagctctttgaactcgttgacg (SEQ ID NO: 82) |
| SERPINE1 | accctcagcatgttcattgc (SEQ ID NO: 83) | tcatgttgccttttccagtgg (SEQ ID NO: 84) |
| SHISA3 | tcaccccagtatttcgcttacc (SEQ ID NO: 85) | tggaactgaagtctggacagc (SEQ ID NO: 86) |
| SLC12A1 | actccagagctgctaatctcattgt (SEQ ID NO: 87) | aactagtaagacaggtgggaggttct (SEQ ID NO: 88) |

TABLE 4-continued

Primer sequence list.

| Gene Symbol | Sense primer (5' to 3') | Anti sense primer (5' to 3') |
|---|---|---|
| SLC12A3 | gctctcatcgtcatcactttgc (SEQ ID NO: 88) | agcacgttttcctggtttcc (SEQ ID NO: 90) |
| SLC16A9 | acattggcgttgctttctgg (SEQ ID NO: 91) | attcccacagtcttcgtggtc (SEQ ID NO: 92) |
| SLC2A1 | tcattgtgggcatgtgcttc (SEQ ID NO: 93) | accaggagcacagtgaagatg (SEQ ID NO: 94) |
| SLC2A3 | tgttcaagagcccatctatgcc (SEQ ID NO: 95) | tgagcgtggaacaaaaagcc (SEQ ID NO: 96) |
| SLC41A1 | atcattgccatggccatcag (SEQ ID NO: 97) | tgccccaacaccattaatc (SEQ ID NO: 98) |
| SMCR8 | tgaggccatagtcaggaaactc (SEQ ID NO: 99) | aatgtttcacgggcttagcg (SEQ ID NO: 100) |
| THAP7-AS1 | aacccgacaaaaaccagagc (SEQ ID NO: 101) | gcgatactgtctttctcctgtg (SEQ ID NO: 102) |
| TMEM45A | acatctttgtgcaccagctg (SEQ ID NO: 103) | aaggaactctaggaaggcaacg (SEQ ID NO: 104) |
| TMPRSS4 | agatgatgtgtgcaggcatc (SEQ ID NO: 105) | acatgccactggtcagattg (SEQ ID NO: 106) |
| TOP1P1 | aaacagatggccttgggaac (SEQ ID NO: 107) | tttcaatggcccaggcaaac (SEQ ID NO: 108) |
| TPX2 | agtcaccagcctttgcattg (SEQ ID NO: 109) | taatgtggcacaggttgagc (SEQ ID NO: 110) |
| UMOD | cctgaacttgggtcccatca (SEQ ID NO: 111) | gccccaagctgctaaaagc (SEQ ID NO: 112) |
| UPK1A | atccctgatcaccaagcagatg (SEQ ID NO: 113) | aaggctgacgtgaagttcac (SEQ ID NO: 114) |
| UPK1B | aggcgtgcctggttttatc (SEQ ID NO: 115) | aaatccaaaccaggcaaccc (SEQ ID NO: 116) |
| ZBTB42 | ttgtgcagcaagctgtttcc (SEQ ID NO: 117) | tatgtgcacgagaaggtcttcc (SEQ ID NO: 118) |
| ZNF174 | aactgccagactttcaaccg (SEQ ID NO: 119) | atttgggggttggttcttgg (SEQ ID NO: 120) |

In order to normalize gene expression levels of marker candidates in the RT-qPCR assay, reference gene candidates were also screened and selected. Many reference genes such as ACTB, GAPDH and ribosomal RNA have been used to normalize the expression levels of mRNA in general. GAPDH has been used frequently in urinary EMV studies as GAPDH is expressed abundantly and is detectable in almost all the urine samples. For normalization, the delta Ct method is frequently used in order to improve inter-assay reproducibility. In the delta Ct method, the cycle threshold (Ct) value of the marker candidate is subtracted from the Ct value of the reference gene. Thus, the smaller the delta Ct value, the higher the marker gene expression. Ideally, the gene expression level of a reference gene should be stable independent of disease status. However, when the number of EMV in urine is affected by disease status, ubiquitously expressed genes may not be ideal as reference genes because their expression levels are also affected. For example, when bladder disease affects the number of EMV originated in bladder, it is expected that the number of total EMV or EMV originated in bladder in urine samples will change based on disease status. Since ubiquitously expressed genes such as ACTB, GAPDH and ribosomal RNA are also expressed in bladder, the expression levels of these genes in urinary EMV will be affected by the bladder disease status. However, it is very unlikely that bladder disease status affects kidney function as the kidney is located upstream in the urinary tract. Therefore, the number of kidney-originating EMV that are released into the urine may not be affected by bladder disease status. Therefore, kidney-specific genes, or any other genes which are not expressed in bladder, are ideal reference genes to normalize the expression levels of marker genes for bladder diseases. Thus, in several embodiments, reference genes are derived from EMV from a first organ, while EMV of interest are from a different organ (e.g., the kidney).

Figure 2A:
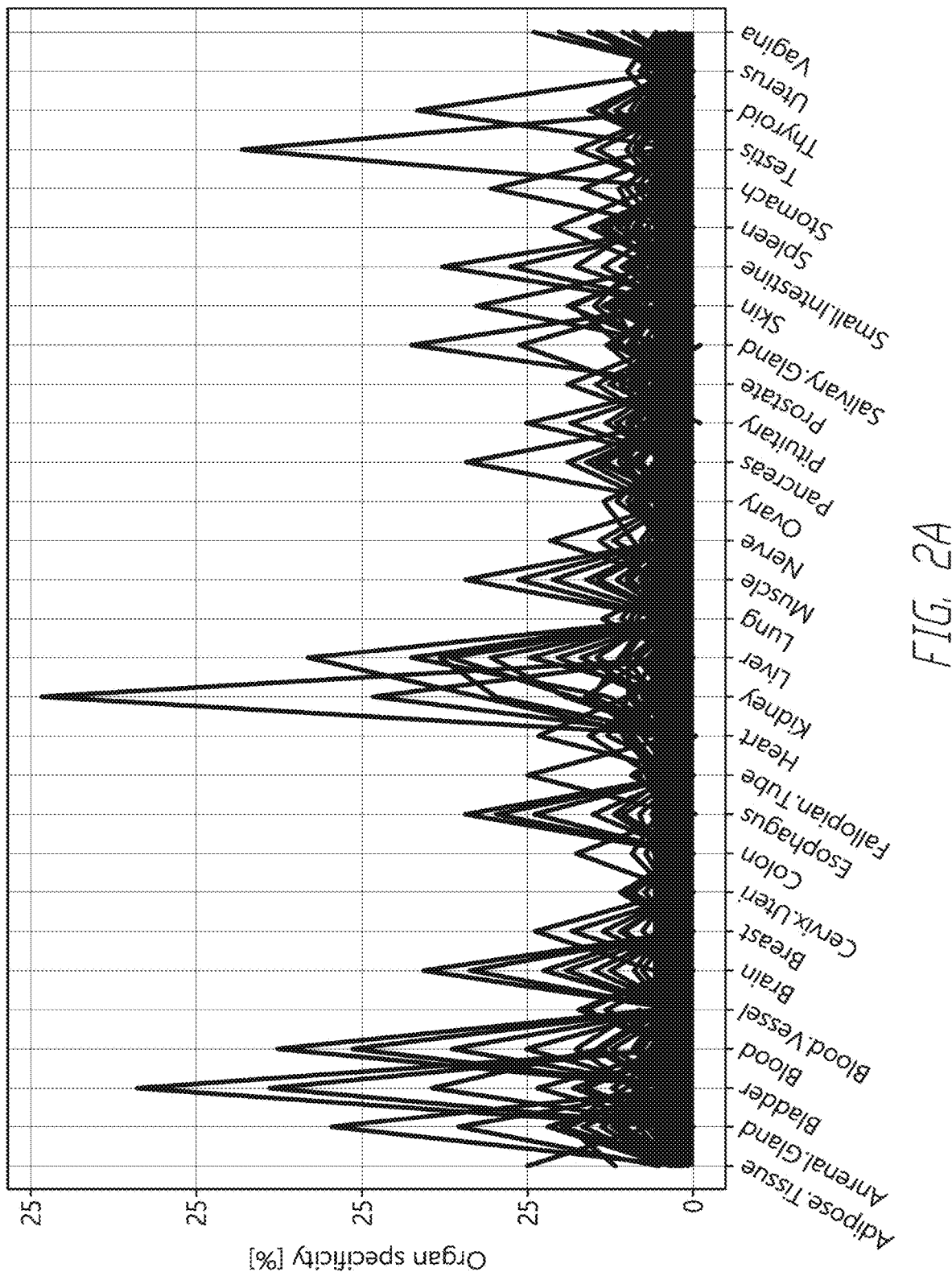
FIG. 2A depicts organ expression of the one thousand most abundant urinary EMV mRNA.
Figure 2B:
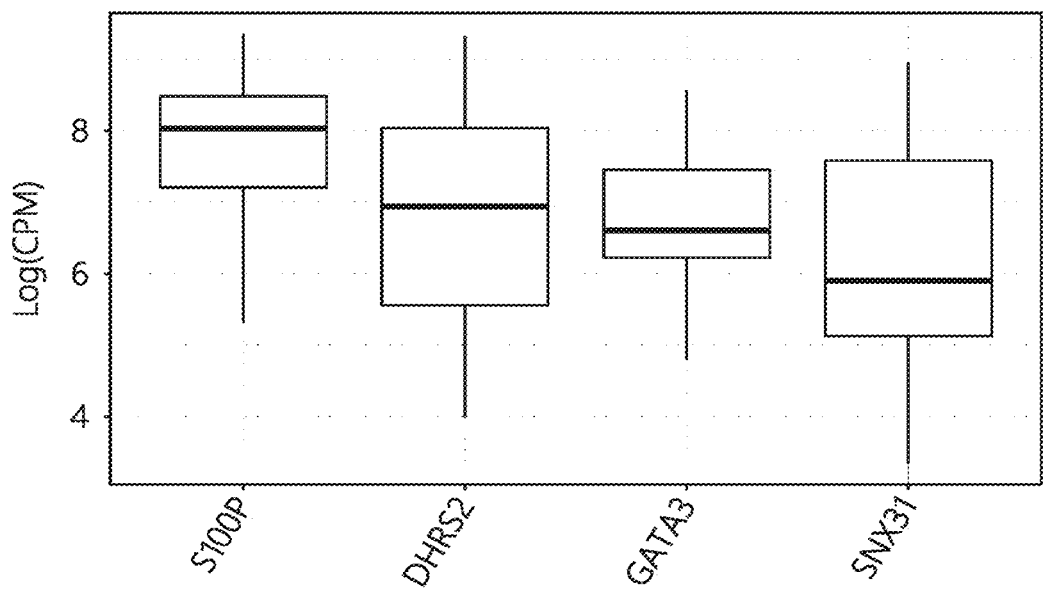
FIG. 2B depicts expression levels of bladder-specific genes that are expressed abundantly in urinary EMV.
Figure 2C:
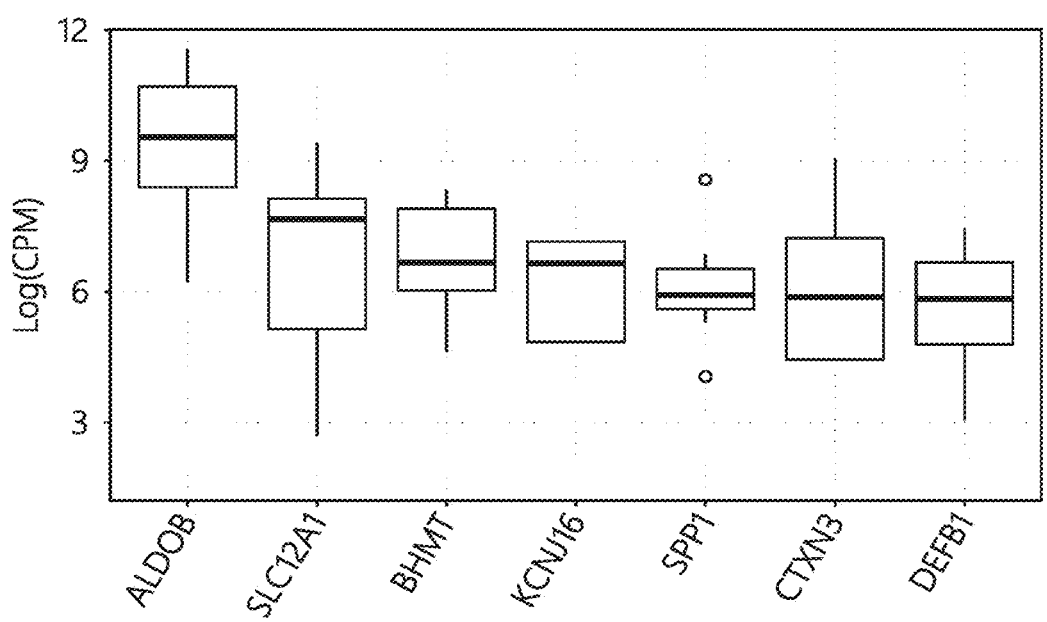
FIG. 2C depicts expression levels of kidney-specific genes that are expressed abundantly in urinary EMV.
Figure 2E:
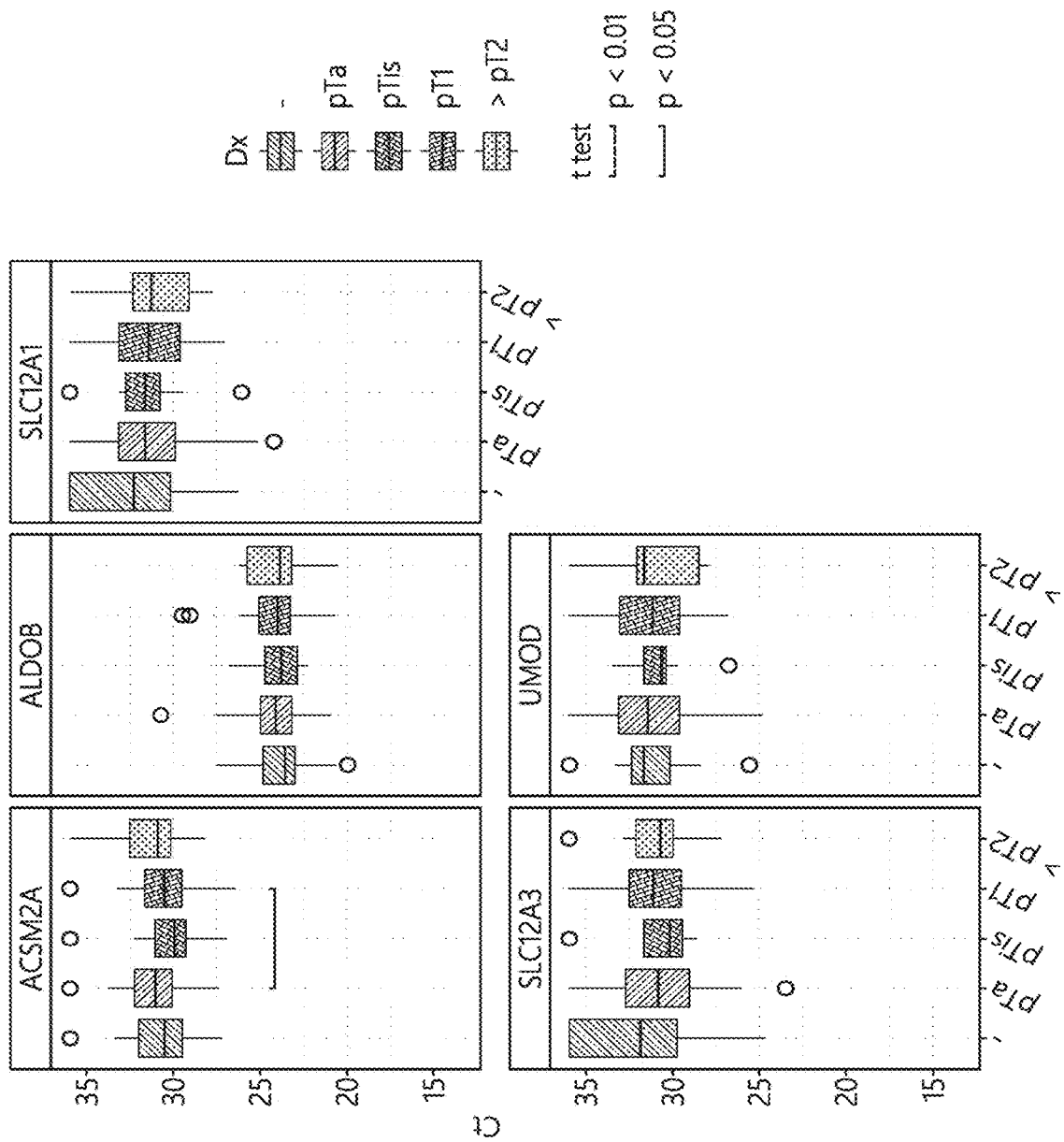
FIG. 2E shows box-and-whisker plots of raw Ct values in the RT-qPCR assay of different urinary EMV mRNA in different bladder cancer stages.

In order to select organ-specific genes expressed in urinary EMV, the 1000 most abundant mRNA expressed in urinary EMV were selected from the RNA-seq data of urinary EMV, and the organ specificity or the expression pattern in various organs of each gene was investigated using GTEx database (Broad Institute). The majority of the most abundant mRNA in urinary EMV are expressed ubiquitously. However, some of the most abundant urinary EMV mRNA are expressed specifically in certain organs such as kidney, bladder and liver (FIG. 2A). The bladder-specific genes that are expressed abundantly in urinary EMV are, for example, S100P, DHRS2, GATA3, SNX31, UPK1A and UPK1B (FIG. 2B). The kidney-specific genes that are expressed abundantly in urinary EMV are, for example, ALDOB, SLC12A1, BHMT, KCNJ16, SPP1, CTXN3, DEFB1 and UMOD (FIG. 2C).

In order to select reference genes, analysis of variance (ANOVA) was conducted using raw Ct values of tested reference gene candidates (FIG. 2D, Table 5). Ten reference gene candidates were selected from ubiquitously expressed genes, bladder-specific genes, and kidney-specific genes, and their raw Ct values in the RT-qPCR assay were compared by ANOVA among the different diagnostic groups such as type of cancer (Dx), bladder cancer stages (Stage) or bladder cancer grades (Grade).

TABLE 5

ANOVA analysis of reference gene expression.

| Organ specificity | Gene | Ct mean | Ct median | ANOVA p value Dx | Stage | Grade |
|---|---|---|---|---|---|---|
| Ubiquitous | ACTB | 25.6 | 25.8 | 0.1413 | 7E-07 | 0.0013 |
|  | GAPDH | 26.0 | 26.2 | 0.0888 | 2E-07 | 0.0002 |
| Bladder | DHRS2 | 27.0 | 26.8 | 0.2018 | 0.1423 | 0.1067 |
|  | UPK1A | 29.0 | 28.8 | 0.4592 | 0.3764 | 0.5713 |
|  | UPK1B | 33.0 | 33.1 | 0.105 | 3E-05 | 0.0037 |
| Kidney | ACSM2A | 31.1 | 30.8 | 0.4473 | 0.1076 | 0.0805 |
|  | ALDOB | 24.1 | 23.9 | 0.6534 | 0.9641 | 0.5426 |
|  | SLC12A1 | 31.9 | 31.6 | 0.4424 | 0.5933 | 0.4571 |
|  | SLC12A3 | 31.6 | 31.0 | 0.0013 | 0.3554 | 0.0956 |
|  | UMOD | 31.4 | 31.3 | 0.3785 | 0.8876 | 0.6926 |

ANOVA indicated that ACTB, GAPDH and UPK1B are differentially expressed among the diagnostic groups such as bladder cancer stage and grade although they are not among the different cancer types. On the other hand, ALDOB was highly expressed in urinary EMV (mean Ct=24.1 and median Ct=23.9) and was not differentially expressed among any diagnostic groups such as cancer type, bladder cancer stage and grade, therefore ALDOB is an ideal reference gene among the genes tested here. Alternatively, DHRS2 and UPK1A are also ideal reference genes as their expression levels are relatively high and not differentially expressed among any diagnostic groups.

The gene expression profiles were normalized by ALDOB using delta Ct method as described above and analyzed by disease status such as cancer type (FIG. 3A), bladder cancer stage (FIG. 3B), and bladder cancer grade (FIG. 3C). The diagnostic performances of these urinary EMV mRNA were evaluated using ROC curve analysis by comparing bladder cancer to disease control and cancer remission (Table 6). The diagnostic performance of individual markers to detect bladder cancer at various stages and grades was evaluated by area under the curve in ROC curve analysis. The control group was DC and RMSN (N=36). The 60 EMV mRNA markers were compared with the conventional assays such as urine cytology and bladder tumor antigen (BTA) ELISA assay. For urine cytology, three different scorings were used: Cytology1; Positive (2), suspicious (1) and negative (0), Cytology2; Positive/suspicious (1) and negative (0), and Cytology3; Positive (1) and suspicious/negative (0).

Urinary EMV mRNA markers such as SLC2A1, S100A13, GAPDH, KRT17, GPRC5A, P4HA1, AQP3, SLC12A3, TMPRSS4, SLC12A1, UPK1B, FABP4, SMCR8, DHRS2, CHEK1, TOP1P1, LINC00967, CRH, MYC, ACSM2A and GLI3 were found to be useful to detect various stages and grades of bladder cancer (Table 6). SLC2A1, S100A13, GAPDH, KRT17 and GPRC5A were especially able to detect bladder cancer with high specificity and accuracy (e.g., AUC=0.64 to 0.70 for all the stages, AUC=0.56 to 0.64 for pTa, AUC=0.60 to 0.80 for pTis, AUC=0.77 to 0.86 for pT1, AUC=0.68 to 0.90 for >pT2). SLC2A1, S100A13, GAPDH, KRT17, and GPRC5A, were not only differentially expressed in the urothelial cancer urine samples in comparison with the cancer remission and disease control samples but also were able to detect non-muscle invasive early stage urothelial cancer with high specificity and sensitivity. These markers outperformed the conventional urine cytology and BTA assay (Table 6).

Figure 4A:
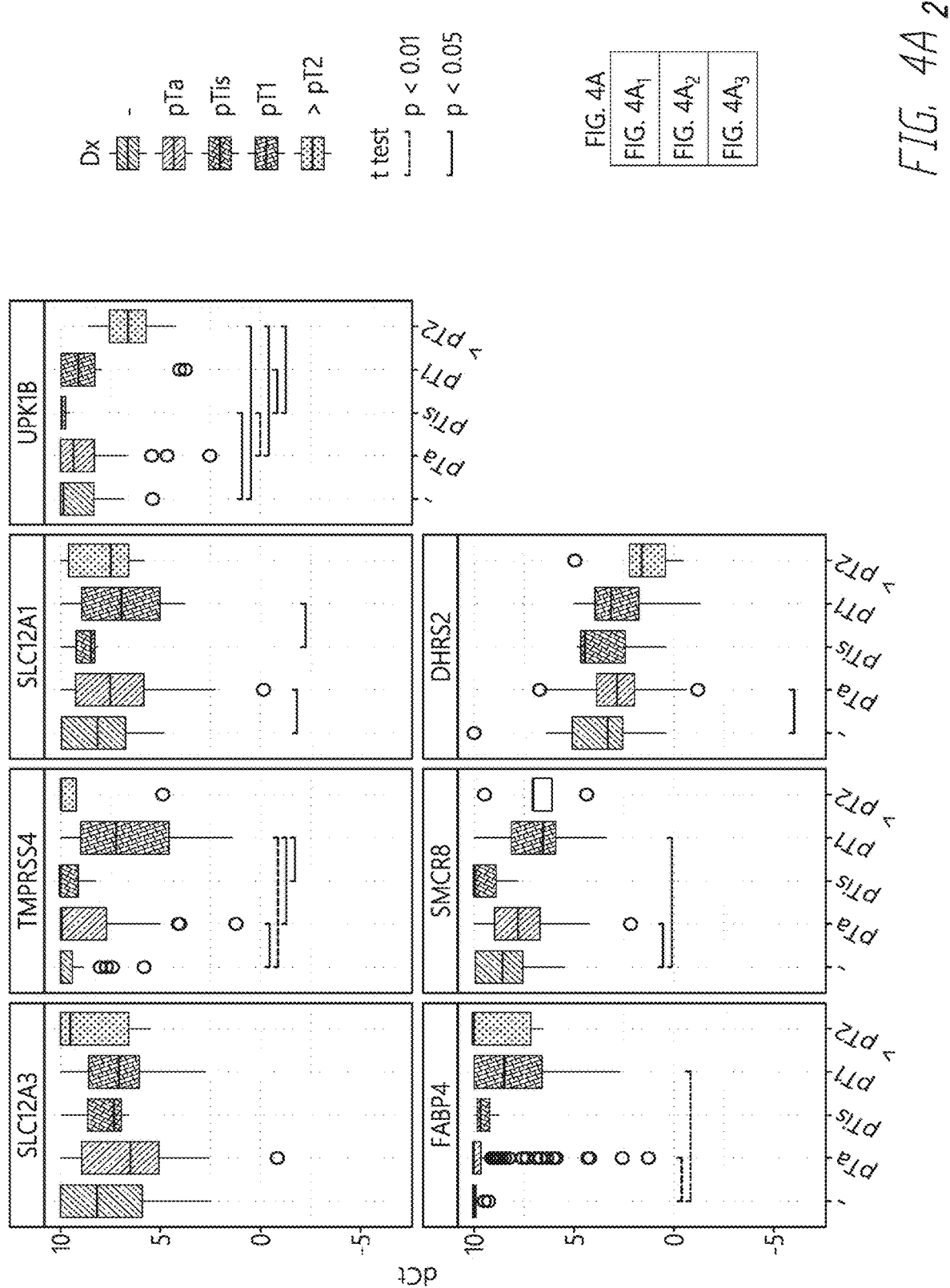
FIG. 4A depicts gene expression of urinary EMV mRNA candidates for different bladder cancer stages when conventional urine cytology result was negative or suspicious.
Figure 4B:
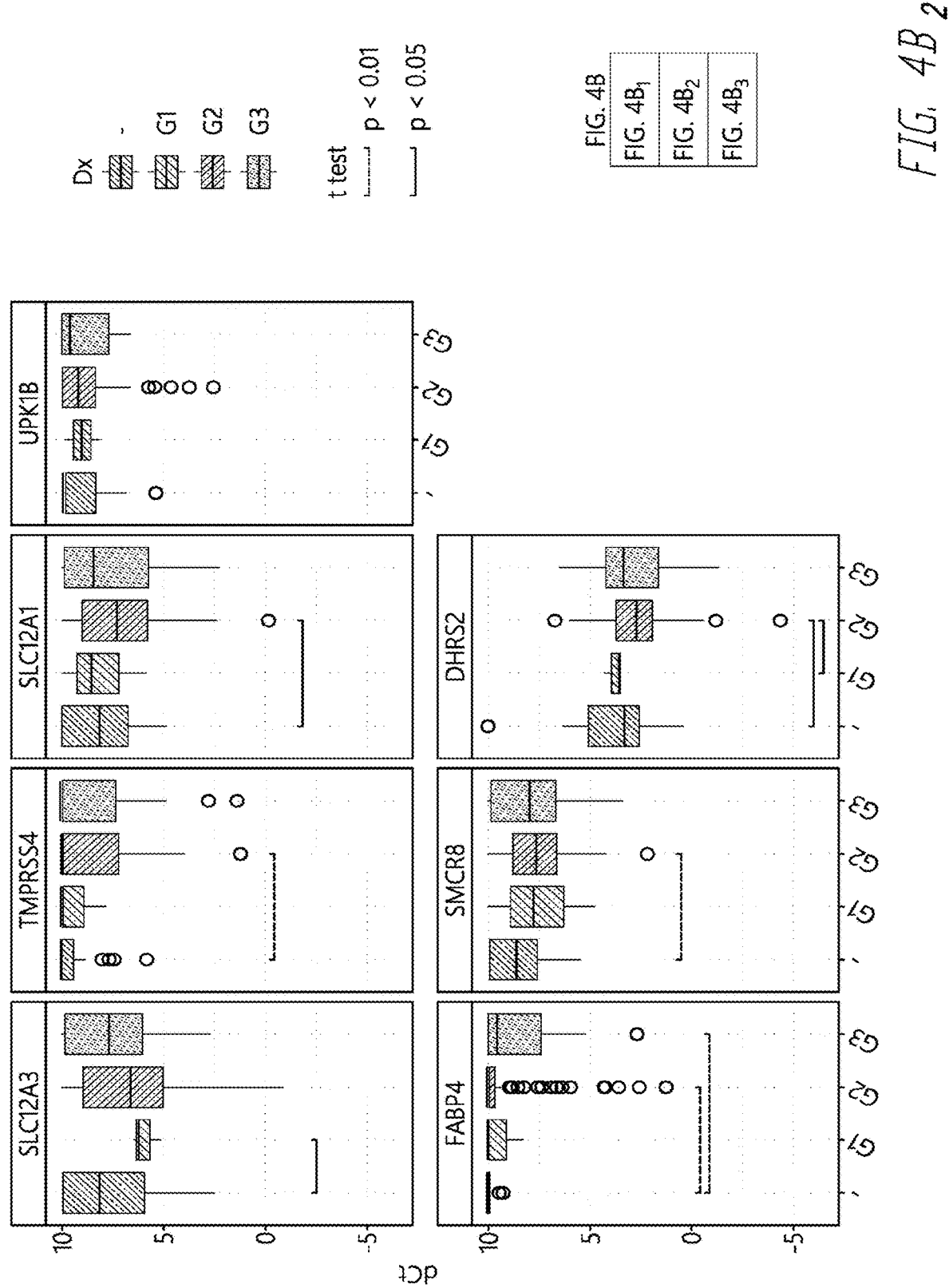
FIG. 4B depicts gene expression of urinary EMV mRNA candidates for different bladder cancer grades when conventional urine cytology result was negative or suspicious.

These markers can be used complementarily with conventional urine cytology. These EMV mRNA markers can detect bladder cancer with high diagnostic performances (Table 7), even when conventional urine cytology failed to detect bladder cancers (FIG. 4A), or when the cytology result was negative or suspicious (FIG. 4B). Diagnostic performance of individual markers to detect bladder cancer at various stages and grades was evaluated in the patient population whose urine cytology result was not positive by area under the curve in ROC curve analysis. The control group was DC and RMSN (N=26). The 60 EMV mRNA markers were compared with the conventional assays such as urine cytology and bladder tumor antigen (BTA) ELISA assay. For urine cytology, three different scorings were used: Cytology1; Positive (2), suspicious (1) and negative (0), Cytology2; Positive/suspicious (1) and negative (0), and Cytology3; Positive (1) and suspicious/negative (0).

These markers are also useful to detect recurrent bladder cancer as similar diagnostic performances were obtained even in the recurrent bladder cancer against remission group (Table 8, FIGS. 4C-D). In Table 8, diagnostic performance of individual markers to detect bladder cancer at various stages and grades was evaluated in the patient population who developed bladder cancer previously, by area under the curve in ROC curve analysis. The control group was RMSN (N=27). The 60 EMV mRNA markers were compared with the conventional assays such as urine cytology and bladder tumor antigen (BTA) ELISA assay. For urine cytology, three different scorings were used: Cytology1; Positive (2), suspicious (1) and negative (0), Cytology2; Positive/suspicious (1) and negative (0), and Cytology3; Positive (1) and suspicious/negative (0).

Additionally, the EMV mRNA markers such as KRT17, P4HA1, HSD17B2, SLC2A1, S100A13, KCNJ15, SLC12A1, F3, TMEM45A, RNF39, FABP4, TMPRSS4, UPK1B, PLAT and OLFM3 are useful to detect non-bladder cancer urothelial cancers such as renal pelvis and ureter cancers (Table 9, FIG. 4E-F). Especially, KRT17, P4HA1, HSD17B2, SLC2A1 and S100A13 were able to detect non-bladder urothelial cancer with high specificity and accuracy (e.g., AUC=0.69 to 0.77 for all the stages, AUC=0.58 to 0.77 for pTa, AUC=0.64 to 0.87 for pT1, AUC=0.63 to 0.78 for >pT2). In Table 9, diagnostic performance of individual markers to detect non-bladder urothelial cancers such as renal pelvic and ureter cancer at various stages and grades was evaluated by area under the curve in ROC curve analysis. The control group was DC and RMSN (N=36). The 60 EMV mRNA markers were compared with the conventional assays such as urine cytology and bladder tumor antigen (BTA) ELISA assay. For urine cytology, three different scorings were used: Cytology1; Positive (2), suspicious (1) and negative (0), Cytology2; Positive/suspicious (1) and negative (0), and Cytology3; Positive (1) and suspicious/negative (0).

Figure 5A:
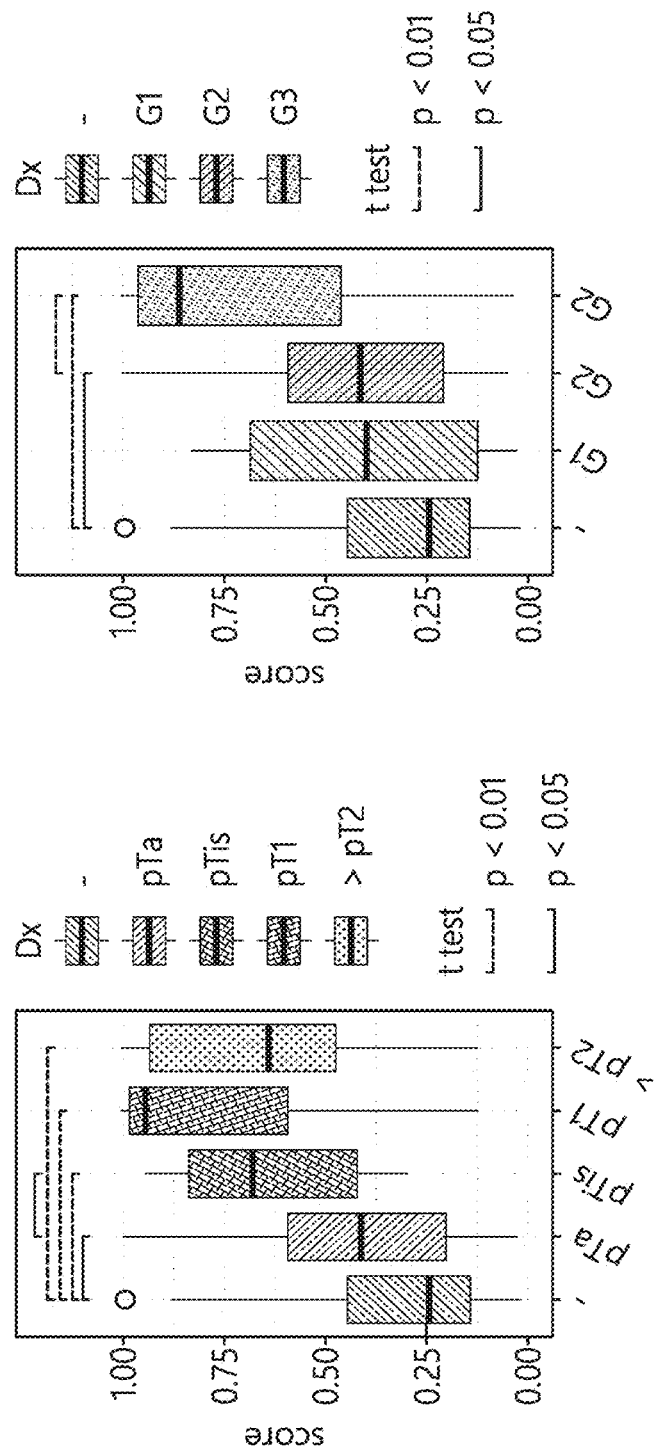
FIG. 5A shows detection performance of the logistic regression analysis formula "ALDOB+CRH+SERPINE1+SLC2A1" by bladder cancer stage and grade.
Figure 5B:
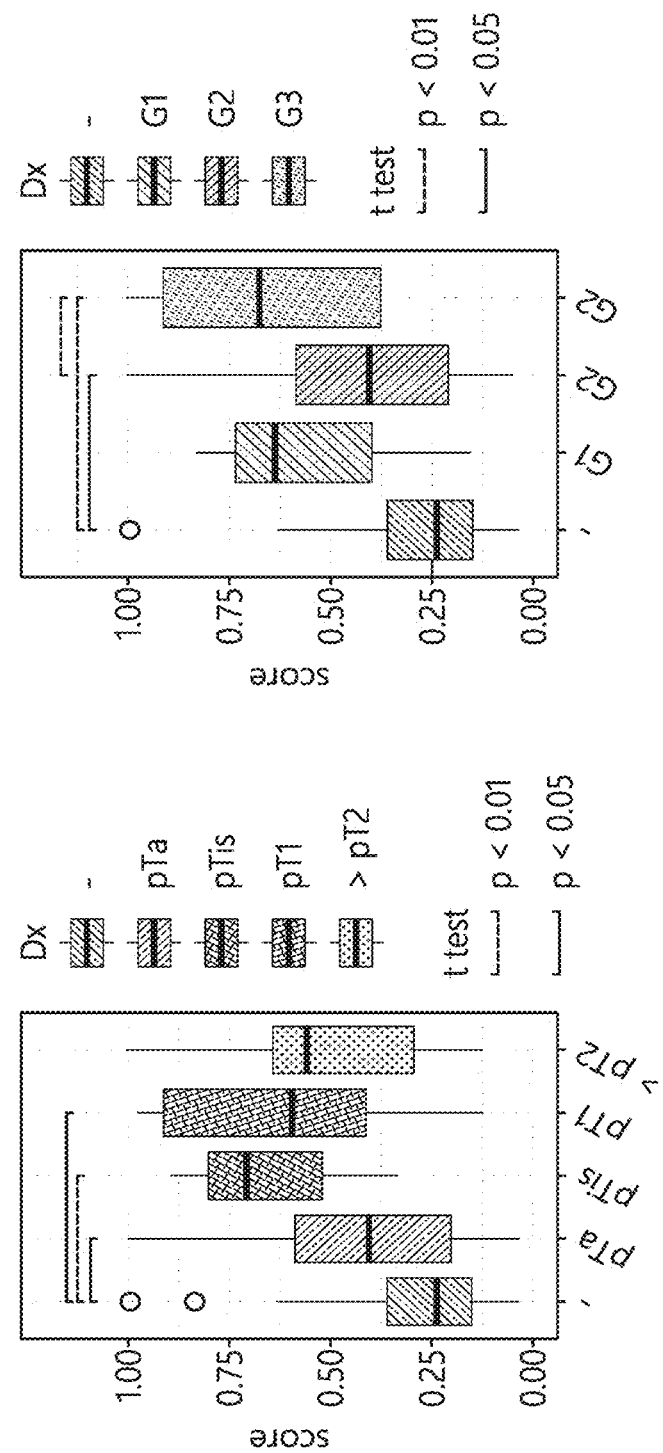
FIG. 5B shows detection performance of the logistic regression analysis formula "ALDOB+CRH+SERPINE1+SLC2A1" by bladder cancer stage and grade when conventional urine cytology result was negative or suspicious.
Figure 5C:
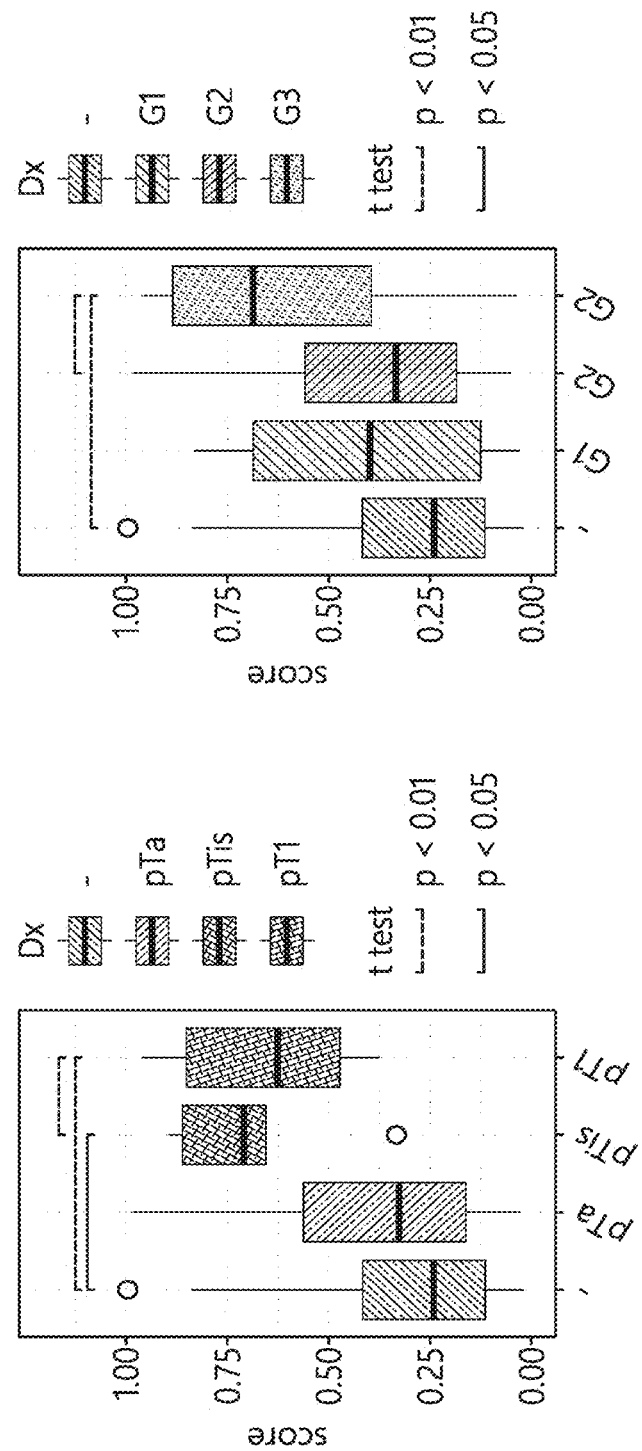
FIG. 5C shows detection performance of the logistic regression analysis formula "ALDOB+CRH+SERPINE1+SLC2A1" by bladder cancer stage and grade for detection of recurrent bladder cancer.

In order to improve the diagnostic performance of bladder cancer detection, machine learning techniques such as logistic regression analysis, random forest, and support vector machine can be used. Logistic regression analysis was conducted using the urinary EMV mRNA raw Ct data. First, diagnostic scores or probability of having a bladder cancer were assigned to the urine samples based on the actual diagnostics such as score 0 for DC and RMSN and score 1 for BC at pT1 and >pT2. These scores were predicted by the combinations of mRNA data through 100-repeats of 10-fold cross validation. All the possible combinations of one to four genes selected from the 60 gene candidates (523,685 formulas in total) were tested and the top performing formulas were selected. Their performances to detect bladder cancer at various stages and grades were evaluated by area under the curve in ROC curve analysis with DC and RMSN (N=36) as the control group. Table 10 lists the top diagnostic formulas and shows their diagnostic performances. The genes selected frequently in the formulas with high diagnostic performances are KRT17, SLC2A1, ALDOB, LINC00967, SLC16A9, CRH, PCAT4, AQP3, THAP7, FADS2, SERPINEL AS1, OLFM3, S100A13, C5orf30, GINM1, GPRC5A and TOP1P1. The combination of genes "ALDOB+CRH+SERPINE1+SLC2A1" showed the best performance to detect bladder cancer, especially for detection of lower stage and/or grade tumors (e.g., AUC 0.631 for pTa, AUC 0.822 for pTis, AUC 0.886 for pT1, AUC 0.798 for >pT2 tumors) (Table 10, FIG. 5A). This formula was further evaluated for cytology negative cancer detection (FIG. 5B) and for recurrent cancer detection (FIG. 5C), and was found to maintain good diagnostic performances under both situations. Therefore, the formula is a promising diagnostic that can be used complementarily to the conventional urine cytology test and can be used as well in monitoring for recurrent bladder cancer.

Figure 6A:
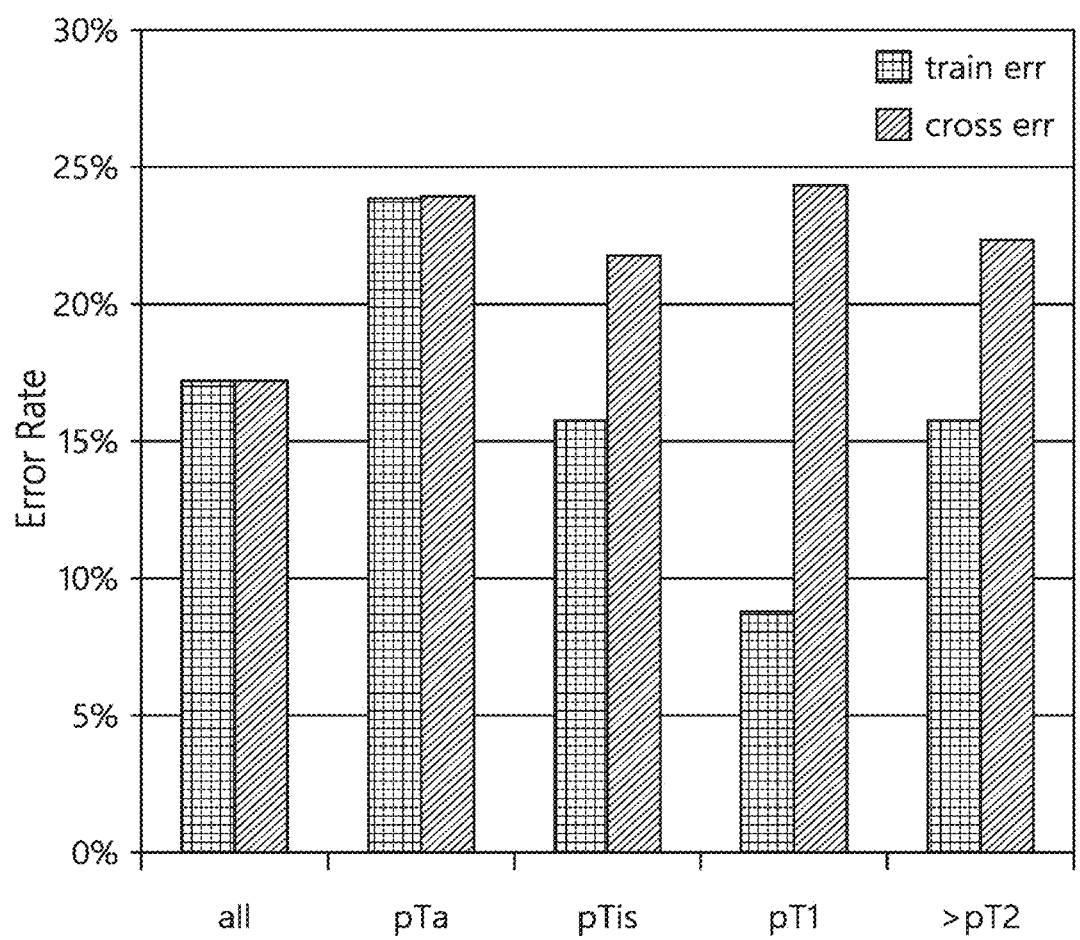
FIG. 6A depicts error rate of SVM to detect bladder cancer at various stages and grades with automatic parameter selection.
Figure 6C:
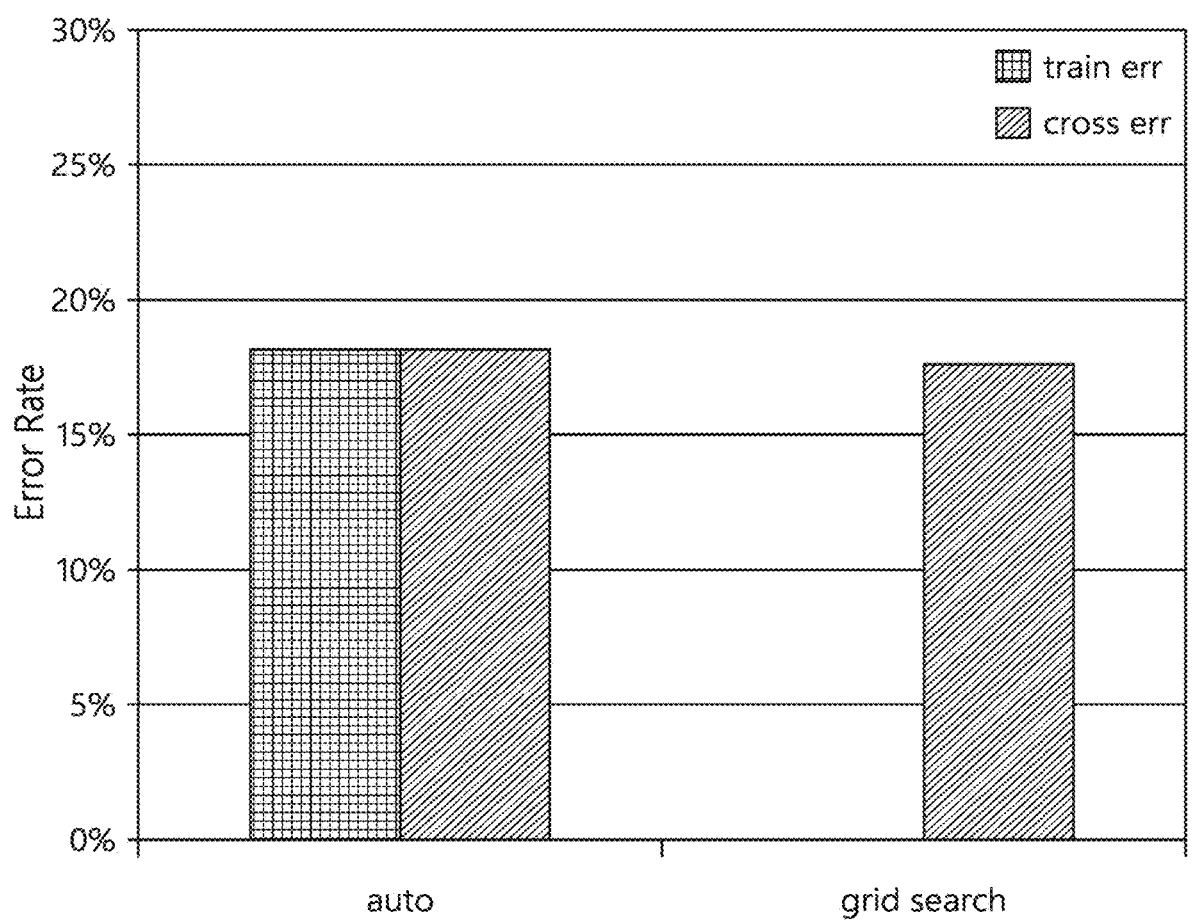
FIG. 6C depicts error rate of SVM to detect bladder cancer at various stages and grades with the optimized parameters (c=$2^{0.60}$ to $2^{0.94}$ Sigma=$2^{-4.5}$ to $2^{-3.5}$), training and cross validation errors were 0%±0% and 17.65%±0.03%, respectively.

Support vector machine (SVM) was applied using the urinary EMV mRNA raw Ct data to develop diagnostic formula for detecting bladder cancer. SVM can fit the data using various linear and non-linear functions. A non-linear radial basis function (RBF) was selected because of its generally superior classification performance. RBF requires tuning two parameters (c and sigma) to obtain the best result, although the package can estimate relatively optimum parameters automatically. SVM with automatic parameter selection was first applied to detect bladder cancer at various stages and grades (FIG. 6A). The training errors were 9% to 24% and the cross validation errors were 17% to 24%. In order to improve the diagnostic formula for non-muscle invasive bladder cancer including pTa, pTis and pT1, a grid search was conducted in order to obtain the best combination of parameters, c and sigma, through 10 repeats of 5-fold cross validation (FIG. 6B). With the optimized parameters ($c=2^{0.60}$ to $2^{0.94}$, sigma=$2^{-4.5}$ to $2^{-3.5}$), training and cross validation errors were 0%±0% and 17.65%±0.03%, respectively, both of which were improved further in comparison with the automatic parameter selection (FIG. 6C). These data indicate that bladder cancer can be detected accurately by SVM using the urinary EMV mRNA expression profiles. The methods and systems of the present disclosure use urinary EMV mRNA to achieve promising non-invasive biomarkers of urothelial cancer.

The present application identifies novel methods for using urinary EMV to diagnose, treat, and monitor urothelial cancer. While others performed a small scale screening study of bladder cancer markers using urinary EMV and identified several marker candidates, the marker candidates disclosed herein were not reported in that study. This may be because the other study was limited due to the low recovery yields of total RNA from patient urine samples. The present application investigated the expression profiles of the genes detected by the other study, but none of those reported markers appeared promising to detect and/or distinguish urothelial cancers unlike the ones identified herein.

As discussed above, there are provided herein several embodiments in which nucleic acids are evaluated from blood or urine samples in order to detect and determine an expression level of a particular marker. In several embodiments, the determination of the expression of the marker allows a diagnosis of a disease or condition, for example urothelial disease. In several embodiments, the determination is used to measure the severity of the condition and develop and implement an appropriate treatment plan. In several embodiments, the detected biomarker is then used to develop an appropriate treatment regimen. In several embodiments, however, the treatment may be taking no further action (e.g., not instituting a treatment), for example when a subject is in remission. In several embodiments the methods are computerized (e.g., one or more of the RNA isolation, cDNA generation, or amplification are controlled, in whole or in part, by a computer). In several embodiments, the detection of the biomarker is real time.

As above, certain aspects of the methods are optionally computerized. Also, in several embodiments, the amount of expression may result in a determination that no treatment is to be undertaken at that time. Thus, in several embodiments, the methods disclosed herein also reduce unnecessary medical expenses and reduce the likelihood of adverse effects from a treatment that is not needed at that time.

In some embodiments, after a biological sample is collected (e.g., a urine sample), membrane particles, cells, exosomes, exosome-like vesicles, microvesicles and/or other biological components of interest are isolated by filtering the sample. In some embodiments, filtering the collected sample will trap one or more of membrane particles, exosomes, exosome-like vesicles, and microvesicles on a filter.

In some embodiments, after a biological sample is collected (e.g., a urine sample), membrane particles, cells, exosomes, exosome-like vesicles, microvesicles and/or other biological components of interest are isolated by filtering the sample. In some embodiments, filtering the collected sample will trap one or more of membrane particles, exosomes, exosome-like vesicles, and microvesicles on a filter. In some embodiments, the vesicle-capturing material captures desired vesicles from a biological sample. In some embodiments, therefore, the vesicle-capturing material is selected based on the pore (or other passages through a vesicle-capturing material) size of the material. In some embodiments, the vesicle-capturing material comprises a filter.

In some embodiments, the filter comprises pores. As used herein, the terms "pore" or "pores" shall be given their ordinary meaning and shall also refer to direct or convoluted passageways through a vesicle-capture material. In some embodiments, the materials that make up the filter provide indirect passageways through the filter. For example, in some embodiments, the vesicle-capture material comprises a plurality of fibers, which allow passage of certain substances through the gaps in the fiber, but do not have pores per se. For instance, a glass fiber filter can have a mesh-like structure that is configured to retain particles that have a size of about 1.6 microns or greater in diameter. Such a glass fiber filter may be referred to herein interchangeably as having a pore size of 1.6 microns or as comprising material to capture components that are about 1.6 microns or greater in diameter. However, as discussed above, the EMV that are captured by the filter are orders of magnitude smaller than the pore size of the glass filter. Thus, although the filter may be described herein as comprising material to capture components that are about 1.6 microns or greater in diameter, such a filter may capture components (e.g., EMV) that have a smaller diameter because these small components may adsorb to the filter.

In some embodiments, the filter comprises material to capture components that are about 1.6 microns or greater in diameter. In several embodiments, a plurality of filters are used to capture vesicles within a particularly preferred range of sizes (e.g., diameters). For example, in several embodiments, filters are used to capture vesicles having a diameter of from about 0.2 microns to about 1.6 microns in diameter, including about 0.2 microns to about 0.4 microns, about 0.4 microns to about 0.6 microns, about 0.6 microns to about 0.8 microns, about 0.8 microns to about 1.0 microns, about 1.0 microns to about 1.2 microns, about 1.2 to about 1.4 microns, about 1.4 microns to about 1.6 microns (and any size in between those listed). In other embodiments, the vesicle-capture material captures exosomes ranging in size from about 0.5 microns to about 1.0 microns.

In some embodiments, the filter (or filters) comprises glass-like material, non-glass-like material, or a combination thereof. In some embodiments, wherein the vesicle-capture material comprises glass-like materials, the vesicle-capture material has a structure that is disordered or "amorphous" at the atomic scale, like plastic or glass. Glass-like materials include, but are not limited to glass beads or fibers, silica beads (or other configuration), nitrocellulose, nylon, polyvinylidene fluoride (PVDF) or other similar polymers, metal or nano-metal fibers, polystyrene, ethylene vinyl acetate or other co-polymers, natural fibers (e.g., silk), alginate fiber, or combinations thereof. In certain embodiments, the vesicle-capture material optionally comprises a plurality of layers of vesicle-capture material. In other embodiments, the vesicle-capture material further comprises nitrocellulose.

In some embodiments, a filter device is used to isolate biological components of interest. In some embodiments, the device comprises: a first body having an inlet, an outlet, and an interior volume between the inlet and the outlet; a second body having an inlet, an outlet, an interior volume between the inlet and the outlet, a filter material positioned within the interior volume of the second body and in fluid communication with the first body; and a receiving vessel having an inlet, a closed end opposite the inlet and interior cavity. In some embodiments, the first body and the second body are reversibly connected by an interaction of the inlet of the second body with the outlet of the first body. In some embodiments, the interior cavity of the receiving vessel is dimensioned to reversibly enclose both the first and the second body and to receive the collected sample after it is passed from the interior volume of the first body, through the filter material, through the interior cavity of the second body and out of the outlet of the second body. In some embodiments, the isolating step comprises placing at least a portion of the collected sample in such a device, and applying a force to the device to cause the collected sample to pass through the device to the receiving vessel and capture the biological component of interest. In some embodiments, applying the force comprises centrifugation of the device. In other embodiments, applying the force comprises application of positive pressure to the device. In other embodiments, applying the force comprises application of vacuum pressure to the device. Examples of such filter devices are disclosed in PCT Publication WO 2014/182330 and PCT Publication WO 2015/050891, hereby incorporated by reference in their entirety.

In some embodiments, the collected sample is passed through multiple filters to isolate the biological component of interest. In other embodiments, isolating biological components comprises diluting the collected sample. In other embodiments, centrifugation may be used to isolate the biological components of interest. In some embodiments, multiple isolation techniques may be employed (e.g., combinations of filtration selection and/or density centrifugation). In some embodiments, the collected sample is separated into one or more samples after the isolating step.

In some embodiments, RNA is liberated from the biological component of interest for measurement. In some embodiments, liberating the RNA from the biological component of interest comprises lysing the membrane particles, exosomes, exosome-like vesicles, and/or microvesicles with a lysis buffer. In other embodiments, centrifugation may be employed. In some embodiments, the liberating is performed while the membrane particles, exosomes, exosome-like vesicles, microvesicles and/or other components of interest are immobilized on a filter. In some embodiments, the membrane particles, exosomes, exosome-like vesicles, microvesicles and/or other components of interest are isolated or otherwise separated from other components of the collected sample (and/or from one another—e.g., vesicles separated from exosomes).

According to various embodiments, various methods to quantify RNA are used, including Northern blot analysis, RNase protection assay, PCR, RT-PCR, real-time RT-PCR, other quantitative PCR techniques, RNA sequencing, nucleic acid sequence-based amplification, branched-DNA amplification, mass spectrometry, CHIP-sequencing, DNA or RNA microarray analysis and/or other hybridization microarrays. In some of these embodiments or alternative embodiments, after amplified DNA is generated, it is exposed to a probe complementary to a portion of a biomarker of interest.

In some embodiments, a computerized method is used to complete one or more of the steps. In some embodiments, the computerized method comprises exposing a reaction mixture comprising isolated RNA and/or prepared cDNA, a polymerase and gene-specific primers to a thermal cycle. In some embodiments, the thermal cycle is generated by a computer configured to control the temperature time, and cycle number to which the reaction mixture is exposed. In other embodiments, the computer controls only the time or only the temperature for the reaction mixture and an individual controls on or more additional variables. In some embodiments, a computer is used that is configured to receive data from the detecting step and to implement a program that detects the number of thermal cycles required for the biomarker to reach a pre-defined amplification threshold in order to identify whether a subject is suffering from a gynecological disease or condition. In still additional embodiments, the entire testing and detection process is automated.

For example, in some embodiments, RNA is isolated by a fully automated method, e.g., methods controlled by a computer processor and associated automated machinery. In one embodiment a biological sample, such as a urine sample, is collected and loaded into a receiving vessel that is placed into a sample processing unit. A user enters information into a data input receiver, such information related to sample identity, the sample quantity, and/or specific patient characteristics. In several embodiments, the user employs a graphical user interface to enter the data. In other embodiments, the data input is automated (e.g., input by bar code, QR code, or other graphical identifier). The user can then implement an RNA isolation protocol, for which the computer is configured to access an algorithm and perform associated functions to process the sample in order to isolate biological components, such as vesicles, and subsequently processed the vesicles to liberate RNA. In further embodiments, the computer implemented program can quantify the amount of RNA isolated and/or evaluate and purity. In such embodiments, should the quantity and/or purity surpass a minimum threshold, the RNA can be further processed, in an automated fashion, to generate complementary DNA (cDNA). cDNA can then be generated using established methods, such as for example, binding of a poly-A RNA tail to an oligo dT molecule and subsequent extension using an RNA polymerase. In other embodiments, if the quantity and/or purity fail to surpass a minimum threshold, the computer implemented program can prompt a user to provide additional biological sample(s).

Depending on the embodiment, the cDNA can be divided into individual subsamples, some being stored for later analysis and some being analyzed immediately. Analysis, in some embodiments comprises mixing a known quantity of the cDNA with a salt-based buffer, a DNA polymerase, and at least one gene specific primer to generate a reaction mixture. The cDNA can then be amplified using a predetermined thermal cycle program that the computer system is configured to implement. This thermal cycle, could optionally be controlled manually as well. After amplification (e.g., real-time PCR,), the computer system can assess the number of cycles required for a gene of interest (e.g. a marker of urothelial disease or condition) to surpass a particular threshold of expression. A data analysis processor can then use this assessment to calculate the amount of the gene of interest present in the original sample, and by comparison either to a different patient sample, a known control, or a combination thereof, expression level of the gene of interest can be calculated. A data output processor can provide this information, either electronically in another acceptable format, to a test facility and/or directly to a medical care provider. Based on this determination, the medical care provider can then determine if and how to treat a particular patient based on determining the presence of a urothelial disease or condition. In several embodiments, the expression data is generated in real time, and optionally conveyed to the medical care provider (or other recipient) in real time.

In several embodiments, a fully or partially automated method enables faster sample processing and analysis than manual testing methods. In certain embodiments, machines or testing devices may be portable and/or mobile such that a physician or laboratory technician may complete testing outside of a normal hospital or laboratory setting. In some embodiments, a portable assay device may be compatible with a portable device comprising a computer such as a cell phone or lap top that can be used to input the assay parameters to the assay device and/or receive the raw results of a completed test from the assay device for further processing. In some embodiments, a patient or other user may be able to use an assay device via a computer interface without the assistance of a laboratory technician or doctor. In these cases, the patient would have the option of performing the test "at-home." In certain of these embodiments, a computer with specialized software or programming may guide a patient to properly place a sample in the assay device and input data and information relating to the sample in the computer before ordering the tests to run. After all the tests have been completed, the computer software may automatically calculate the test results based on the raw data received from the assay device. The computer may calculate additional data by processing the results and, in some embodiments, by comparing the results to control information from a stored library of data or other sources via the internet or other means that supply the computer with additional information. The computer may then display an output to the patient (and/or the medical care provider, and/or a test facility) based on those results.

In some embodiments, a medical professional may be in need of genetic testing in order to diagnose, monitor and/or treat a patient. Thus, in several embodiments, a medical professional may order a test and use the results in making a diagnosis or treatment plan for a patient. For example, in some embodiments a medical professional may collect a sample from a patient or have the patient otherwise provide a sample (or samples) for testing. The medical professional may then send the sample to a laboratory or other third party capable of processing and testing the sample. Alternatively, the medical professional may perform some or all of the processing and testing of the sample himself/herself (e.g., in house). Testing may provide quantitative and/or qualitative information about the sample, including data related to the presence of a urothelial disease. Once this information is collected, in some embodiments the information may be compared to control information (e.g., to a baseline or normal population) to determine whether the test results demonstrate a difference between the patient's sample and the control. After the information is compared and analyzed, it is returned to the medical professional for additional analysis. Alternatively, the raw data collected from the tests may be returned to the medical professional so that the medical professional or other hospital staff can perform any applicable comparisons and analyses. Based on the results of the tests and the medical professional's analysis, the medical professional may decide how to treat or diagnose the patient (or optionally refrain from treating).

In several embodiments, filtration (alone or in combination with centrifugation) is used to capture vesicles of different sizes. In some embodiments, differential capture of vesicles is made based on the surface expression of protein markers. For example, a filter may be designed to be reactive to a specific surface marker (e.g., filter coupled to an antibody) or specific types of vesicles or vesicles of different origin. In several embodiments, the combination of filtration and centrifugation allows a higher yield or improved purity of vesicles.

In some embodiments, the markers are unique vesicle proteins or peptides. In some embodiments, the severity of a particular gynecological disease or disorder is associated with certain vesicle modifications which can be exploited to allow isolation of particular vesicles. Modification may include, but is not limited to addition of lipids, carbohydrates, and other molecules such as acylated, formylated, lipoylated, myristolylated, palmitoylated, alkylated, methylated, isoprenylated, prenylated, amidated, glycosylated, hydroxylated, iodinated, adenylated, phosphorylated, sulfated, and selenoylated, ubiquitinated. In some embodiments, the vesicle markers comprise non-proteins such as lipids, carbohydrates, nucleic acids, RNA, DNA, etc.

In several embodiments, the specific capture of vesicles based on their surface markers also enables a "dip stick" format where each different type of vesicle is captured by dipping probes coated with different capture molecules (e.g., antibodies with different specificities) into a patient sample.

Free extracellular RNA is quickly degraded by nucleases, making it a potentially poor diagnostic marker. As described above, some extracellular RNA is associated with particles or vesicles that can be found in various biological samples, such as urine. This vesicle associated RNA, which includes mRNA, is protected from the degradation processes. Microvesicles are shed from most cell types and consist of fragments of plasma membrane. Microvesicles contain RNA, mRNA, microRNA, and proteins and mirror the composition of the cell from which they are shed. Exosomes are small microvesicles secreted by a wide range of mammalian cells and are secreted under normal and pathological conditions. These vesicles contain certain proteins and RNA including mRNA and microRNA. Several embodiments evaluate nucleic acids such as small interfering RNA (siRNA), tRNA, and small activating RNA (saRNA), among others.

In several embodiments the RNA isolated from vesicles from the urine of a patient is used as a template to make complementary DNA (cDNA), for example through the use of a reverse transcriptase. In several embodiments, cDNA is amplified using the polymerase chain reaction (PCR). In other embodiments, amplification of nucleic acid and RNA may also be achieved by any suitable amplification technique such as nucleic acid based amplification (NASBA) or primer-dependent continuous amplification of nucleic acid, or ligase chain reaction. Other methods may also be used to quantify the nucleic acids, such as for example, including Northern blot analysis, RNAse protection assay, RNA sequencing, RT-PCR, real-time RT-PCR, nucleic acid sequence-based amplification, branched-DNA amplification, ELISA, mass spectrometry, CHIP-sequencing, and DNA or RNA microarray analysis.

In several embodiments, mRNA is quantified by a method entailing cDNA synthesis from mRNA and amplification of cDNA using PCR. In one preferred embodiment, a multi-well filterplate is washed with lysis buffer and wash buffer. A cDNA synthesis buffer is then added to the multi-well filterplate. The multi-well filterplate can be centrifuged. PCR primers are added to a PCR plate, and the cDNA is transferred from the multi-well filterplate to the PCR plate. The PCR plate is centrifuged, and real time PCR is commenced.

Another preferred embodiment comprises application of specific antisense primers during mRNA hybridization or during cDNA synthesis. It is preferable that the primers be added during mRNA hybridization, so that excess antisense primers may be removed before cDNA synthesis to avoid carryover effects. The oligo(dT) and the specific primer (NNNN) simultaneously prime cDNA synthesis at different locations on the poly-A RNA. The specific primer (NNNN) and oligo(dT) cause the formation of cDNA during amplification. Even when the specific primer-derived cDNA is removed from the GenePlate by heating each well, the amounts of specific cDNA obtained from the heat denaturing process (for example, using TaqMan quantitative PCR) is similar to the amount obtained from an un-heated negative control. This allows the heat denaturing process to be completely eliminated. Moreover, by adding multiple antisense primers for different targets, multiple genes can be amplified from the aliquot of cDNA, and oligo(dT)-derived cDNA in the GenePlate can be stored for future use.

Another alternative embodiment involves a device for high-throughput quantification of mRNA from urine (or other fluids). The device includes a multi-well filterplate containing: multiple sample-delivery wells, an exosome-capturing filter (or filter directed to another biological component of interest) underneath the sample-delivery wells, and an mRNA capture zone under the filter, which contains oligo(dT)-immobilized in the wells of the mRNA capture zone. In order to increase the efficiency of exosome collection, several filtration membranes can be layered together.

In some embodiments, amplification comprises conducting real-time quantitative PCR (TaqMan) with exosome-derived RNA and control RNA. In some embodiments, a Taqman assay is employed. The 5' to 3' exonuclease activity of Taq polymerase is employed in a polymerase chain reaction product detection system to generate a specific detectable signal concomitantly with amplification. An oligonucleotide probe, nonextendable at the 3' end, labeled at the 5' end, and designed to hybridize within the target sequence, is introduced into the polymerase chain reaction assay. Annealing of the probe to one of the polymerase chain reaction product strands during the course of amplification generates a substrate suitable for exonuclease activity. During amplification, the 5' to 3' exonuclease activity of Taq polymerase degrades the probe into smaller fragments that can be differentiated from undegraded probe. In additional embodiments, the method comprises: (a) providing to a PCR assay containing a sample, at least one labeled oligonucleotide containing a sequence complementary to a region of the target nucleic acid, wherein the labeled oligonucleotide anneals within the target nucleic acid sequence bounded by the oligonucleotide primers of step (b); (b) providing a set of oligonucleotide primers, wherein a first primer contains a sequence complementary to a region in one strand of the target nucleic acid sequence and primes the synthesis of a complementary DNA strand, and a second primer contains a sequence complementary to a region in a second strand of the target nucleic acid sequence and primes the synthesis of a complementary DNA strand; and wherein each oligonucleotide primer is selected to anneal to its complementary template upstream of any labeled oligonucleotide annealed to the same nucleic acid strand; (c) amplifying the target nucleic acid sequence employing a nucleic acid polymerase having 5' to 3' nuclease activity as a template dependent polymerizing agent under conditions which are permissive for PCR cycling steps of (i) annealing of primers and labeled oligonucleotide to a template nucleic acid sequence contained within the target region, and (ii) extending the primer, wherein said nucleic acid polymerase synthesizes a primer extension product while the 5' to 3' nuclease activity of the nucleic acid polymerase simultaneously releases labeled fragments from the annealed duplexes comprising labeled oligonucleotide and its complementary template nucleic acid sequences, thereby creating detectable labeled fragments; and (d) detecting and/or measuring the release of labeled fragments to determine the presence or absence of target sequence in the sample.

In additional embodiments, a Taqman assay is employed that provides a reaction that results in the cleavage of single-stranded oligonucleotide probes labeled with a light-emitting label wherein the reaction is carried out in the presence of a DNA binding compound that interacts with the label to modify the light emission of the label. The method utilizes the change in light emission of the labeled probe that results from degradation of the probe. The methods are applicable in general to assays that utilize a reaction that results in cleavage of oligonucleotide probes, and in particular, to homogeneous amplification/detection assays where hybridized probe is cleaved concomitant with primer extension. A homogeneous amplification/detection assay is provided which allows the simultaneous detection of the accumulation of amplified target and the sequence-specific detection of the target sequence.

In additional embodiments, real-time PCR formats may also be employed. One format employs an intercalating dye, such as SYBR Green. This dye provides a strong fluorescent signal on binding double-stranded DNA; this signal enables quantification of the amplified DNA. Although this format does not permit sequence-specific monitoring of amplification, it enables direct quantization of amplified DNA without any labeled probes. Other such fluorescent dyes that may also be employed are SYBR Gold, YO-PRO dyes and Yo Yo dyes.

Another real-time PCR format that may be employed uses reporter probes that hybridize to amplicons to generate a fluorescent signal. The hybridization events either separate the reporter and quencher moieties on the probes or bring them into closer proximity. The probes themselves are not degraded and the reporter fluorescent signal itself is not accumulated in the reaction. The accumulation of products during PCR is monitored by an increase in reporter fluorescent signal when probes hybridize to amplicons. Formats in this category include molecular beacons, dual-hybe probes, Sunrise or Amplifluor, and Scorpion real-time PCR assays.

Another real-time PCR format that may also be employed is the so-called "Policeman" system. In this system, the primer comprises a fluorescent moiety, such as FAM, and a quencher moiety which is capable of quenching fluorescence of the fluorescent moiety, such as TAMRA, which is covalently bound to at least one nucleotide base at the 3' end of the primer. At the 3' end, the primer has at least one mismatched base and thus does not complement the nucleic acid sample at that base or bases. The template nucleic acid sequence is amplified by PCR with a polymerase having 3'-5' exonuclease activity, such as the Pfu enzyme, to produce a PCR product. The mismatched base(s) bound to the quencher moiety are cleaved from the 3' end of the PCR product by 3'-5' exonuclease activity. The fluorescence that results when the mismatched base with the covalently bound quencher moiety is cleaved by the polymerase, thus removing the quenching effect on the fluorescent moiety, is detected and/or quantified at least one time point during PCR. Fluorescence above background indicates the presence of the synthesized nucleic acid sample.

Another alternative embodiment involves a fully automated system for performing high throughput quantification of mRNA in biological fluid, such as urine, including: robots to apply urine samples, hypotonic buffer, and lysis buffer to the device; an automated vacuum aspirator and centrifuge, and automated PCR machinery.

The method of determining the presence of post-transplant kidney disease or condition disclosed may also employ other methods of measuring mRNA other than those described above. Other methods which may be employed include, for example, Northern blot analysis, Rnase protection, solution hybridization methods, semi-quantitative RT-PCR, and in situ hybridization.

In some embodiments, in order to properly quantify the amount of mRNA, quantification is calculated by comparing the amount of mRNA encoding a marker of urothelial disease or condition to a reference value. In some embodiments the reference value will be the amount of mRNA found in healthy non-diseased patients. In other embodiments, the reference value is the expression level of a house-keeping gene. In certain such embodiments, beta-actin, or other appropriate housekeeping gene is used as the reference value. Numerous other house-keeping genes that are well known in the art may also be used as a reference value. In other embodiments, a house keeping gene is used as a correction factor, such that the ultimate comparison is the expression level of marker from a diseased patient as compared to the same marker from a non-diseased (control) sample. In several embodiments, the house keeping gene is a tissue specific gene or marker, such as those discussed above. In still other embodiments, the reference value is zero, such that the quantification of the markers is represented by an absolute number. In several embodiments a ratio comparing the expression of one or more markers from a diseased patient to one or more other markers from a non-diseased person is made. In several embodiments, the comparison to the reference value is performed in real-time, such that it may be possible to make a determination about the sample at an early stage in the expression analysis. For example, if a sample is processed and compared to a reference value in real time, it may be determined that the expression of the marker exceeds the reference value after only a few amplification cycles, rather than requiring a full-length analysis. In several embodiments, this early comparison is particularly valuable, such as when a rapid diagnosis and treatment plan are required (e.g., to treat heavily damaged or malfunctioning kidneys prior to kidney failure or transplant rejection).

In alternative embodiments, the ability to determine the total efficiency of a given sample by using known amounts of spiked standard RNA results from embodiments being dose-independent and sequence-independent. The use of known amounts of control RNA allows PCR measurements to be converted into the quantity of target mRNAs in the original samples.

In some embodiments, a kit is provided for extracting target components from fluid sample, such as urine. In some embodiments, a kit comprises a capture device and additional items useful to carry out methods disclosed herein. In some embodiments, a kit comprises one or more reagents selected from the group consisting of lysis buffers, chaotropic reagents, washing buffers, alcohol, detergent, or combinations thereof. In some embodiments, kit reagents are provided individually or in storage containers. In several embodiments, kit reagents are provided ready-to-use. In some embodiments, kit reagents are provided in the form of stock solutions that are diluted before use. In some embodiments, a kit comprises plastic parts (optionally sterilized or sterilizable) that are useful to carry out methods herein disclosed. In some embodiments, a kit comprises plastic parts selected from the group consisting of racks, centrifuge tubes, vacuum manifolds, and multi-well plates. Instructions for use are also provided, in several embodiments.

In several embodiments, the analyses described herein are applicable to human patients, while in some embodiments, the methods are applicable to animals (e.g., veterinary diagnoses).

In several embodiments, presence of a urothelial condition or disease induces the altered expression of one or more markers. In several embodiments, the increased or decreased expression is measured by the amount of mRNA encoding said markers (in other embodiments, DNA or protein are used to measure expression levels). In some embodiments urine is collected from a patient and directly evaluated. In some embodiments, vesicles are concentrated, for example by use of filtration or centrifugation. Isolated vesicles are then incubated with lysis buffer to release the RNA from the vesicles, the RNA then serving as a template for cDNA which is quantified with methods such as quantitative PCR (or other appropriate amplification or quantification technique). In several embodiments, the level of specific marker RNA from patient vesicles is compared with a desired control such as, for example, RNA levels from a healthy patient population, or the RNA level from an earlier time point from the same patient or a control gene from the same patient.

Implementation Mechanisms

According to some embodiments, the methods described herein can be implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, server computer systems, portable computer systems, handheld devices, networking devices or any other device or combination of devices that incorporate hard-wired and/or program logic to implement the techniques.

Computing device(s) are generally controlled and coordinated by operating system software, such as iOS, Android, Chrome OS, Windows XP, Windows Vista, Windows 7, Windows 8, Windows Server, Windows CE, Unix, Linux, SunOS, Solaris, iOS, Blackberry OS, VxWorks, or other compatible operating systems. In other embodiments, the computing device may be controlled by a proprietary operating system. Conventional operating systems control and schedule computer processes for execution, perform memory management, provide file system, networking, I/O services, and provide a user interface functionality, such as a graphical user interface ("GUI"), among other things.

In some embodiments, the computer system includes a bus or other communication mechanism for communicating information, and a hardware processor, or multiple processors, coupled with the bus for processing information. Hardware processor(s) may be, for example, one or more general purpose microprocessors.

In some embodiments, the computer system may also includes a main memory, such as a random access memory (RAM), cache and/or other dynamic storage devices, coupled to a bus for storing information and instructions to be executed by a processor. Main memory also may be used for storing temporary variables or other intermediate information during execution of instructions to be executed by the processor. Such instructions, when stored in storage media accessible to the processor, render the computer system into a special-purpose machine that is customized to perform the operations specified in the instructions.

In some embodiments, the computer system further includes a read only memory (ROM) or other static storage device coupled to bus for storing static information and instructions for the processor. A storage device, such as a magnetic disk, optical disk, or USB thumb drive (Flash drive), etc., may be provided and coupled to the bus for storing information and instructions.

In some embodiments, the computer system may be coupled via a bus to a display, such as a cathode ray tube (CRT) or LCD display (or touch screen), for displaying information to a computer user. An input device, including alphanumeric and other keys, is coupled to the bus for communicating information and command selections to the processor. Another type of user input device is cursor control, such as a mouse, a trackball, or cursor direction keys for communicating direction information and command selections to the processor and for controlling cursor movement on display. This input device typically has two degrees of freedom in two axes, a first axis (e.g., x) and a second axis (e.g., y), that allows the device to specify positions in a plane. In some embodiments, the same direction information and command selections as cursor control may be implemented via receiving touches on a touch screen without a cursor.

In some embodiments, the computing system may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "module," as used herein, refers to logic embodied in hardware or firmware, or to a collection of software instructions, possibly having entry and exit points, written in a programming language, such as, for example, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules or computing device functionality described herein are preferably implemented as software modules, but may be represented in hardware or firmware. Generally, the modules described herein refer to logical modules that may be combined with other modules or divided into sub-modules despite their physical organization or storage In some embodiments, a computer system may implement the methods described herein using customized hard-wired logic, one or more ASICs or FPGAs, firmware and/or program logic which in combination with the computer system causes or programs the computer system to be a special-purpose machine. According to one embodiment, the methods herein are performed by the computer system in response to hardware processor(s) executing one or more sequences of one or more instructions contained in main memory. Such instructions may be read into main memory from another storage medium, such as a storage device. Execution of the sequences of instructions contained in main memory causes processor(s) to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, or other types of storage devices. Volatile media includes dynamic memory, such as a main memory. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between nontransitory media. For example, transmission media includes coaxial cables, copper wire and fiber optics, including the wires that comprise a bus. Transmission media can also take the form of acoustic or light waves, such as those generated during radio-wave and infra-red data communications.

Various forms of media may be involved in carrying one or more sequences of one or more instructions to a processor for execution. For example, the instructions may initially be carried on a magnetic disk or solid state drive of a remote computer. The remote computer can load the instructions into its dynamic memory and send the instructions over a telephone line using a modem or other network interface, such as a WAN or LAN interface. A modem local to a computer system can receive the data on the telephone line and use an infra-red transmitter to convert the data to an infra-red signal. An infra-red detector can receive the data carried in the infra-red signal and appropriate circuitry can place the data on a bus. The bus carries the data to the main memory, from which the processor retrieves and executes the instructions. The instructions received by the main memory may retrieve and execute the instructions. The instructions received by the main memory may optionally be stored on a storage device either before or after execution by the processor.

In some embodiments, the computer system may also include a communication interface coupled to a bus. The communication interface may provide a two-way data communication coupling to a network link that is connected to a local network. For example, a communication interface may be an integrated services digital network (ISDN) card, cable modem, satellite modem, or a modem to provide a data communication connection to a corresponding type of telephone line. As another example, a communication interface may be a local area network (LAN) card to provide a data communication connection to a compatible LAN (or WAN component to communicate with a WAN). Wireless links may also be implemented. In any such implementation, a communication interface sends and receives electrical, electromagnetic or optical signals that carry digital data streams representing various types of information.

A network link may typically provide data communication through one or more networks to other data devices. For example, a network link may provide a connection through a local network to a host computer or to data equipment operated by an Internet Service Provider (ISP). The ISP in turn provides data communication services through the world wide packet data communication network now commonly referred to as the "Internet." The local network and Internet both use electrical, electromagnetic or optical signals that carry digital data streams. The signals through the various networks and the signals on the network link and through a communication interface, which carry the digital data to and from the computer system, are example forms of transmission media.

In some embodiments, the computer system can send messages and receive data, including program code, through the network(s), the network link, and the communication interface. In the Internet example, a server might transmit a requested code for an application program through the Internet, ISP, local network, and communication interface.

The received code may be executed by a processor as it is received, and/or stored in a storage device, or other non-volatile storage for later execution.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "treating a subject for a disease or condition" include "instructing the administration of treatment of a subject for a disease or condition."

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments.

Terms, such as, "first", "second", "third", "fourth", "fifth", "sixth", "seventh", "eighth", "ninth", "tenth", or "eleventh" and more, unless specifically stated otherwise, or otherwise understood within the context as used, are generally intended to refer to any order, and not necessarily to an order based on the plain meaning of the corresponding ordinal number. Therefore, terms using ordinal numbers may merely indicate separate individuals and may not necessarily mean the order therebetween. Accordingly, for example, first and second biomarkers used in this application may mean that there are merely two sets of biomarkers.

In other words, there may not necessarily be any intention of order between the "first" and "second" sets of data in any aspects.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 nanometers" includes "10 nanometers."

TABLE 6

Diagnostic performance of urinary EMV mRNA for bladder cancer detection (control group = RMSN (N = 36)).

| Marker | All N = 173 | pTa N = 115 | pTis N = 10 | pT1 N = 37 | >pT2 N = 11 | G1 N = 4 | G2 N = 110 | G3 N = 59 |
|---|---|---|---|---|---|---|---|---|
| Cytology1 | 0.62 | 0.53 | 0.77 | 0.82 | 0.72 | 0.67 | 0.52 | 0.81 |
| Cytology2 | 0.63 | 0.54 | 0.73 | 0.81 | 0.72 | 0.72 | 0.53 | 0.79 |
| Cytology3 | 0.57 | 0.51 | 0.78 | 0.72 | 0.66 | 0.57 | 0.53 | 0.74 |
| BTA | 0.58 | 0.56 | 0.54 | 0.60 | 0.72 | 0.54 | 0.58 | 0.59 |
| SLC2A1 | 0.70 | 0.64 | 0.68 | 0.86 | 0.76 | 0.71 | 0.63 | 0.82 |
| S100A13 | 0.66 | 0.61 | 0.74 | 0.77 | 0.68 | 0.52 | 0.63 | 0.73 |
| GAPDH | 0.65 | 0.58 | 0.60 | 0.85 | 0.75 | 0.69 | 0.59 | 0.75 |
| KRT17 | 0.64 | 0.57 | 0.62 | 0.82 | 0.90 | 0.64 | 0.59 | 0.75 |
| GPRC5A | 0.64 | 0.56 | 0.80 | 0.85 | 0.72 | 0.59 | 0.58 | 0.77 |
| P4HA1 | 0.63 | 0.58 | 0.53 | 0.82 | 0.71 | 0.51 | 0.60 | 0.70 |
| AQP3 | 0.63 | 0.55 | 0.66 | 0.79 | 0.81 | 0.60 | 0.57 | 0.74 |
| SLC12A3 | 0.62 | 0.63 | 0.61 | 0.61 | 0.63 | 0.76 | 0.62 | 0.62 |
| TMPRSS4 | 0.62 | 0.56 | 0.67 | 0.78 | 0.66 | 0.60 | 0.59 | 0.68 |
| SLC12A1 | 0.62 | 0.61 | 0.59 | 0.66 | 0.63 | 0.54 | 0.62 | 0.62 |
| UPK1B | 0.61 | 0.57 | 0.66 | 0.69 | 0.80 | 0.55 | 0.58 | 0.68 |
| FABP4 | 0.61 | 0.58 | 0.68 | 0.67 | 0.67 | 0.69 | 0.58 | 0.67 |
| SMCR8 | 0.61 | 0.60 | 0.55 | 0.65 | 0.61 | 0.61 | 0.62 | 0.58 |
| DHRS2 | 0.61 | 0.60 | 0.64 | 0.61 | 0.64 | 0.64 | 0.61 | 0.62 |
| ACTB | 0.61 | 0.55 | 0.56 | 0.76 | 0.70 | 0.63 | 0.56 | 0.69 |
| FADS2 | 0.60 | 0.55 | 0.62 | 0.71 | 0.63 | 0.60 | 0.55 | 0.69 |
| CHEK1 | 0.59 | 0.55 | 0.69 | 0.70 | 0.64 | 0.54 | 0.57 | 0.66 |
| TPX2 | 0.59 | 0.53 | 0.62 | 0.76 | 0.70 | 0.57 | 0.53 | 0.71 |
| TOP1P1 | 0.59 | 0.55 | 0.63 | 0.64 | 0.80 | 0.67 | 0.57 | 0.63 |
| CASP7 | 0.59 | 0.56 | 0.63 | 0.67 | 0.60 | 0.68 | 0.54 | 0.67 |
| LINC00967 | 0.59 | 0.51 | 0.85 | 0.75 | 0.61 | 0.53 | 0.54 | 0.69 |
| KCNJ15 | 0.59 | 0.56 | 0.52 | 0.70 | 0.59 | 0.65 | 0.57 | 0.62 |
| HSD17B2 | 0.59 | 0.53 | 0.63 | 0.75 | 0.63 | 0.63 | 0.55 | 0.64 |
| GINM1 | 0.58 | 0.54 | 0.59 | 0.72 | 0.57 | 0.67 | 0.54 | 0.67 |
| SLC2A3 | 0.58 | 0.52 | 0.60 | 0.76 | 0.64 | 0.65 | 0.54 | 0.65 |
| CRH | 0.58 | 0.50 | 0.77 | 0.78 | 0.62 | 0.53 | 0.51 | 0.71 |
| PPP2R5B | 0.58 | 0.55 | 0.53 | 0.68 | 0.64 | 0.81 | 0.55 | 0.62 |
| RNF39 | 0.58 | 0.52 | 0.62 | 0.71 | 0.66 | 0.52 | 0.53 | 0.68 |
| MYC | 0.58 | 0.51 | 0.74 | 0.71 | 0.65 | 0.73 | 0.52 | 0.67 |
| SHISA3 | 0.57 | 0.56 | 0.62 | 0.61 | 0.55 | 0.81 | 0.56 | 0.59 |
| SLC41A1 | 0.57 | 0.55 | 0.53 | 0.64 | 0.61 | 0.58 | 0.54 | 0.64 |
| NRSN2-AS1 | 0.57 | 0.55 | 0.63 | 0.61 | 0.66 | 0.73 | 0.54 | 0.62 |
| UPK1A | 0.57 | 0.55 | 0.61 | 0.59 | 0.63 | 0.67 | 0.56 | 0.60 |
| MCM9 | 0.56 | 0.51 | 0.54 | 0.70 | 0.60 | 0.68 | 0.52 | 0.62 |
| OLFM3 | 0.56 | 0.56 | 0.54 | 0.58 | 0.52 | 0.55 | 0.58 | 0.52 |
| ACSM2A | 0.56 | 0.59 | 0.57 | 0.53 | 0.61 | 0.61 | 0.59 | 0.51 |
| GLI3 | 0.55 | 0.54 | 0.50 | 0.55 | 0.73 | 0.63 | 0.54 | 0.58 |
| RWDD3 | 0.55 | 0.51 | 0.62 | 0.63 | 0.67 | 0.57 | 0.53 | 0.61 |
| C5orf30 | 0.55 | 0.51 | 0.63 | 0.64 | 0.61 | 0.61 | 0.53 | 0.59 |
| F3 | 0.55 | 0.51 | 0.52 | 0.65 | 0.68 | 0.68 | 0.51 | 0.61 |
| PLAT | 0.55 | 0.51 | 0.52 | 0.68 | 0.57 | 0.54 | 0.51 | 0.67 |
| LRRCC1 | 0.55 | 0.53 | 0.51 | 0.60 | 0.59 | 0.59 | 0.53 | 0.58 |
| THAP7-AS1 | 0.55 | 0.56 | 0.59 | 0.51 | 0.50 | 0.56 | 0.56 | 0.52 |
| UMOD | 0.54 | 0.54 | 0.63 | 0.54 | 0.54 | 0.65 | 0.54 | 0.53 |
| CA1 | 0.54 | 0.54 | 0.60 | 0.50 | 0.58 | 0.53 | 0.56 | 0.50 |
| BMP2 | 0.54 | 0.53 | 0.53 | 0.71 | 0.65 | 0.51 | 0.51 | 0.60 |
| PRDM16 | 0.54 | 0.53 | 0.52 | 0.58 | 0.54 | 0.67 | 0.51 | 0.58 |
| BANK1 | 0.54 | 0.55 | 0.67 | 0.53 | 0.60 | 0.52 | 0.56 | 0.50 |
| CDCA3 | 0.53 | 0.51 | 0.63 | 0.54 | 0.66 | 0.53 | 0.52 | 0.56 |
| SLC16A9 | 0.53 | 0.50 | 0.54 | 0.60 | 0.69 | 0.76 | 0.52 | 0.54 |
| ZBTB42 | 0.53 | 0.51 | 0.55 | 0.53 | 0.65 | 0.53 | 0.51 | 0.58 |
| TMEM45A | 0.52 | 0.52 | 0.56 | 0.63 | 0.55 | 0.51 | 0.51 | 0.59 |
| SERPINE1 | 0.52 | 0.53 | 0.56 | 0.67 | 0.55 | 0.69 | 0.52 | 0.60 |
| PCAT4 | 0.52 | 0.50 | 0.51 | 0.59 | 0.56 | 0.71 | 0.51 | 0.53 |
| CECR2 | 0.52 | 0.53 | 0.58 | 0.59 | 0.69 | 0.65 | 0.52 | 0.58 |
| CEACAM7 | 0.50 | 0.52 | 0.51 | 0.54 | 0.57 | 0.55 | 0.50 | 0.50 |
| ZNF174 | 0.50 | 0.53 | 0.51 | 0.58 | 0.54 | 0.57 | 0.50 | 0.50 |
| ALDOB | 0.50 | 0.50 | 0.50 | 0.50 | 0.50 | 0.50 | 0.50 | 0.50 |
| BKPyVgp4 | 0.50 | 0.50 | 0.50 | 0.50 | 0.50 | 0.50 | 0.50 | 0.50 |
| GPC5 | 0.50 | 0.50 | 0.50 | 0.50 | 0.50 | 0.50 | 0.50 | 0.50 |

TABLE 7

Diagnostic performance of urinary EMV mRNA for bladder cancer detection in urine-cytology-negative or suspicious population (control group DC/RMSN (N = 26)).

| Marker | All N = 115 | pTa N = 92 | pTis N = 3 | pT1 N = 15 | >pT2 N = 5 | G1 N = 3 | G2 N = 90 | G3 N = 22 |
|---|---|---|---|---|---|---|---|---|
| Cytology1 | 0.59 | 0.56 | 0.56 | 0.78 | 0.64 | 0.78 | 0.55 | 0.72 |
| Cytology2 | 0.59 | 0.56 | 0.56 | 0.78 | 0.64 | 0.78 | 0.55 | 0.72 |
| Cytology3 | 0.50 | 0.50 | 0.50 | 0.50 | 0.50 | 0.50 | 0.50 | 0.50 |
| BTA | 0.56 | 0.56 | 0.62 | 0.53 | 0.63 | 0.58 | 0.57 | 0.52 |
| SLC2A1 | 0.68 | 0.64 | 0.87 | 0.84 | 0.67 | 0.88 | 0.63 | 0.83 |
| S100A13 | 0.68 | 0.66 | 0.87 | 0.78 | 0.60 | 0.62 | 0.66 | 0.73 |
| SMCR8 | 0.64 | 0.63 | 0.67 | 0.74 | 0.78 | 0.62 | 0.66 | 0.58 |
| GAPDH | 0.64 | 0.60 | 0.64 | 0.86 | 0.79 | 0.77 | 0.62 | 0.70 |
| FABP4 | 0.63 | 0.60 | 0.79 | 0.75 | 0.68 | 0.64 | 0.60 | 0.73 |
| DHRS2 | 0.62 | 0.62 | 0.51 | 0.62 | 0.79 | 0.62 | 0.64 | 0.60 |
| ACTB | 0.62 | 0.59 | 0.60 | 0.79 | 0.81 | 0.64 | 0.60 | 0.71 |
| BANK1 | 0.62 | 0.62 | 0.65 | 0.62 | 0.76 | 0.53 | 0.64 | 0.56 |
| GPRC5A | 0.62 | 0.57 | 0.81 | 0.86 | 0.65 | 0.51 | 0.60 | 0.72 |
| SHISA3 | 0.62 | 0.62 | 0.56 | 0.67 | 0.52 | 0.85 | 0.61 | 0.61 |
| TMPRSS4 | 0.61 | 0.58 | 0.51 | 0.82 | 0.57 | 0.53 | 0.61 | 0.61 |
| SLC12A3 | 0.60 | 0.62 | 0.51 | 0.58 | 0.55 | 0.76 | 0.61 | 0.55 |
| SLC12A1 | 0.60 | 0.60 | 0.62 | 0.66 | 0.57 | 0.51 | 0.61 | 0.56 |
| P4HA1 | 0.60 | 0.57 | 0.69 | 0.78 | 0.67 | 0.51 | 0.61 | 0.58 |
| UPK1A | 0.58 | 0.59 | 0.53 | 0.53 | 0.74 | 0.64 | 0.60 | 0.56 |
| KCNJ15 | 0.58 | 0.57 | 0.54 | 0.73 | 0.55 | 0.63 | 0.58 | 0.60 |
| UPK1B | 0.58 | 0.57 | 0.63 | 0.60 | 0.90 | 0.65 | 0.58 | 0.56 |
| SLC41A1 | 0.58 | 0.58 | 0.69 | 0.66 | 0.54 | 0.50 | 0.57 | 0.63 |
| ACSM2A | 0.57 | 0.57 | 0.79 | 0.52 | 0.68 | 0.60 | 0.58 | 0.58 |
| TOP1P1 | 0.57 | 0.55 | 0.59 | 0.63 | 0.74 | 0.60 | 0.58 | 0.54 |
| KRT17 | 0.57 | 0.53 | 0.60 | 0.74 | 0.89 | 0.53 | 0.56 | 0.61 |
| FADS2 | 0.57 | 0.55 | 0.60 | 0.68 | 0.63 | 0.60 | 0.56 | 0.60 |
| RNF39 | 0.56 | 0.54 | 0.54 | 0.69 | 0.62 | 0.58 | 0.54 | 0.65 |
| CHEK1 | 0.56 | 0.56 | 0.62 | 0.55 | 0.65 | 0.54 | 0.58 | 0.52 |
| AQP3 | 0.56 | 0.53 | 0.58 | 0.73 | 0.75 | 0.52 | 0.55 | 0.64 |
| C5orf30 | 0.56 | 0.56 | 0.60 | 0.57 | 0.64 | 0.63 | 0.57 | 0.50 |
| RWDD3 | 0.56 | 0.55 | 0.50 | 0.65 | 0.58 | 0.61 | 0.56 | 0.56 |
| CASP7 | 0.56 | 0.55 | 0.54 | 0.66 | 0.53 | 0.64 | 0.54 | 0.61 |
| SLC2A3 | 0.56 | 0.52 | 0.58 | 0.76 | 0.71 | 0.66 | 0.55 | 0.59 |
| CA1 | 0.56 | 0.55 | 0.76 | 0.56 | 0.58 | 0.53 | 0.57 | 0.53 |
| NRSN2-AS1 | 0.55 | 0.55 | 0.51 | 0.59 | 0.53 | 0.70 | 0.55 | 0.57 |
| PRDM16 | 0.55 | 0.55 | 0.58 | 0.64 | 0.56 | 0.69 | 0.55 | 0.56 |
| PPP2R5B | 0.55 | 0.55 | 0.60 | 0.59 | 0.53 | 0.86 | 0.54 | 0.53 |
| GLI3 | 0.55 | 0.54 | 0.50 | 0.57 | 0.70 | 0.50 | 0.54 | 0.59 |
| TPX2 | 0.55 | 0.51 | 0.52 | 0.72 | 0.69 | 0.52 | 0.53 | 0.62 |
| ZNF174 | 0.54 | 0.53 | 0.51 | 0.65 | 0.55 | 0.55 | 0.56 | 0.51 |
| OLFM3 | 0.54 | 0.54 | 0.51 | 0.56 | 0.54 | 0.71 | 0.56 | 0.53 |
| BMP2 | 0.54 | 0.51 | 0.51 | 0.73 | 0.68 | 0.53 | 0.53 | 0.58 |
| MCM9 | 0.54 | 0.52 | 0.55 | 0.67 | 0.51 | 0.66 | 0.53 | 0.58 |
| LINC00967 | 0.54 | 0.51 | 0.75 | 0.65 | 0.64 | 0.59 | 0.53 | 0.58 |
| F3 | 0.54 | 0.52 | 0.63 | 0.63 | 0.70 | 0.69 | 0.53 | 0.58 |
| SERPINE1 | 0.54 | 0.57 | 0.54 | 0.62 | 0.59 | 0.67 | 0.55 | 0.50 |
| THAP7-AS1 | 0.54 | 0.55 | 0.55 | 0.55 | 0.58 | 0.51 | 0.54 | 0.53 |
| GINM1 | 0.54 | 0.52 | 0.59 | 0.69 | 0.54 | 0.66 | 0.52 | 0.57 |
| UMOD | 0.53 | 0.53 | 0.56 | 0.56 | 0.51 | 0.62 | 0.55 | 0.52 |
| PCAT4 | 0.53 | 0.54 | 0.53 | 0.51 | 0.56 | 0.67 | 0.55 | 0.53 |
| MYC | 0.53 | 0.50 | 0.55 | 0.69 | 0.52 | 0.71 | 0.51 | 0.58 |
| LRRCC1 | 0.52 | 0.53 | 0.63 | 0.54 | 0.52 | 0.59 | 0.52 | 0.55 |
| TMEM45A | 0.52 | 0.50 | 0.54 | 0.64 | 0.50 | 0.59 | 0.51 | 0.58 |
| CRH | 0.52 | 0.50 | 0.56 | 0.62 | 0.65 | 0.58 | 0.50 | 0.61 |
| HSD17B2 | 0.52 | 0.51 | 0.51 | 0.68 | 0.63 | 0.72 | 0.51 | 0.52 |
| SLC16A9 | 0.52 | 0.50 | 0.54 | 0.58 | 0.62 | 0.79 | 0.51 | 0.52 |
| PLAT | 0.52 | 0.50 | 0.58 | 0.60 | 0.54 | 0.58 | 0.50 | 0.59 |
| CDCA3 | 0.51 | 0.51 | 0.65 | 0.55 | 0.68 | 0.52 | 0.51 | 0.50 |
| CEACAM7 | 0.51 | 0.52 | 0.58 | 0.54 | 0.64 | 0.58 | 0.51 | 0.50 |
| ZBTB42 | 0.51 | 0.50 | 0.71 | 0.54 | 0.63 | 0.65 | 0.51 | 0.55 |
| CECR2 | 0.50 | 0.52 | 0.56 | 0.62 | 0.67 | 0.63 | 0.51 | 0.54 |
| ALDOB | 0.50 | 0.50 | 0.50 | 0.50 | 0.50 | 0.50 | 0.50 | 0.50 |
| BKPyVgp4 | 0.50 | 0.50 | 0.50 | 0.50 | 0.50 | 0.50 | 0.50 | 0.50 |
| GPC5 | 0.50 | 0.50 | 0.50 | 0.50 | 0.50 | 0.50 | 0.50 | 0.50 |

TABLE 8

Diagnostic performance of urinary EMV mRNA for bladder cancer detection in urine-cytology-negative or suspicious population (control group is RMSN (N = 27)).

| Marker | All N = 77 | pTa N = 67 | pTis N = 5 | pT1 N = 10 | >pT2 N = 0 | G1 N = 4 | G2 N = 59 | G3 N = 14 |
|---|---|---|---|---|---|---|---|---|
| Cytology1 | 0.51 | 0.52 | 0.62 | 0.64 | — | 0.70 | 0.53 | 0.58 |
| Cytology2 | 0.51 | 0.52 | 0.61 | 0.66 | — | 0.74 | 0.52 | 0.59 |
| Cytology3 | 0.53 | 0.55 | 0.63 | 0.51 | — | 0.57 | 0.55 | 0.54 |
| BTA | 0.55 | 0.53 | 0.66 | 0.60 | — | 0.53 | 0.55 | 0.55 |
| SLC12A3 | 0.70 | 0.69 | 0.64 | 0.75 | — | 0.82 | 0.69 | 0.68 |
| S100A13 | 0.64 | 0.61 | 0.72 | 0.76 | — | 0.53 | 0.62 | 0.72 |
| GPRC5A | 0.62 | 0.56 | 0.84 | 0.91 | — | 0.64 | 0.59 | 0.76 |
| KRT17 | 0.62 | 0.60 | 0.60 | 0.74 | — | 0.70 | 0.61 | 0.62 |
| SLC2A1 | 0.62 | 0.56 | 0.81 | 0.86 | — | 0.74 | 0.56 | 0.82 |
| SLC12A1 | 0.61 | 0.60 | 0.52 | 0.76 | — | 0.52 | 0.60 | 0.70 |
| SHISA3 | 0.61 | 0.61 | 0.50 | 0.68 | — | 0.86 | 0.59 | 0.65 |
| DHRS2 | 0.61 | 0.61 | 0.56 | 0.64 | — | 0.63 | 0.62 | 0.63 |
| UMOD | 0.60 | 0.56 | 0.77 | 0.72 | — | 0.70 | 0.56 | 0.74 |
| LRRCC1 | 0.59 | 0.60 | 0.51 | 0.55 | — | 0.63 | 0.59 | 0.58 |
| FABP4 | 0.58 | 0.56 | 0.64 | 0.66 | — | 0.71 | 0.56 | 0.63 |
| ACSM2A | 0.58 | 0.60 | 0.56 | 0.53 | — | 0.65 | 0.59 | 0.60 |
| SMCR8 | 0.58 | 0.57 | 0.61 | 0.76 | — | 0.65 | 0.59 | 0.53 |
| AQP3 | 0.58 | 0.57 | 0.61 | 0.64 | — | 0.64 | 0.55 | 0.67 |
| GAPDH | 0.58 | 0.55 | 0.51 | 0.80 | — | 0.66 | 0.54 | 0.70 |
| PPP2R5B | 0.57 | 0.59 | 0.60 | 0.56 | — | 0.89 | 0.56 | 0.52 |
| HSD17B2 | 0.57 | 0.56 | 0.50 | 0.67 | — | 0.68 | 0.58 | 0.52 |
| TOP1P1 | 0.57 | 0.56 | 0.55 | 0.66 | — | 0.70 | 0.56 | 0.56 |
| THAP7-AS1 | 0.57 | 0.58 | 0.63 | 0.51 | — | 0.56 | 0.57 | 0.57 |
| TPX2 | 0.56 | 0.53 | 0.57 | 0.78 | — | 0.58 | 0.54 | 0.65 |
| NRSN2-AS1 | 0.56 | 0.55 | 0.54 | 0.62 | — | 0.76 | 0.54 | 0.56 |
| SLC41A1 | 0.55 | 0.54 | 0.52 | 0.66 | — | 0.56 | 0.52 | 0.68 |
| UPK1A | 0.55 | 0.55 | 0.50 | 0.58 | — | 0.64 | 0.55 | 0.61 |
| KCNJ15 | 0.55 | 0.54 | 0.53 | 0.67 | — | 0.65 | 0.56 | 0.53 |
| ACTB | 0.55 | 0.53 | 0.51 | 0.70 | — | 0.63 | 0.54 | 0.59 |
| MYC | 0.55 | 0.53 | 0.70 | 0.60 | — | 0.76 | 0.52 | 0.61 |
| OLFM3 | 0.55 | 0.53 | 0.58 | 0.67 | — | 0.56 | 0.56 | 0.55 |
| C5orf30 | 0.55 | 0.54 | 0.56 | 0.57 | — | 0.61 | 0.55 | 0.54 |
| F3 | 0.54 | 0.55 | 0.61 | 0.56 | — | 0.74 | 0.54 | 0.50 |
| P4HA1 | 0.54 | 0.53 | 0.62 | 0.69 | — | 0.54 | 0.55 | 0.53 |
| CASP7 | 0.54 | 0.51 | 0.61 | 0.68 | — | 0.65 | 0.50 | 0.70 |
| LINC00967 | 0.54 | 0.52 | 0.83 | 0.52 | — | 0.57 | 0.53 | 0.57 |
| CHEK1 | 0.54 | 0.53 | 0.66 | 0.51 | — | 0.54 | 0.54 | 0.56 |
| SLC2A3 | 0.53 | 0.51 | 0.56 | 0.66 | — | 0.66 | 0.53 | 0.50 |
| CRH | 0.53 | 0.51 | 0.73 | 0.59 | — | 0.56 | 0.51 | 0.61 |
| TMPRSS4 | 0.53 | 0.51 | 0.64 | 0.73 | — | 0.60 | 0.50 | 0.64 |
| PRDM16 | 0.53 | 0.51 | 0.56 | 0.70 | — | 0.69 | 0.50 | 0.59 |
| GINM1 | 0.53 | 0.51 | 0.57 | 0.68 | — | 0.67 | 0.51 | 0.57 |
| ZNF174 | 0.52 | 0.54 | 0.53 | 0.56 | — | 0.59 | 0.53 | 0.53 |
| RWDD3 | 0.52 | 0.51 | 0.55 | 0.63 | — | 0.57 | 0.52 | 0.50 |
| CECR2 | 0.52 | 0.54 | 0.54 | 0.57 | — | 0.69 | 0.54 | 0.51 |
| FADS2 | 0.52 | 0.51 | 0.50 | 0.60 | — | 0.61 | 0.51 | 0.62 |
| GLI3 | 0.52 | 0.52 | 0.50 | 0.50 | — | 0.63 | 0.52 | 0.50 |
| SLC16A9 | 0.52 | 0.52 | 0.50 | 0.51 | — | 0.76 | 0.53 | 0.59 |
| BMP2 | 0.52 | 0.51 | 0.54 | 0.65 | — | 0.54 | 0.51 | 0.53 |
| CEACAM7 | 0.52 | 0.51 | 0.51 | 0.59 | — | 0.57 | 0.52 | 0.50 |
| SERPINE1 | 0.52 | 0.53 | 0.55 | 0.54 | — | 0.74 | 0.54 | 0.51 |
| MCM9 | 0.51 | 0.50 | 0.59 | 0.63 | — | 0.69 | 0.51 | 0.50 |
| TMEM45A | 0.51 | 0.51 | 0.51 | 0.56 | — | 0.54 | 0.50 | 0.55 |
| CDCA3 | 0.51 | 0.52 | 0.67 | 0.54 | — | 0.54 | 0.51 | 0.50 |
| UPK1B | 0.51 | 0.51 | 0.57 | 0.56 | — | 0.54 | 0.50 | 0.55 |
| PCAT4 | 0.51 | 0.53 | 0.60 | 0.60 | — | 0.70 | 0.54 | 0.56 |
| ZBTB42 | 0.50 | 0.50 | 0.54 | 0.53 | — | 0.52 | 0.53 | 0.65 |
| PLAT | 0.50 | 0.51 | 0.59 | 0.57 | — | 0.55 | 0.51 | 0.53 |
| BANK1 | 0.50 | 0.53 | 0.72 | 0.55 | — | 0.52 | 0.53 | 0.61 |
| CA1 | 0.50 | 0.51 | 0.54 | 0.57 | — | 0.51 | 0.52 | 0.59 |
| RNF39 | 0.50 | 0.52 | 0.56 | 0.59 | — | 0.51 | 0.51 | 0.52 |
| ALDOB | 0.50 | 0.50 | 0.50 | 0.50 | — | 0.50 | 0.50 | 0.50 |
| BKPyVgp4 | 0.50 | 0.50 | 0.50 | 0.50 | — | 0.50 | 0.50 | 0.50 |
| GPC5 | 0.50 | 0.50 | 0.50 | 0.50 | — | 0.50 | 0.50 | 0.50 |

TABLE 9

Diagnostic performance of urinary EMV mRNA for renal pelvis and ureter cancer detection (control group is DC/RMSN (N = 36)).

| Marker | All<br>N = 32 | pTa<br>N = 10 | pTis<br>N = 1 | pT1<br>N = 7 | >pT2<br>N = 14 | G1<br>N = 0 | G2<br>N = 13 | G3<br>N = 19 |
|---|---|---|---|---|---|---|---|---|
| Cytology1 | 0.64 | 0.70 | 0.93 | 0.79 | 0.52 | — | 0.68 | 0.61 |
| Cytology2 | 0.66 | 0.72 | 0.88 | 0.81 | 0.54 | — | 0.69 | 0.63 |
| Cytology3 | 0.51 | 0.54 | 0.93 | 0.58 | 0.57 | — | 0.55 | 0.51 |
| BTA | 0.60 | 0.58 | 1.00 | 0.56 | 0.58 | — | 0.64 | 0.57 |
| KRT17 | 0.77 | 0.66 | 0.97 | 0.87 | 0.78 | — | 0.75 | 0.78 |
| P4HA1 | 0.72 | 0.77 | 1.00 | 0.77 | 0.63 | — | 0.75 | 0.70 |
| HSD17B2 | 0.71 | 0.67 | 0.97 | 0.74 | 0.69 | — | 0.73 | 0.69 |
| SLC2A1 | 0.70 | 0.58 | 1.00 | 0.77 | 0.70 | — | 0.70 | 0.69 |
| S100A13 | 0.69 | 0.65 | 1.00 | 0.64 | 0.74 | — | 0.64 | 0.73 |
| GAPDH | 0.67 | 0.63 | 0.97 | 0.77 | 0.63 | — | 0.70 | 0.66 |
| MYC | 0.67 | 0.63 | 0.64 | 0.75 | 0.68 | — | 0.69 | 0.65 |
| KCNJ15 | 0.67 | 0.63 | 1.00 | 0.73 | 0.64 | — | 0.61 | 0.71 |
| SLC12A1 | 0.66 | 0.77 | 1.00 | 0.65 | 0.57 | — | 0.66 | 0.65 |
| GPRC5A | 0.66 | 0.60 | 0.75 | 0.74 | 0.67 | — | 0.66 | 0.65 |
| ACTB | 0.65 | 0.60 | 0.89 | 0.71 | 0.64 | — | 0.64 | 0.66 |
| F3 | 0.65 | 0.67 | 0.65 | 0.64 | 0.69 | — | 0.67 | 0.63 |
| SLC2A3 | 0.65 | 0.61 | 0.92 | 0.69 | 0.65 | — | 0.64 | 0.65 |
| TMEM45A | 0.64 | 0.58 | 1.00 | 0.58 | 0.71 | — | 0.58 | 0.69 |
| C5orf30 | 0.64 | 0.67 | 0.74 | 0.70 | 0.61 | — | 0.63 | 0.65 |
| BMP2 | 0.63 | 0.60 | 1.00 | 0.61 | 0.65 | — | 0.58 | 0.68 |
| FADS2 | 0.63 | 0.69 | 1.00 | 0.63 | 0.58 | — | 0.65 | 0.62 |
| RNF39 | 0.63 | 0.57 | 0.65 | 0.66 | 0.69 | — | 0.58 | 0.66 |
| FABP4 | 0.63 | 0.64 | 0.57 | 0.82 | 0.51 | — | 0.73 | 0.54 |
| DHRS2 | 0.61 | 0.60 | 1.00 | 0.60 | 0.59 | — | 0.60 | 0.63 |
| TMPRSS4 | 0.61 | 0.75 | 0.68 | 0.68 | 0.53 | — | 0.75 | 0.51 |
| CA1 | 0.61 | 0.68 | 0.67 | 0.80 | 0.53 | — | 0.69 | 0.55 |
| GLI3 | 0.61 | 0.65 | 0.50 | 0.57 | 0.61 | — | 0.64 | 0.58 |
| TOP1P1 | 0.61 | 0.67 | 0.58 | 0.55 | 0.58 | — | 0.60 | 0.61 |
| SHISA3 | 0.60 | 0.62 | 0.69 | 0.69 | 0.60 | — | 0.54 | 0.65 |
| UPK1B | 0.60 | 0.68 | 1.00 | 0.65 | 0.51 | — | 0.71 | 0.53 |
| UMOD | 0.60 | 0.64 | 1.00 | 0.60 | 0.53 | — | 0.61 | 0.59 |
| GINM1 | 0.60 | 0.65 | 0.75 | 0.65 | 0.58 | — | 0.60 | 0.60 |
| ZNF174 | 0.60 | 0.53 | 1.00 | 0.56 | 0.65 | — | 0.54 | 0.64 |
| SERPINE1 | 0.60 | 0.50 | 0.68 | 0.69 | 0.65 | — | 0.59 | 0.60 |
| AQP3 | 0.59 | 0.59 | 0.78 | 0.70 | 0.54 | — | 0.70 | 0.51 |
| PLAT | 0.59 | 0.58 | 0.60 | 0.80 | 0.52 | — | 0.61 | 0.58 |
| CRH | 0.59 | 0.58 | 0.58 | 0.58 | 0.63 | — | 0.53 | 0.64 |
| LINC00967 | 0.59 | 0.61 | 1.00 | 0.56 | 0.57 | — | 0.54 | 0.63 |
| SLC41A1 | 0.58 | 0.50 | 1.00 | 0.64 | 0.61 | — | 0.51 | 0.65 |
| MCM9 | 0.58 | 0.56 | 0.68 | 0.57 | 0.63 | — | 0.53 | 0.61 |
| NRSN2-AS1 | 0.57 | 0.70 | 0.69 | 0.55 | 0.59 | — | 0.61 | 0.55 |
| TPX2 | 0.57 | 0.62 | 0.54 | 0.54 | 0.57 | — | 0.57 | 0.57 |
| UPK1A | 0.57 | 0.51 | 1.00 | 0.58 | 0.57 | — | 0.54 | 0.59 |
| SLC16A9 | 0.57 | 0.52 | 1.00 | 0.59 | 0.59 | — | 0.51 | 0.61 |
| ACSM2A | 0.56 | 0.52 | 0.99 | 0.65 | 0.62 | — | 0.53 | 0.58 |
| CECR2 | 0.55 | 0.59 | 0.72 | 0.63 | 0.53 | — | 0.53 | 0.57 |
| PPP2R5B | 0.55 | 0.59 | 0.72 | 0.63 | 0.52 | — | 0.54 | 0.56 |
| THAP7-AS1 | 0.54 | 0.54 | 0.69 | 0.56 | 0.63 | — | 0.55 | 0.61 |
| ZBTB42 | 0.54 | 0.54 | 1.00 | 0.66 | 0.53 | — | 0.51 | 0.58 |
| CDCA3 | 0.54 | 0.53 | 0.53 | 0.55 | 0.59 | — | 0.53 | 0.58 |
| SLC12A3 | 0.53 | 0.58 | 1.00 | 0.77 | 0.55 | — | 0.53 | 0.57 |
| PRDM16 | 0.53 | 0.53 | 0.74 | 0.52 | 0.55 | — | 0.54 | 0.58 |
| RWDD3 | 0.53 | 0.54 | 1.00 | 0.57 | 0.57 | — | 0.51 | 0.54 |
| BANK1 | 0.52 | 0.53 | 0.97 | 0.54 | 0.51 | — | 0.55 | 0.51 |
| SMCR8 | 0.52 | 0.55 | 0.86 | 0.54 | 0.51 | — | 0.54 | 0.51 |
| CASP7 | 0.52 | 0.50 | 1.00 | 0.55 | 0.53 | — | 0.52 | 0.55 |
| CHEK1 | 0.52 | 0.51 | 0.54 | 0.54 | 0.53 | — | 0.53 | 0.51 |
| OLFM3 | 0.52 | 0.53 | 0.69 | 0.80 | 0.59 | — | 0.55 | 0.51 |
| PCAT4 | 0.51 | 0.55 | 0.97 | 0.62 | 0.50 | — | 0.52 | 0.54 |
| CEACAM7 | 0.51 | 0.69 | 0.58 | 0.52 | 0.58 | — | 0.60 | 0.55 |
| LRRCC1 | 0.51 | 0.53 | 0.79 | 0.50 | 0.54 | — | 0.52 | 0.53 |
| ALDOB | 0.50 | 0.50 | 0.50 | 0.50 | 0.50 | — | 0.50 | 0.50 |
| BKPyVgp4 | 0.50 | 0.50 | 0.50 | 0.50 | 0.50 | — | 0.50 | 0.50 |
| GPC5 | 0.50 | 0.50 | 0.50 | 0.50 | 0.50 | — | 0.50 | 0.50 |

TABLE 10

Diagnostic performance of urinary EMV mRNA formula.

| Formula | All N = 173 | pTa N = 115 | pTis N = 10 | pT1 N = 37 | >pT2 N = 11 | G1 N = 4 | G2 N = 110 | G3 N = 59 |
|---|---|---|---|---|---|---|---|---|
| ALDOB + CRH + SERPINE1 + SLC2A1 | 0.71 | 0.63 | 0.82 | 0.89 | 0.80 | 0.53 | 0.64 | 0.85 |
| ALDOB + CRH + SLC2A1 + THAP7.AS1 | 0.69 | 0.61 | 0.81 | 0.88 | 0.82 | 0.69 | 0.61 | 0.85 |
| CRH + SLC2A1 + THAP7.AS1 + TOP1P1 | 0.69 | 0.61 | 0.85 | 0.88 | 0.83 | 0.87 | 0.61 | 0.83 |
| CRH + GINM1 + SLC2A1 + TOP1P1 | 0.68 | 0.59 | 0.80 | 0.87 | 0.85 | 0.64 | 0.62 | 0.81 |
| ALDOB + KRT17 + SERPINE1 + SLC2A1 | 0.69 | 0.62 | 0.64 | 0.89 | 0.90 | 0.62 | 0.63 | 0.82 |
| KRT17 + LINC00967 + SERPINE1 + SLC2A1 | 0.69 | 0.61 | 0.74 | 0.87 | 0.88 | 0.53 | 0.63 | 0.81 |
| ALDOB + CRH + OLFM3 + SLC2A1 | 0.69 | 0.61 | 0.74 | 0.89 | 0.80 | 0.61 | 0.62 | 0.81 |
| CRH + SLC16A9 + SLC2A1 + TOP1P1 | 0.68 | 0.59 | 0.84 | 0.89 | 0.81 | 0.60 | 0.60 | 0.84 |
| KRT17 + LINC00967 + SLC16A9 + SLC2A1 | 0.68 | 0.58 | 0.78 | 0.88 | 0.87 | 0.57 | 0.60 | 0.84 |
| KRT17 + S100A13 + SLC16A9 + SLC2A1 | 0.68 | 0.59 | 0.74 | 0.89 | 0.86 | 0.55 | 0.60 | 0.83 |
| ALDOB + KRT17 + SLC2A1 + THAP7.AS1 | 0.68 | 0.60 | 0.65 | 0.87 | 0.88 | 0.65 | 0.61 | 0.81 |
| CRH + SLC2A1 + THAP7.AS1 + TPX2 | 0.67 | 0.58 | 0.81 | 0.89 | 0.82 | 0.83 | 0.58 | 0.84 |
| ALDOB + CHEK1 + KRT17 + SLC2A1 | 0.67 | 0.59 | 0.67 | 0.87 | 0.84 | 0.58 | 0.60 | 0.80 |
| ALDOB + KRT17 + OLFM3 + SLC2A1 | 0.67 | 0.59 | 0.62 | 0.87 | 0.86 | 0.62 | 0.61 | 0.79 |
| KRT17 + LINC00967 + S100A13 + SLC16A9 | 0.67 | 0.57 | 0.78 | 0.87 | 0.88 | 0.52 | 0.59 | 0.82 |
| CRH + GPRC5A + SLC16A9 + SLC2A1 | 0.66 | 0.56 | 0.88 | 0.89 | 0.76 | 0.51 | 0.57 | 0.85 |
| ALDOB + KRT17 + PCAT4 + SLC2A1 | 0.66 | 0.57 | 0.64 | 0.90 | 0.84 | 0.72 | 0.58 | 0.81 |
| CRH + KRT17 + SLC16A9 + SLC2A1 | 0.66 | 0.56 | 0.75 | 0.90 | 0.87 | 0.51 | 0.57 | 0.83 |
| ALDOB + AQP3 + KRT17 + SERPINE1 | 0.65 | 0.57 | 0.64 | 0.85 | 0.92 | 0.56 | 0.59 | 0.78 |
| KRT17 + LINC00967 + PCAT4 + SLC16A9 | 0.65 | 0.54 | 0.77 | 0.90 | 0.87 | 0.63 | 0.56 | 0.81 |
| ALDOB + FADS2 + KRT17 + SLC16A9 | 0.65 | 0.55 | 0.65 | 0.87 | 0.93 | 0.51 | 0.58 | 0.80 |
| KRT17 + LINC00967 + PCAT4 + S100A13 | 0.64 | 0.53 | 0.75 | 0.90 | 0.81 | 0.75 | 0.56 | 0.78 |
| ALDOB + CRH + THAP7.AS1 + TPX2 | 0.64 | 0.53 | 0.80 | 0.87 | 0.84 | 0.58 | 0.54 | 0.84 |
| ALDOB + AQP3 + KRT17 + LINC00967 | 0.64 | 0.54 | 0.71 | 0.85 | 0.92 | 0.65 | 0.57 | 0.78 |
| ALDOB + GAPDH + KRT17 + PCAT4 | 0.64 | 0.54 | 0.59 | 0.91 | 0.84 | 0.76 | 0.56 | 0.78 |
| ALDOB + AQP3 + KRT17 | 0.64 | 0.54 | 0.66 | 0.85 | 0.92 | 0.65 | 0.57 | 0.77 |
| KRT17 + LINC00967 + OLFM3 + PCAT4 | 0.64 | 0.53 | 0.74 | 0.90 | 0.82 | 0.70 | 0.56 | 0.78 |
| AQP3 + KRT17 + SLC16A9 | 0.64 | 0.54 | 0.64 | 0.85 | 0.92 | 0.51 | 0.56 | 0.79 |
| FADS2 + GINM1 + KRT17 + SLC16A9 | 0.64 | 0.54 | 0.65 | 0.86 | 0.92 | 0.53 | 0.56 | 0.79 |
| KRT17 + LINC00967 + PCAT4 + PRDM16 | 0.64 | 0.53 | 0.72 | 0.90 | 0.82 | 0.78 | 0.55 | 0.78 |
| C5orf30 + FADS2 + KRT17 + SLC16A9 | 0.63 | 0.53 | 0.63 | 0.86 | 0.92 | 0.54 | 0.55 | 0.80 |
| ALDOB + AQP3 + CASP7 + KRT17 | 0.63 | 0.54 | 0.64 | 0.85 | 0.92 | 0.61 | 0.56 | 0.77 |
| KRT17 + LINC00967 + PCAT4 + SLC41A1 | 0.63 | 0.52 | 0.73 | 0.90 | 0.83 | 0.74 | 0.55 | 0.78 |
| KRT17 + LINC00967 + PCAT4 | 0.63 | 0.51 | 0.73 | 0.90 | 0.83 | 0.71 | 0.54 | 0.78 |
| KRT17 + LINC00967 + PCAT4 + PLAT | 0.62 | 0.51 | 0.73 | 0.90 | 0.81 | 0.70 | 0.54 | 0.78 |
| GPRC5A + KRT17 + LINC00967 + PCAT4 | 0.62 | 0.51 | 0.78 | 0.89 | 0.78 | 0.69 | 0.54 | 0.78 |
| ALDOB + FADS2 + KRT17 + LRRCC1 | 0.62 | 0.52 | 0.59 | 0.85 | 0.94 | 0.56 | 0.55 | 0.76 |
| C5orf30 + KRT17 + SLC16A9 + TPX2 | 0.61 | 0.51 | 0.62 | 0.85 | 0.92 | 0.61 | 0.53 | 0.79 |

What is claimed is:

1. A method for treating a urothelial cancer in a human subject comprising;
    identifying the subject for treating the urothelial cancer by identifying that an expression level of at least two markers selected from the group consisting of SLC2A1, S100A13, KRT17, GPRC5A, P4HA1, and HSD17B2 in urinary exosomes and microvesicles isolated from the subject is higher than an expression level of the at least two markers in a urine sample obtained from a non-urothelial cancer subject; and
    administering a treatment selected from the group consisting of cystoscopy, tumor resection, surgery, chemotherapy, and cystectomy to the subject.

2. The method of claim 1, further comprising:
    detecting a reference gene wherein a said reference gene is used to normalize said expression level of said at least two markers wherein the reference gene is selected from the group consisting of ACTB, ALDOB, DHRS2 and UPK1A.

3. The method of claim 1, further comprising:
    detecting a reference gene wherein said reference gene is used to normalize the expression level of the at least two markers, wherein said reference gene is selected from the group consisting of ALDOB, DHRS2 and UPK1A.

4. The method of claim 2, wherein the normalization is done by a delta Ct method.

5. The method of claim 1, wherein the at least two markers are selected from the group consisting of SLC2A, S100A13, KRT17 and GPRC5A.

6. The method of claim 1, wherein the at least two markers are selected from the group consisting of SLC2A1, S100A13, and KRT17.

7. The method of claim 1, wherein a value of a diagnostic formula is obtained by machine learning technique such as logistic regression analysis and support vector machine using the expression level of more than one of said at least two markers.

8. A method of claim 1, wherein the urothelial cancer to be detected is selected from the group consisting of bladder cancer, renal pelvis cancer, and ureter cancer.

9. The method of claim 8, wherein the urothelial cancer to be detected is recurrent bladder cancer.

10. The method of claim 1, wherein the subject does not show a urine cytology positive result.

11. A method for treating a human subject with a urothelial cancer, the method comprising:
    identifying the subject for treating the urothelial cancer by identifying an expression of at least two RNAs associated with said urothelial cancer, comparing said at least two RNAs in a vesicle isolated from a urine sample from said subject with an expression of said at least two RNAs in a vesicle isolated from a urine sample of a healthy human donor, wherein the at least two RNAs are selected from the group consisting of KRT17, SLC2A1, ALDOB, LINC00967, SLC16A9, CRH, PCAT4, AQP3, THAP7, FADS2, SERPINE1, AS1, OLFM3, S100A13, C5orf30, GINM1, GPRC5A, P4HA1, HSD17B2, and TOP1P1, wherein an increase in said expression of said at least two RNAs of said subject compared to said expression of said at least two RNAs of said donor indicates said subject has urothelial cancer when said increase is beyond a threshold level,
    wherein said comparing said expression of said at least two RNAs in said vesicle isolated from said urine sample further comprises:
    (a) capturing said vesicle from said sample from said subject by moving said sample from said subject across a vesicle-capturing filter,
    (b) loading a lysis buffer onto said vesicle-capturing filter, thereby lysing said vesicle to release a vesicle-associated RNA,
    (c) quantifying said expression of said at least two RNAs associated with urothelial cancer in said vesicle-associated RNA by PCR,
    administering a treatment selected from the group consisting of cystoscony, tumor resection, surgery, chemotherapy, and cystectomy to the subject having urothelial cancer.

12. The method of claim 11, wherein quantifying said expression of said at least two RNAs by PCR comprises:
    contacting said vesicle-associated RNA with a reverse transcriptase to generate complementary DNA (cDNA);
    contacting said cDNA with sense and antisense primers that are specific for each of said at least two RNAs associated with urothelial cancer and with a DNA polymerase to generate amplified DNA;
    contacting said cDNA with sense and antisense primers that are specific for a reference RNA and with said DNA polymerase to generate amplified DNA; and
    using analytical software to determine an expression level or quantity or amount for each of said at least two RNAs.

13. The method of claim 12, wherein using analytical software to determine an expression level or quantity or amount for said at least two RNAs associated with urothelial cancer comprises:
    using analytical software to determine a marker cycle threshold (Ct) value for each of said at least two RNAs associated with urothelial cancer;
    using analytical software to determine a reference Ct value for a reference RNA; and
    subtracting the reference Ct value from the marker Ct value to obtain a marker delta Ct value.

14. The method of claim 12, wherein said at least two RNAs associated with urothelial cancer are selected from the group consisting of SLC2A1, S100A13, KRT17, GPRC5A, P4HA1, and HSD17B2.

15. The method of claim 13, wherein said reference RNA is selected from the group consisting of ACTB, ALDOB, DHRS2 and UPK1A.

16. The method of claim 13, wherein said increase is beyond said threshold level when said marker delta Ct value is less than 6.

17. The method of claim 11, wherein said comparing further comprises:
    determining a value of a diagnostic formula from said expression of said at least two RNAs isolated from said subject, wherein the diagnostic formula is a linear or non-linear mathematical formula, wherein the at least two RNAs is 2 genes to 20 genes, more preferably 2 genes to 10 genes.

18. The method of claim 17, wherein the at least two RNA is selected from the group consisting of KRT17, SLC2A1, ALDOB, LINC00967, SLC16A9, CRH, PCAT4, AQP3, THAP7, FADS2, SERPINE1, AS1, OLFM3, S100A13, C5orf30, GINM1, GPRC5A and TOP1P1.

19. The method of claim 18, wherein the at least two RNAs is selected from the group consisting of ALDOB, CRH, SERPINE1 and SLC2A1.

\* \* \* \* \*

SEQUENCE LISTING

<160> NUMBER OF SEQ ID NOS: 120

<210> SEQ ID NO 1
<211> LENGTH: 20
<212> TYPE: DNA
<213> ORGANISM: human

<400> SEQUENCE: 1
aagacagcag ccaacattcg                                           20

<210> SEQ ID NO 2
<211> LENGTH: 20
<212> TYPE: DNA
<213> ORGANISM: human

<400> SEQUENCE: 2
tttgcccgtc ccataaactg                                           20

<210> SEQ ID NO 3
<211> LENGTH: 23
<212> TYPE: DNA
<213> ORGANISM: human

-continued

```
<400> SEQUENCE: 3
tttttcctgg cacccagcac aat                                    23

<210> SEQ ID NO 4
<211> LENGTH: 25
<212> TYPE: DNA
<213> ORGANISM: human

<400> SEQUENCE: 4
tttttgccga tccacacgga gtact                                  25

<210> SEQ ID NO 5
<211> LENGTH: 20
<212> TYPE: DNA
<213> ORGANISM: human

<400> SEQUENCE: 5
aaccaccatt caagggcttg                                        20

<210> SEQ ID NO 6
<211> LENGTH: 20
<212> TYPE: DNA
<213> ORGANISM: human

<400> SEQUENCE: 6
ttggcgtttt cctggatagc                                        20

<210> SEQ ID NO 7
<211> LENGTH: 20
<212> TYPE: DNA
<213> ORGANISM: human

<400> SEQUENCE: 7
ttttgtttcg ggccccaatg                                        20

<210> SEQ ID NO 8
<211> LENGTH: 20
<212> TYPE: DNA
<213> ORGANISM: human

<400> SEQUENCE: 8
ttgtaggggt caacaatggc                                        20

<210> SEQ ID NO 9
<211> LENGTH: 20
<212> TYPE: DNA
<213> ORGANISM: human

<400> SEQUENCE: 9
tggcctggaa atgattcagc                                        20

<210> SEQ ID NO 10
<211> LENGTH: 20
<212> TYPE: DNA
<213> ORGANISM: human

<400> SEQUENCE: 10
ttgtgggcag tttccttacc                                        20

<210> SEQ ID NO 11
<211> LENGTH: 20
<212> TYPE: DNA
<213> ORGANISM: human
```

```
<400> SEQUENCE: 11
acagcacagc aagaattccc                                              20

<210> SEQ ID NO 12
<211> LENGTH: 20
<212> TYPE: DNA
<213> ORGANISM: human

<400> SEQUENCE: 12
tttgtgaccc tgcatgaagg                                              20

<210> SEQ ID NO 13
<211> LENGTH: 20
<212> TYPE: DNA
<213> ORGANISM: human

<400> SEQUENCE: 13
agcagagctt caggttttcc                                              20

<210> SEQ ID NO 14
<211> LENGTH: 20
<212> TYPE: DNA
<213> ORGANISM: human

<400> SEQUENCE: 14
tttcgagttg gctgttgcag                                              20

<210> SEQ ID NO 15
<211> LENGTH: 20
<212> TYPE: DNA
<213> ORGANISM: human

<400> SEQUENCE: 15
tttggttggc ttcacgactg                                              20

<210> SEQ ID NO 16
<211> LENGTH: 20
<212> TYPE: DNA
<213> ORGANISM: human

<400> SEQUENCE: 16
atggcatggc ttctgctttg                                              20

<210> SEQ ID NO 17
<211> LENGTH: 20
<212> TYPE: DNA
<213> ORGANISM: human

<400> SEQUENCE: 17
ttgctgaagc tgcctcaaag                                              20

<210> SEQ ID NO 18
<211> LENGTH: 20
<212> TYPE: DNA
<213> ORGANISM: human

<400> SEQUENCE: 18
tttctgcagc tttgggttgg                                              20

<210> SEQ ID NO 19
<211> LENGTH: 22
<212> TYPE: DNA
<213> ORGANISM: human
```

<400> SEQUENCE: 19
ttccacggtt ccaggctatt ac                                    22

<210> SEQ ID NO 20
<211> LENGTH: 20
<212> TYPE: DNA
<213> ORGANISM: human

<400> SEQUENCE: 20
tggcaactct gtcattcacc                                       20

<210> SEQ ID NO 21
<211> LENGTH: 20
<212> TYPE: DNA
<213> ORGANISM: human

<400> SEQUENCE: 21
tcttggtatt gcacggacac                                       20

<210> SEQ ID NO 22
<211> LENGTH: 22
<212> TYPE: DNA
<213> ORGANISM: human

<400> SEQUENCE: 22
tacccagagg caagtccaat tc                                    22

<210> SEQ ID NO 23
<211> LENGTH: 20
<212> TYPE: DNA
<213> ORGANISM: human

<400> SEQUENCE: 23
tcagcgccac aaagaatgac                                       20

<210> SEQ ID NO 24
<211> LENGTH: 20
<212> TYPE: DNA
<213> ORGANISM: human

<400> SEQUENCE: 24
aggtcaggtg aacttgcttg                                       20

<210> SEQ ID NO 25
<211> LENGTH: 21
<212> TYPE: DNA
<213> ORGANISM: human

<400> SEQUENCE: 25
aagcatctcc ttgtggatcg g                                     21

<210> SEQ ID NO 26
<211> LENGTH: 20
<212> TYPE: DNA
<213> ORGANISM: human

<400> SEQUENCE: 26
tggtttcctg caacgttctg                                       20

<210> SEQ ID NO 27
<211> LENGTH: 21
<212> TYPE: DNA
<213> ORGANISM: human

<400> SEQUENCE: 27
aggggtggtt tatctgcatg g                                              21

<210> SEQ ID NO 28
<211> LENGTH: 20
<212> TYPE: DNA
<213> ORGANISM: human

<400> SEQUENCE: 28
tgttgccaag ccaaagtctg                                                20

<210> SEQ ID NO 29
<211> LENGTH: 21
<212> TYPE: DNA
<213> ORGANISM: human

<400> SEQUENCE: 29
atctccctgg atctcacctt c                                              21

<210> SEQ ID NO 30
<211> LENGTH: 20
<212> TYPE: DNA
<213> ORGANISM: human

<400> SEQUENCE: 30
tgtgagcttg ctgtgctaac                                                20

<210> SEQ ID NO 31
<211> LENGTH: 22
<212> TYPE: DNA
<213> ORGANISM: human

<400> SEQUENCE: 31
tgagcagatc tgggacaaga tc                                             22

<210> SEQ ID NO 32
<211> LENGTH: 20
<212> TYPE: DNA
<213> ORGANISM: human

<400> SEQUENCE: 32
aagctgcaat ggaagagacc                                                20

<210> SEQ ID NO 33
<211> LENGTH: 20
<212> TYPE: DNA
<213> ORGANISM: human

<400> SEQUENCE: 33
tcggacagcc aacaattcag                                                20

<210> SEQ ID NO 34
<211> LENGTH: 21
<212> TYPE: DNA
<213> ORGANISM: human

<400> SEQUENCE: 34
agtccttgcc aaaaacatcc c                                              21

<210> SEQ ID NO 35
<211> LENGTH: 22
<212> TYPE: DNA
<213> ORGANISM: human

<400> SEQUENCE: 35
cctggtacat gtgcagaaat gg                                            22

<210> SEQ ID NO 36
<211> LENGTH: 20
<212> TYPE: DNA
<213> ORGANISM: human

<400> SEQUENCE: 36
acgcctttca tgacgcattc                                               20

<210> SEQ ID NO 37
<211> LENGTH: 22
<212> TYPE: DNA
<213> ORGANISM: human

<400> SEQUENCE: 37
ccaccttgtc cacaaattcg tc                                            22

<210> SEQ ID NO 38
<211> LENGTH: 20
<212> TYPE: DNA
<213> ORGANISM: human

<400> SEQUENCE: 38
aacacgtgca gcatgttcac                                               20

<210> SEQ ID NO 39
<211> LENGTH: 20
<212> TYPE: DNA
<213> ORGANISM: human

<400> SEQUENCE: 39
cccactcctc caccttgac                                                20

<210> SEQ ID NO 40
<211> LENGTH: 24
<212> TYPE: DNA
<213> ORGANISM: human

<400> SEQUENCE: 40
cataccagga aatgagcttg acaa                                          24

<210> SEQ ID NO 41
<211> LENGTH: 20
<212> TYPE: DNA
<213> ORGANISM: human

<400> SEQUENCE: 41
ttctggagca acgttttccc                                               20

<210> SEQ ID NO 42
<211> LENGTH: 22
<212> TYPE: DNA
<213> ORGANISM: human

<400> SEQUENCE: 42
cagctgctcc tgtaattcca ac                                            22

<210> SEQ ID NO 43
<211> LENGTH: 20
<212> TYPE: DNA
<213> ORGANISM: human

-continued

```
<400> SEQUENCE: 43
aatgtttccg cgactgaacc                                          20

<210> SEQ ID NO 44
<211> LENGTH: 20
<212> TYPE: DNA
<213> ORGANISM: human

<400> SEQUENCE: 44
ttggactgtg tgccatttcc                                          20

<210> SEQ ID NO 45
<211> LENGTH: 20
<212> TYPE: DNA
<213> ORGANISM: human

<400> SEQUENCE: 45
acgtgctgct gaactttcac                                          20

<210> SEQ ID NO 46
<211> LENGTH: 20
<212> TYPE: DNA
<213> ORGANISM: human

<400> SEQUENCE: 46
aaagaacaac gggggctttg                                          20

<210> SEQ ID NO 47
<211> LENGTH: 22
<212> TYPE: DNA
<213> ORGANISM: human

<400> SEQUENCE: 47
gctcatgctt cctgactttg ac                                       22

<210> SEQ ID NO 48
<211> LENGTH: 20
<212> TYPE: DNA
<213> ORGANISM: human

<400> SEQUENCE: 48
ttgtgagcag ccaaaactcg                                          20

<210> SEQ ID NO 49
<211> LENGTH: 25
<212> TYPE: DNA
<213> ORGANISM: human

<400> SEQUENCE: 49
tttttaacaa tgcatggccg tgaac                                    25

<210> SEQ ID NO 50
<211> LENGTH: 25
<212> TYPE: DNA
<213> ORGANISM: human

<400> SEQUENCE: 50
tttttatgct gctgacattc accag                                    25

<210> SEQ ID NO 51
<211> LENGTH: 20
<212> TYPE: DNA
<213> ORGANISM: human
```

```
<400> SEQUENCE: 51
aatcgccaga cccaaaaagc                                          20

<210> SEQ ID NO 52
<211> LENGTH: 20
<212> TYPE: DNA
<213> ORGANISM: human

<400> SEQUENCE: 52
aatcaccaag cacagcttcc                                          20

<210> SEQ ID NO 53
<211> LENGTH: 20
<212> TYPE: DNA
<213> ORGANISM: human

<400> SEQUENCE: 53
tggacaatgc caacatcctg                                          20

<210> SEQ ID NO 54
<211> LENGTH: 20
<212> TYPE: DNA
<213> ORGANISM: human

<400> SEQUENCE: 54
tcaaacttgg tgcggaagtc                                          20

<210> SEQ ID NO 55
<211> LENGTH: 22
<212> TYPE: DNA
<213> ORGANISM: human

<400> SEQUENCE: 55
tggagatggt tggggtcaaa tc                                       22

<210> SEQ ID NO 56
<211> LENGTH: 20
<212> TYPE: DNA
<213> ORGANISM: human

<400> SEQUENCE: 56
tgcatccaca aagcacactg                                          20

<210> SEQ ID NO 57
<211> LENGTH: 21
<212> TYPE: DNA
<213> ORGANISM: human

<400> SEQUENCE: 57
tgagctagca gccaaggaat c                                        21

<210> SEQ ID NO 58
<211> LENGTH: 20
<212> TYPE: DNA
<213> ORGANISM: human

<400> SEQUENCE: 58
ttgttgtgcc agctcatgtc                                          20

<210> SEQ ID NO 59
<211> LENGTH: 20
<212> TYPE: DNA
<213> ORGANISM: human
```

```
<400> SEQUENCE: 59
tgtaatgcaa cggtggaagc                                              20

<210> SEQ ID NO 60
<211> LENGTH: 22
<212> TYPE: DNA
<213> ORGANISM: human

<400> SEQUENCE: 60
tcatccatga tgatccctga gg                                           22

<210> SEQ ID NO 61
<211> LENGTH: 20
<212> TYPE: DNA
<213> ORGANISM: human

<400> SEQUENCE: 61
acacatcagc acaactacgc                                              20

<210> SEQ ID NO 62
<211> LENGTH: 20
<212> TYPE: DNA
<213> ORGANISM: human

<400> SEQUENCE: 62
ggtgcatttt cggttgttgc                                              20

<210> SEQ ID NO 63
<211> LENGTH: 20
<212> TYPE: DNA
<213> ORGANISM: human

<400> SEQUENCE: 63
tgccaacacc aacaaggaac                                              20

<210> SEQ ID NO 64
<211> LENGTH: 20
<212> TYPE: DNA
<213> ORGANISM: human

<400> SEQUENCE: 64
ttgcagttga gatgctggtc                                              20

<210> SEQ ID NO 65
<211> LENGTH: 20
<212> TYPE: DNA
<213> ORGANISM: human

<400> SEQUENCE: 65
accaaagagt gctgagcttg                                              20

<210> SEQ ID NO 66
<211> LENGTH: 20
<212> TYPE: DNA
<213> ORGANISM: human

<400> SEQUENCE: 66
tcatccaagc accaaatcgg                                              20

<210> SEQ ID NO 67
<211> LENGTH: 20
<212> TYPE: DNA
<213> ORGANISM: human
```

```
<400> SEQUENCE: 67
agttggagct agtgtttggc                                              20

<210> SEQ ID NO 68
<211> LENGTH: 20
<212> TYPE: DNA
<213> ORGANISM: human

<400> SEQUENCE: 68
ttgttgccaa ctagcactgg                                              20

<210> SEQ ID NO 69
<211> LENGTH: 25
<212> TYPE: DNA
<213> ORGANISM: human

<400> SEQUENCE: 69 tttttcacg atgcgatgtc atgtc                                         25

<210> SEQ ID NO 70
<211> LENGTH: 25
<212> TYPE: DNA
<213> ORGANISM: human

<400> SEQUENCE: 70 tttttgtcc caaattgtcg tccag                                         25

<210> SEQ ID NO 71
<211> LENGTH: 22
<212> TYPE: DNA
<213> ORGANISM: human

<400> SEQUENCE: 71
tgatcttggg cagaacatac cg                                           22

<210> SEQ ID NO 72
<211> LENGTH: 20
<212> TYPE: DNA
<213> ORGANISM: human

<400> SEQUENCE: 72
agcagcgcaa tgtcattgtc                                              20

<210> SEQ ID NO 73
<211> LENGTH: 20
<212> TYPE: DNA
<213> ORGANISM: human

<400> SEQUENCE: 73
acagtgcaac cacatcttcc                                              20

<210> SEQ ID NO 74
<211> LENGTH: 20
<212> TYPE: DNA
<213> ORGANISM: human

<400> SEQUENCE: 74
cgcaaagcca ttgatgatgc                                              20

<210> SEQ ID NO 75
<211> LENGTH: 22
<212> TYPE: DNA
<213> ORGANISM: human
```

```
<400> SEQUENCE: 75
ggacaaccac gcacttttag ac                                         22

<210> SEQ ID NO 76
<211> LENGTH: 20
<212> TYPE: DNA
<213> ORGANISM: human

<400> SEQUENCE: 76
ttcgcgttga tgcttggttc                                            20

<210> SEQ ID NO 77
<211> LENGTH: 20
<212> TYPE: DNA
<213> ORGANISM: human

<400> SEQUENCE: 77
tcctgcagag actcttctgg                                            20

<210> SEQ ID NO 78
<211> LENGTH: 20
<212> TYPE: DNA
<213> ORGANISM: human

<400> SEQUENCE: 78
cttgcgttgc actgattccc                                            20

<210> SEQ ID NO 79
<211> LENGTH: 20
<212> TYPE: DNA
<213> ORGANISM: human

<400> SEQUENCE: 79
tggtgttcca tttgccagtc                                            20

<210> SEQ ID NO 80
<211> LENGTH: 20
<212> TYPE: DNA
<213> ORGANISM: human

<400> SEQUENCE: 80
acaaaaggct ctctgcttgc                                            20

<210> SEQ ID NO 81
<211> LENGTH: 20
<212> TYPE: DNA
<213> ORGANISM: human

<400> SEQUENCE: 81
accaccttct tcacctttgc                                            20

<210> SEQ ID NO 82
<211> LENGTH: 22
<212> TYPE: DNA
<213> ORGANISM: human

<400> SEQUENCE: 82
cagctctttg aactcgttga cg                                         22

<210> SEQ ID NO 83
<211> LENGTH: 20
<212> TYPE: DNA
<213> ORGANISM: human
```

<400> SEQUENCE: 83
accctcagca tgttcattgc                          20

<210> SEQ ID NO 84
<211> LENGTH: 20
<212> TYPE: DNA
<213> ORGANISM: human

<400> SEQUENCE: 84
tcatgttgcc tttccagtgg                          20

<210> SEQ ID NO 85
<211> LENGTH: 22
<212> TYPE: DNA
<213> ORGANISM: human

<400> SEQUENCE: 85
tcaccccagt atttcgctta cc                       22

<210> SEQ ID NO 86
<211> LENGTH: 21
<212> TYPE: DNA
<213> ORGANISM: human

<400> SEQUENCE: 86
tggaactgaa gtctggacag c                        21

<210> SEQ ID NO 87
<211> LENGTH: 25
<212> TYPE: DNA
<213> ORGANISM: human

<400> SEQUENCE: 87
actccagagc tgctaatctc attgt                    25

<210> SEQ ID NO 88
<211> LENGTH: 26
<212> TYPE: DNA
<213> ORGANISM: human

<400> SEQUENCE: 88
aactagtaag acaggtggga ggttct                   26

<210> SEQ ID NO 89
<211> LENGTH: 22
<212> TYPE: DNA
<213> ORGANISM: human

<400> SEQUENCE: 89
gctctcatcg tcatcacttt gc                       22

<210> SEQ ID NO 90
<211> LENGTH: 20
<212> TYPE: DNA
<213> ORGANISM: human

<400> SEQUENCE: 90
agcacgtttt cctggtttcc                          20

<210> SEQ ID NO 91
<211> LENGTH: 20
<212> TYPE: DNA
<213> ORGANISM: human

```
<400> SEQUENCE: 91
acattggcgt tgctttctgg                                              20

<210> SEQ ID NO 92
<211> LENGTH: 21
<212> TYPE: DNA
<213> ORGANISM: human

<400> SEQUENCE: 92
attcccacag tcttcgtggt c                                            21

<210> SEQ ID NO 93
<211> LENGTH: 20
<212> TYPE: DNA
<213> ORGANISM: human

<400> SEQUENCE: 93
tcattgtggg catgtgcttc                                              20

<210> SEQ ID NO 94
<211> LENGTH: 21
<212> TYPE: DNA
<213> ORGANISM: human

<400> SEQUENCE: 94
accaggagca cagtgaagat g                                            21

<210> SEQ ID NO 95
<211> LENGTH: 22
<212> TYPE: DNA
<213> ORGANISM: human

<400> SEQUENCE: 95
tgttcaagag cccatctatg cc                                           22

<210> SEQ ID NO 96
<211> LENGTH: 20
<212> TYPE: DNA
<213> ORGANISM: human

<400> SEQUENCE: 96
tgagcgtgga acaaaaagcc                                              20

<210> SEQ ID NO 97
<211> LENGTH: 20
<212> TYPE: DNA
<213> ORGANISM: human

<400> SEQUENCE: 97
atcattgcca tggccatcag                                              20

<210> SEQ ID NO 98
<211> LENGTH: 20
<212> TYPE: DNA
<213> ORGANISM: human

<400> SEQUENCE: 98
tgcccccaac accattaatc                                              20

<210> SEQ ID NO 99
<211> LENGTH: 22
<212> TYPE: DNA
<213> ORGANISM: human
```

<400> SEQUENCE: 99
tgaggccata gtcaggaaac tc                                                    22

<210> SEQ ID NO 100
<211> LENGTH: 20
<212> TYPE: DNA
<213> ORGANISM: human

<400> SEQUENCE: 100
aatgtttcac gggcttagcg                                                       20

<210> SEQ ID NO 101
<211> LENGTH: 20
<212> TYPE: DNA
<213> ORGANISM: human

<400> SEQUENCE: 101
aacccgacaa aaaccagagc                                                       20

<210> SEQ ID NO 102
<211> LENGTH: 22
<212> TYPE: DNA
<213> ORGANISM: human

<400> SEQUENCE: 102
gcgatactgt ctttctcctg tg                                                    22

<210> SEQ ID NO 103
<211> LENGTH: 20
<212> TYPE: DNA
<213> ORGANISM: human

<400> SEQUENCE: 103
acatctttgt gcaccagctg                                                       20

<210> SEQ ID NO 104
<211> LENGTH: 22
<212> TYPE: DNA
<213> ORGANISM: human

<400> SEQUENCE: 104
aaggaactct aggaaggcaa cg                                                    22

<210> SEQ ID NO 105
<211> LENGTH: 20
<212> TYPE: DNA
<213> ORGANISM: human

<400> SEQUENCE: 105
agatgatgtg tgcaggcatc                                                       20

<210> SEQ ID NO 106
<211> LENGTH: 20
<212> TYPE: DNA
<213> ORGANISM: human

<400> SEQUENCE: 106
acatgccact ggtcagattg                                                       20

<210> SEQ ID NO 107
<211> LENGTH: 20
<212> TYPE: DNA
<213> ORGANISM: human

```
<400> SEQUENCE: 107
aaacagatgg ccttgggaac                                              20

<210> SEQ ID NO 108
<211> LENGTH: 20
<212> TYPE: DNA
<213> ORGANISM: human

<400> SEQUENCE: 108
tttcaatggc ccaggcaaac                                              20

<210> SEQ ID NO 109
<211> LENGTH: 20
<212> TYPE: DNA
<213> ORGANISM: human

<400> SEQUENCE: 109
agtcaccagc ctttgcattg                                              20

<210> SEQ ID NO 110
<211> LENGTH: 20
<212> TYPE: DNA
<213> ORGANISM: human

<400> SEQUENCE: 110
taatgtggca caggttgagc                                              20

<210> SEQ ID NO 111
<211> LENGTH: 20
<212> TYPE: DNA
<213> ORGANISM: human

<400> SEQUENCE: 111
cctgaacttg ggtcccatca                                              20

<210> SEQ ID NO 112
<211> LENGTH: 19
<212> TYPE: DNA
<213> ORGANISM: human

<400> SEQUENCE: 112
gccccaagct gctaaaagc                                               19

<210> SEQ ID NO 113
<211> LENGTH: 22
<212> TYPE: DNA
<213> ORGANISM: human

<400> SEQUENCE: 113
atccctgatc accaagcaga tg                                           22

<210> SEQ ID NO 114
<211> LENGTH: 20
<212> TYPE: DNA
<213> ORGANISM: human

<400> SEQUENCE: 114
aaggctgacg tgaagttcac                                              20

<210> SEQ ID NO 115
<211> LENGTH: 20
<212> TYPE: DNA
<213> ORGANISM: human
```

```
<400> SEQUENCE: 115
aggcgtgcct ggtttttatc                                                    20

<210> SEQ ID NO 116
<211> LENGTH: 20
<212> TYPE: DNA
<213> ORGANISM: human

<400> SEQUENCE: 116
aaatccaaac caggcaaccc                                                    20

<210> SEQ ID NO 117
<211> LENGTH: 20
<212> TYPE: DNA
<213> ORGANISM: human

<400> SEQUENCE: 117
ttgtgcagca agctgtttcc                                                    20

<210> SEQ ID NO 118
<211> LENGTH: 22
<212> TYPE: DNA
<213> ORGANISM: human

<400> SEQUENCE: 118
tatgtgcacg agaaggtctt cc                                                 22

<210> SEQ ID NO 119
<211> LENGTH: 20
<212> TYPE: DNA
<213> ORGANISM: human

<400> SEQUENCE: 119
aactgccaga ctttcaaccg                                                    20

<210> SEQ ID NO 120
<211> LENGTH: 20
<212> TYPE: DNA
<213> ORGANISM: human

<400> SEQUENCE: 120
atttgggggt tggttcttgg                                                    20
```